United States Patent [19]
Cheng et al.

[11] Patent Number: 5,807,819
[45] Date of Patent: Sep. 15, 1998

[54] PEPTIDES USEFUL FOR ALTERING BONE RESORPTION

[75] Inventors: Soan Cheng, San Diego; Ronald Ingram, Oceanside; Daniel Mullen; Juerg F. Tschopp, both of San Diego, all of Calif.

[73] Assignee: La Jolla Cancer Research Center, La Jolla, Calif.

[21] Appl. No.: 421,698

[22] Filed: Apr. 12, 1995

Related U.S. Application Data

[63] Continuation-in-part of Ser. No. 303,052, Sep. 8, 1994, which is a continuation-in-part of Ser. No. 227,316, Apr. 15, 1994, abandoned.

[51] Int. Cl.$^6$ .......................... A61K 38/08; A61K 38/10; A61K 38/12; A61K 38/16
[52] U.S. Cl. ................................ 514/11; 514/12; 514/13; 514/14; 514/15; 514/16; 514/17; 530/317; 530/324; 530/325; 530/326; 530/327; 530/328; 530/329
[58] Field of Search .................................. 514/9, 11, 12, 514/13, 14, 15, 16, 17; 530/317, 321, 324, 325, 326, 327, 328, 329

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,654,314 | 3/1987 | Takagi et al. | 501/82 |
| 4,661,111 | 4/1987 | Ruoslahti et al. | 623/11 |
| 4,792,525 | 12/1988 | Ruoslahti et al. | 435/240.24 |
| 5,041,380 | 8/1991 | Ruoslahti et al. | 435/240.2 |
| 5,192,746 | 3/1993 | Lobl et al. | 514/11 |
| 5,227,469 | 7/1993 | Lazarus et al. | 530/324 |

FOREIGN PATENT DOCUMENTS

| | | |
|---|---|---|
| 0425212 | 5/1991 | European Pat. Off. . |
| 437 367 A2 | 7/1991 | European Pat. Off. .......... C07K 7/10 |
| 578083 | 1/1994 | European Pat. Off. ....... A16K 37/02 |
| 0618225 | 10/1994 | European Pat. Off. . |
| WO89/05150 | 6/1989 | WIPO .............. A61K 37/02 |
| WO91/15515 | 10/1991 | WIPO .............. C07K 7/64 |
| WO 92/00995 | 1/1992 | WIPO . |
| WO 95/00544 | 1/1995 | WIPO . |
| WO 95/14714 | 6/1995 | WIPO . |

OTHER PUBLICATIONS

Aumailley et al., "Arg–Gly–Asp Constrained within Cyclic Pentapeptides Strong and Selective Inhibitors of Cell Adhesion to Vitronectin and Laminin Fragment P1," *FEBS Letters* 291(1):50–54 (1991).

Choi et al., "Inhibition of Neointimal Hyperplasia by Blocking $\alpha_v\beta_3$ Integrin with a Small Peptide Antagonist GpenGRGDSPCA," *J. Vascular Surg.* 19(1):125–134 (1994).

Fauchere et al., "Modulation of the Activity and Assessment of the Receptor Selectivity in a Series of New RGD–containing Peptides," *Int'l J. Peptide & Protein Res.* 42(5):440–444 (1993).

PCT Search Report (dated 9 Nov. 1995), International application No. PCT/US95/04741.

Nesbitt, Stephen et al., "Biochemical Characterization of Human Osteoclast Integrins." *J. Biol. Chem.* 268:16737–16745 (1993).

(List continued on next page.)

*Primary Examiner*—Jeffrey E. Russel
*Attorney, Agent, or Firm*—Campbell & Flores LLP

[57] ABSTRACT

The present invention provides Arg—Gly—Asp peptides that can alter the binding of osteoclasts to a matrix such as bone or can selectively alter integrin receptor binding. The invention also provides methods of using the Arg—Gly—Asp peptides to alter $\alpha_v\beta_3$ integrin receptor-mediated binding of a cell such as an osteoclast, endothelial cell or smooth muscle cell to a matrix. The invention further provides methods for ameliorating the severity of a pathology characterized, in part, by an undesirable level of bone resorption, angiogenesis or restenosis in a subject.

2 Claims, 19 Drawing Sheets

OTHER PUBLICATIONS

Hughes, D.E. et al., "Integrin Expression in Human Bone." *J. Bone & Mineral Res.* 8:527–533 (1993).

Ross, R. Patrick et al., "Interactions Between the Bone Matrix Proteins Osteopontin and Bone Sialoprotein and the Osteoclast Integrin $\alpha_v\beta_3$ Potentiate Bone Resorption." *J. Biol. Chem.* 268:9901–9907 (1993).

Chuntharapai Anan et al., "Blocking Monoclonal Antibodies to $\alpha_v\beta_3$ Integrin: A Unique Epitope of $\alpha_v\beta_3$ Integrin is Present on Human Osteoclasts." *Experimental Cell Res.* 205:345–352 (1993).

Helfrich, Miep H. et al., "Rat Osteoclasts Adhere to a Wide Range of RGD (Arg–Gly–Asp) Peptide–Containing Proteins, Including the Bone Sialoproteins and Fibronectin, via a $\beta_3$ Integrin." *J. Bone and Mineral Res.* 7:335–343 (1992).

Miyauchi, Akimitsu et al., "Recognition of Osteopontin and Related Peptides by an $\alpha_v\beta_3$ Integrin Stimulates Immediate Cell Signals in Osteoclasts." *J. Biol. Chem.* 266:20369–20374 (1991).

Yamakawa, Kensuke et al., "An Arg–Gly–Asp Peptide Stimulates $Ca^{2+}$ Efflux From Osteoclast Precursors Through a Novel Mechanism." *American Physiological Society.* 651–657 (1994).

Horton, M.A. et al., "Arg–Gly–Asp (RGD) Peptides and the Anti–Vitronectin Receptor Antibody 23c6 Inhibit Dentine Resorption and Cell Spreading by Osteoclasts." *Experimental Cell Res.* 195:368–375 (1991).

Horton, Michael A. et al., "Modulation of Vitronectin Receptor–Mediated Osteoclast Adhesion by Arg–Gly–Asp Peptide Analogs: A Structure–Function Analysis." *J. Bone and Mineral Res.* 8:239–247 (1993).

Sato, M. et al., "Echistatin is a Potent Inhibitor of Bone Resorption in Culture." *J. Cell Biol.* 111:1713–1723 (1990).

FIG. 1A
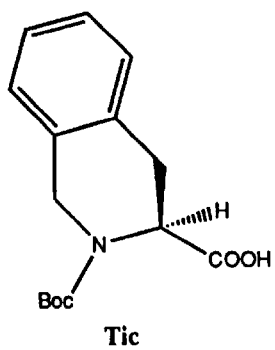
Tic
1,2,3,4-Tetrahydroisoquinoline-3-carboxylic acid
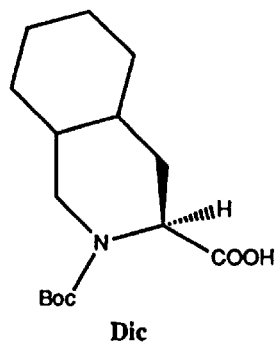
Dic
Decahydroisoquinoline-3-carboxylic acid
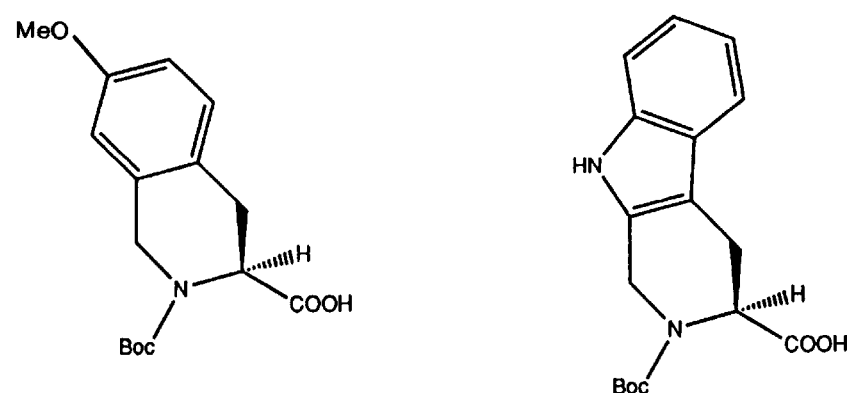
7-OMe-Tic
Tca
1,2,3,4,-Tetrahydro-β-carboline-3-carboxylic acid
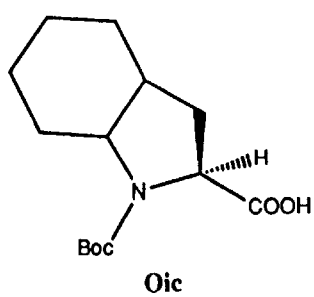
Oic
Octahydroindole-2-carboxylic acid
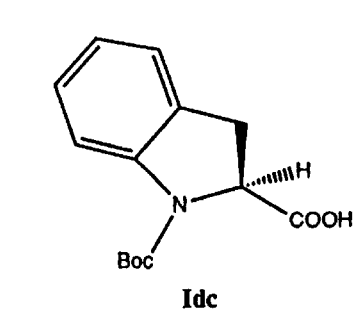
Idc
Indoline-2-carboxylic acid

FIG. 1B

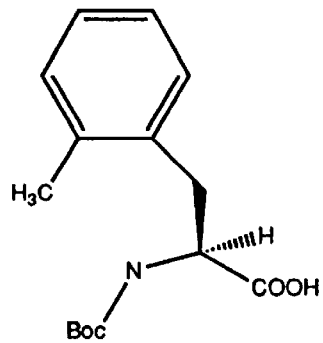

o-Methyl-phenylalanine

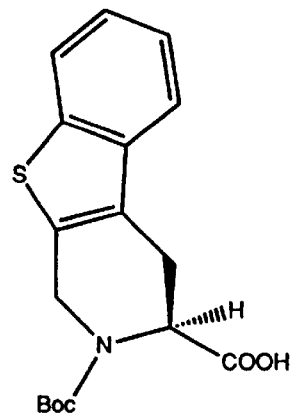

1,2,3,4-Tetrahydro[1]benzothieno[2,3-c]pyridine-3-carboxylic acid

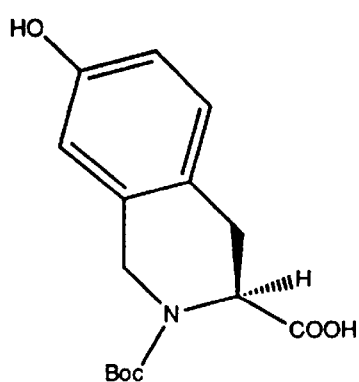

1,2,3,4-Tetrahydro-7-hydroxyisoquinoline-3-carboxylic acid

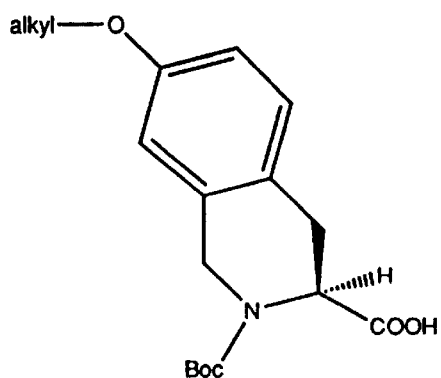

1,2,3,4-Tetrahydro-7-alkyloxy-isoquinoline-3-carboxylic acid

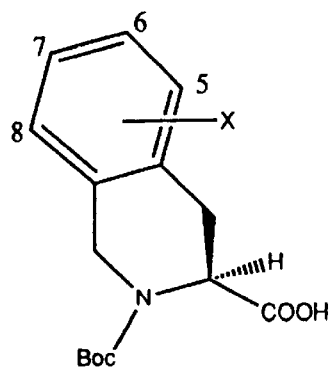

1,2,3,4-Tetrahydro-7-hydroxyisoquinoline-3-carboxylic acid derivatives wherein heteroatoms (X=F,Cl,Br,I) or alkyl (X=alkyl) groups are substituted at one of the following positions (5,6,7,8) or any combinations of positions.

Activity (IC50) of Osteoporosis Peptides

| | Peptide | | chick OC ATTACH (FCS) | Chick nonOC (FCS) | Rat OC attach (FCS) | Rat Bone (Pits) | Cell-Based Assays | | | | Receptor Assays | | |
|---|---|---|---|---|---|---|---|---|---|---|---|---|---|
| TL# | Sequence (SEQ ID NO:)* | | | | | | JY attach (αVβ3/Vn) | NRK attach (FCS) | Plate. Aggreg (hep) | MG63 attach (FCS) | αVβ3 (Vn) | αVβ5 (Vn) | α5β1 (Fn) |
| Echi | Echistatin | | 0.008 | 0.06 | 0.0013 | 0.0004 | 0.00030 | 0.85 | 0.046 | 1.2 | 0.0010 | 0.0023 | 0.00062 |
| 287 | GPenGRGDSPCA | (46) | 5.6 | | 14.9 | | 1.12 | 78 | | 97.9 | 0.042 | 0.20 | 0.060 |
| 233 | GRGDSP | (4) | | | 213 | | | 358 | | 249 | 0.080 | 0.35 | 0.085 |
| 1 | RGDS | (28) | | | 234 | | | | | | | 100 | |
| 2 | GRGESP | (29) | | | 1000 | | | | | | >100 | 100 | 100 |
| 198 | GRGDSPDG | (9) | 0.9 | | 2 | 2.1 | 0.037 | | | | 0.0042 | 0.053 | 0.050 |
| 247 | GPenGHRGDSPCA | (55) | 6.3 | | | | 0.88 | | | | | 1.6 | 0.36 |
| 100 | GPenRARGDNPCA | (56) | 3.1 | | 10.8 | 15 | 0.18 | | | | 0.052 | 0.33 | 0.0021 |
| 976 | PmpRGDSPPenG | (57) | 1.7 | | | | 0.29 | | | | | 0.214 | |
| 200 | AcCNPRGD(YOMe)RCNH2 | (58) | 139 | >100 | 23.8 | 83 | 18.5 | >400 | 2.1 | 513 | 0.33 | 5.6 | 8.7 |
| 676 | GPmcRGDCA | (34) | 1.8 | | | | 0.58 | | | | | 0.086 | 0.55 |
| 317 | KPenGFRGDEPCR | (40) | 6.8 | | | 100 | 3.4 | | | | | 7.0 | 2.9 |
| 31 | KPenGFRGDDPCR | (41) | 168 | >100 | 500 | | 13.3 | >400 | 400 | | 4.8 | 9.0 | 12.2 |
| 310 | GPenAARGDNPCA | (59) | 1.2 | | | | 0.17 | | | | | 0.11 | 0.0091 |
| 529 | GPenI(dF)RGDTPCA | | 85 | | 53.3 | | 6.4 | | | | | 6.1 | 3.3 |
| 99 | GPenIFRGDTFCA | (60) | 15 | | | | 0.72 | | | | | | |
| 65 | GPenAARGDSPCA | (61) | 3.0 | >10 | 17.6 | 57 | 0.10 | | | | 0.041 | 0.056 | 0.68 |
| 931 | GRGDSPDF | (10) | 1.6 | | | | 0.061 | | | | | 0.36 | 0.12 |
| 448 | GPenIARGDDLCA | (62) | 5.2 | >10 | 2.2 | 4.1 | 0.25 | | | | 0.015 | 0.086 | 0.84 |
| 451 | GPenGERGDNYCA | (36) | 6.1 | | | | 0.58 | | | | | 0.54 | 0.45 |
| 959 | FRGDSPEG | (11) | 3.8 | | | | 0.97 | | | | | 0.40 | 2.0 |
| 6 | AcPenAARGDN(dhP)CNH2 | (63) | 4.1 | | 2.5 | 26 | 0.49 | | | | 0.052 | 0.32 | 0.44 |
| 20 | AcCAARGDN(Tic)CNH2 | (64) | 1.0 | 7.7 | 0.68 | 2 | 0.05 | 12.5 | 37.2 | 16.1 | 0.0040 | 0.78 | 0.35 |
| 138 | GPenRARGDDVCA | (65) | 1.4 | >10 | | 2 | 0.33 | | | | 0.026 | 0.016 | 0.038 |
| 144 | GRGDTFENH2 | (12) | 1.2 | | 22.1 | | 0.13 | 1.9 | | 21.2 | 0.060 | 0.42 | 0.019 |
| 214 | AcPenFARGDNPCNH2 | (66) | 0.8 | | | 3.6 | 0.066 | | | | 0.0091 | 0.018 | 0.35 |
| 220 | AcFCRGDTFCNH2 | (22) | 1.1 | | | | 0.13 | | | | 0.014 | 0.14 | 0.019 |
| 221 | GPenEARGDNPCA | (67) | 1.2 | >10 | | | 0.203 | | | | | 0.008 | 0.26 |
| 228 | AcCRGDNPPenNH2 | (68) | 1.4 | >10 | 5.5 | 10 | 0.031 | | | | 0.0128 | 0.75 | 0.090 |
| 813 | AcPenAARGDNICNH2 | (69) | 2.6 | | | | 0.06 | | | | | 0.34 | 0.62 | 0.20 |

FIG. 2A

Activity (IC50) of Osteoporosis Peptides

| TL# | Peptide Sequence (SEQ ID NO:)* | chick OC ATTACH (FCS) | Chick nonOC (FCS) | Rat OC attach (FCS) | Rat Bone (Pits) | Cell-Based Assays JY attach (αvβ3/Vn) | NRK attach (FCS) | Plate. Aggreg (hep) | MG63 attach (FCS) | Receptor Assays αvβ3 (Vn) | αvβ5 (Vn) | α5β1 (Fn) |
|---|---|---|---|---|---|---|---|---|---|---|---|---|
| 832 | AcPenAARGDN(Tic)CNH2 (70) | 0.6 | 1.6 | 0.96 | 6.1 | 0.019 | 7.9 | 48.3 | 3.7 | 0.0021 | 0.008 | 0.0070 |
| 812 | AcCRGDS(Tic)CNH2 (45) | 0.6 | 3.3 | 0.44 | 1.4 | 0.0054 | | | | 0.0036 | 0.005 | 0.0073 |
| 831 | AcPenTARGDNPCNH2 (71) | 1.8 | | | | 0.006 | | | | | 0.50 | |
| 814 | GPenAARGDDVCANH2 (72) | 1.8 | >10 | 19 | 41 | 0.58 | >400 | 99.2 | | 0.042 | 2.4 | 0.25 |
| 825 | RGDSPENH2 (13) | 2.7 | | | | 0.25 | | | | | 0.75 | 0.037 |
| 390 | GRARGDNPENH2 (14) | 1.8 | | | | 0.096 | | | | | 0.96 | 0.025 |
| 385 | AcCAARGDY(Tic)CNH2 (73) | 4.8 | | 5.8 | | | | | | 0.0097 | | 0.0111 |
| 386 | RGDDVENH2 (3) | 1.2 | >10 | 1.9 | 0.9 | 0.026 | >400 | 87.8 | 27.0 | 0.026 | 0.55 | 0.039 |
| 389 | GPenAARGDVPCANH2 (37) | 2.2 | | | | 0.08 | | | | | 0.56 | 0.037 |
| 368 | GRGDDVDNH2 (7) | 1.6 | >10 | | 3.8 | 0.053 | | | | 0.0094 | 0.44 | 0.17 |
| 387 | AcPenFARGDSPCNH2 (74) | 1.5 | | | | 0.13 | | | | 1.1 | 0.026 |
| 365 | AcPen(YOMe)ARGDNPCNH2 (75) | 1.5 | | | | 0.033 | | | | | 0.61 | 0.011 |
| 375 | (p-Cl-F)RGDTPDNH2 (76) | 2.7 | | | | 0.03 | | | | | | |
| 366 | RGDTPENH2 (15) | 3.2 | | | | 0.07 | | | | | 0.21 | 0.024 |
| 373 | AcPenFARGDN(Tic)CNH2 (77) | 0.6 | 2.5 | 0.15 | 1.0 | 0.0018 | 5.1 | 18.9 | 0.71 | 0.0015 | 0.004 | 0.0027 |
| 388 | AcCRGDSPCNH2 (78) | 1.6 | | | | 0.22 | | | | | 0.97 | |
| 383 | GPenAARGDEPCNH2 (30) | 3.2 | | | | 1.00 | | | | | 1.9 | 0.13 |
| 186 | GPenAARGDDTCNH2 (79) | 4.7 | >10 | 13.5 | | | | 178.5 | | | 5.7 | 0.19 |
| 183 | AcPen(YOMe)ARGDN(Tic)CNH2 (80) | 0.4 | 2.2 | 0.078 (77) | 1.3 | 0.002 | 0.86 | 22 | 0.96 | 0.0015 | 0.006 | 0.0052 |
| 193 | G(Pen)ELRGDGWCNH2 (38) | 1.1 | >10 | 3.1 | 3 | 0.009 | >400 | 76.7 | 107.0 | 0.024 | 3.0 | 1.6 |
| 191 | MpaRGDDVCNH2 (81) | 0.12 | 1.2 | 0.41 | 2 | 0.018 | 0.32 | 6.1 | 1.1 | 0.0035 | 0.006 | 1.2 |
| 202 | AcPenFARGDS(Tic)CNH2 (82) | 0.4 | 1.7 | 2.6 | | 0.0037 | | | | 0.0066 | 0.011 | 0.0060 |
| 196 | AcCAARGDS(Tic)CNH2 (83) | 0.7 | 6.6 | 0.18 | | 0.047 | 10 | | | 0.0041 | 0.032 | 0.031 |
| 197 | βAlaAARGDN(Tic)DNH2 (84) | 1.9 | | 1.5 | | 0.0025 | 3.6 | | | 0.0017 | 0.007 | 0.022 |
| 206 | AcCAARGDT(Tic)CNH2 (85) | 0.2 | 1.8 | 0.14 | | 0.017 | 17.2 | | | 0.0064 | 0.011 | 0.029 |
| 199 | GCEPRGDN(Tic)CANH2 (86) | 0.35 | | 0.93 | | | 5 | 17.9 | | 0.011 | 0.027 | 0.071 |
| 192 | AcCRGDS(Tic)(Pen)NH2 (87) | | | 3.2 | | | | | | | 0.143 | 0.040 |
| 442 | GRGDEPDG (16) | | | 1.0 | | | 4.9 | | | 0.0026 | 0.008 | 0.0084 |
| 437 | AcCRGDT(Tic)CNH2 (88) | | | | | | | | | | | |

FIG. 2B

Activity (IC50) of Osteoporosis Peptides

| TL# | Peptide Sequence (SEQ ID NO:)* | chick OC ATTACH (FCS) | Chick nonOC (FCS) | Rat OC attach (FCS) | Rat Bone (Pits) | Cell-Based Assays JY attach (αvβ3/Vn) | NRK attach (FCS) | Plate. Aggreg (hep) | MG63 attach (FCS) | Receptor Assays αvβ3 (Vn) | αvβ5 (Vn) | α5β1 (Fn) |
|---|---|---|---|---|---|---|---|---|---|---|---|---|
| 434 | AcPenAARGDN(1-Nal)CNH2 (89) | | | (38) | | | | | | | | |
| 422 | GPen(dE)ARGDSPCNH2 | | | (40) | | | | | | | | |
| 438 | AcCAARGDN(fp)CNH2 (90) | | | 20.0 | | | | | | 0.23 | | |
| 441 | AcCRGDN(Tic)(Pen)NH2 (91) | | | 0.56 | | | 33.2 | | 7.0 | 0.0039 | 0.013 | 0.059 |
| 428 | GPenGFRGDEPCNH2 (39) | | | (100) | | | | | | | | |
| 424 | GPenGFRGDSPCNH2 (92) | | | (82) | | | | | | | | |
| 429 | AcCRGDS(Tic)CAKNH2 (93) | | | 2.0 | | | | | | 0.0049 | 0.018 | 0.015 |
| 427 | AcPenFARGDDVCNH2 (94) | | | 3.4 | 5 | | >400 | 63.9 | | 0.026 | 1.7 | 0.53 |
| 418 | AcPen(2-Nal)ARGDNPCNH2 (95) | | | (24) | | | | | | | | |
| 425 | AcRGDDVGNH2 (24) | | | 10.0 | | | | | | 1.6 | | |
| 430 | AcCAARGDN(7-OMeTic)CNH2 (96) | | | (41) | | | | | | 0.6160 | | |
| 432 | ACRGDSP(Pen)NH2 (97) | | | 0.64 | | | | | | | | |
| 431 | AcCAARGDN(Tic)CKNH2 (98) | | | (87) | | | 20 | | 8.7 | 0.0040 | 0.027 | 0.017 |
| 435 | AcPenI(nMeF)RGDTFCNH2 (99) | | | 1.3 | | | | | | | 0.028 | |
| 673 | TAPGKHPNRCAARGDN(Tic)CNH2 (100) | | | (41) | | | | | | 0.021 | 5.5 | 0.28 |
| 84 | AcPenFARGDD(PgL)CNH2 (101) | | | 2.0 | | | | | | 0.0050 | | |
| 90 | AcCFARGDT(Tic)CNH2 (102) | | | 12.5 | | 1.1 | 66 | 25.8 | 278.0 | 0.065 | 0.86 | 0.39 |
| 86 | AcCRGDDVCNH2 (17) | | | 0.81 | | | | | | 0.0058 | 0.55 | |
| 159 | (Mpa)RGDD(tBuG)CNH2 (103) | | | 12.9 | | | | | | 0.15 | 0.84 | |
| 92 | (Mpa)RGDD(cha)CNH2 (104) | | | 9.2 | | | | | >400 | 0.049 | 1.1 | |
| 94 | AcCIARGDDVCNH2 (18) | | | 9.3 | | | | | >400 | | | |
| 93 | RGDN(Tic)ENH2 (105) | | | 1.3 | | | 31 | | >400 | 0.0051 | 0.092 | 0.0087 |
| 713 | AcCAARGDN(Tic)CAKNH2 (106) | | | 3.3 | | | | | | 0.023 | 0.144 | |
| 172 | AcCRGDT(Tca)CNH2 (107) | | | 1.2 | | | | | | 0.0057 | 0.041 | 0.030 |
| 88 | AcCEPRGDDVCNH2 (19) | | | 9.2 | | | | | | 0.077 | 1.2 | |
| 125 | AcCRGDT(Ole)CNH2 (108) | | | 133 | | | | | | 0.011 | 0.28 | |
| 122 | AcCEARGDDVCNH2 (20) | | | 19 | | | | | | 0.042 | 5.2 | |
| 109 | Ac(Pen)EARGDDVCNH2 (109) | | | 4 | | | | | | 0.040 | 1.49 | 0.96 |
| 110 | GAARGDS(Tic)ENH2 (110) | | | >1 | | | | | 3.2 | 0.0095 | 0.033 | 0.025 |

FIG. 2C

Activity (IC50) of Osteoporosis Peptides

| | | | | Cell-Based Assays | | | | | Receptor Assays | | |
|---|---|---|---|---|---|---|---|---|---|---|---|
| | Peptide | chick OC ATTACH (FCS) | Chick nonOC attach (FCS) | Rat OC attach (FCS) | Rat Bone (Pits) | JY attach (αvβ3/Vn) | NRK attach (FCS) | Plate. Aggreg (hep) | MG63 attach (FCS) | αvβ3 (Vn) | αvβ5 (Vn) | α5β1 (Fn) |
| TL# | Sequence (SEQ ID NO:)* | | | | | | | | | | | |
| 126 | Ac(Pen)AARGDN(homoP)CNH2 (111) | | | 3.9 | | | | | | | | |
| 129 | RGDS(Adp)NH2 (112) | | | 18.3 | | | | | | | 0.84 | |
| 108 | AcCEPRGDN(Tic)CNH2 (113) | | | 0.5 | 2 | | | | | 0.016 | 0.030 | |
| 105 | (Pmp)AARGDDN(Tic)CNH2 (114) | | | 1.1 | | | 3.2 | 111.7 | 400.0 | 0.0039 | 0.027 | 0.12 |
| 124 | AARGDDV(Adp)NH2 (115) | | | 3.4 | | | | | | | | |
| 118 | Ac(Pen)EPRGDDVCNH2 (116) | | | 1.7 | | | | | | | | |
| 454 | (Mpa)RGDD(npG)CNH2 (117) | | | 4 | | | | | | | | |
| 121 | Ac(Pen)IGRGDD(tBuG)CA (118) | | | 20 | | | | | | | | |
| 114 | AcCKGDDVCNH2 (8) | | | 100 | | | | | | | | |
| 473 | AcACRGDDVCANH2 (28) | | | 12.2 | | | | | | | | |
| 476 | (Mpa)RGDD(tBuG)CA (119) | | | 1.5 | | | | 23.8 | | 0.0022 | 0.90 | 0.0669 |
| 479 | (Mpa)RGD(tetA)(tBuG)CNH2 (120) | | | 3.2 | | | | 12.1 | | 0.0015 | 0.193 | 0.1700 |
| 477 | AcCAA(HomoR)RGDN(Tic)CNH2 (121) | | | 5.5 | | | | | | 0.021 | 1.7 | 0.4510 |
| 488 | AcC(nMeR)GDT(Tic)CNH2 (122) | | | 0.044 | | | 0.79 | 6.3 | 2.5 | 0.0079 | 0.005 | 0.010 |
| 482 | (Mpa)RGDD(tBuG)CAKNH2 (123) | | | 0.29 | | | | 10.3 | | 0.010 | 0.78 | 0.081 |
| 484 | (Mpa)RGDD(tBuG)CDNH2 (124) | | | 0.27 | | | | 13.5 | | 0.011 | 1.4 | 0.072 |
| 483 | AcFCRGDT(Tic)CNH2 (125) | | | 0.76 | | | | 4.7 | | 0.012 | 0.006 | 0.0049 |
| 492 | (Mpa)RGD(Msa)(tBuG)CNH2 (126) | | | 0.76 | | | | 1.3 | | 0.099 | 0.41 | 0.065 |
| 487 | GRGDD(tBuG)ENH2 (127) | | | 0.072 | | | 32 | 24.5 | 72.3 | 0.0056 | 0.48 | 0.10 |
| 485 | (Mpa)RGDD(tBuG)CFNH2 (128) | | | 0.84 | | | | 8.4 | | 0.0088 | 0.053 | 0.076 |
| 478 | (bAla)RGDD(tBuG)DNH2 (129) | | | >32 | | | | | | 0.086 | 3.5 | 0.42 |

FIG. 2D

Activity (IC50) of Osteoporosis Peptides

| | Peptide | | Cell-Based Assays | | | | | Receptor Assays | | |
|---|---|---|---|---|---|---|---|---|---|---|
| TL# | Sequence (SEQ ID NO:)* | chick OC ATTACH (FCS) | Chick nonOC attach (FCS) | Rat OC attach (FCS) | Rat Bone (Pits) | JY attach (αvβ3/Vn) | NRK attach (FCS) | Plate. Aggreg (hep) | MG63 attach (FCS) | αvβ3 (Vn) | αvβ5 (Vn) | α5β1 (Fn) |
| 735 | (Mpa)(nMeR)GDD(tBuG)CNH2 (130) | | | >20 | | | | | | | | |
| 754 | (Mpa)RGD(Psa)(tBuG)CNH2 (131) | | | 0.11 | | | | 0.77 | | 0.0078 | 0.15 | 0.0200 |
| 746 | (Mpa)RGD(Cha)(tBuG)CNH2 (44) | | | 0.13 | | | | 7.9 | | 0.021 | 1.52 | 0.35 |
| 733 | (Mpa)RGD(YOMe)(tBuG)CNH2 (132) | | | 0.027 | | | 210 | 4.1 | 302. | 0.012 | 3.2 | 0.68 |
| 734 | (Mpa)RGDDVCAKNH2 (133) | | | | | | | | | | | |
| 750 | (Mpa)RGDD(PgL)CNH2 (134) | | | 0.011 | | | 112 | 90.8 | 346. | 0.029 | 0.30 | 1.5 |
| 753 | AcACRGDEVCANH2 (27) | | | | | | | | | 0.093 | 0.57 | 2.8 |
| 751 | RGDD(tBuG)(Mamb) (135) | | | 0.070 | | | 8.8 | | 25.3 | 0.0006 | 0.014 | 0.042 |
| 731 | (Mpa)RGD(Tisa)(tBuG)CNH2 (136) | | | 0.43 | | | | 6.75 | | | | 0.86 |
| 729 | Ac(Pen)(YOMe)ARGDT(Tic)CNH (137) | | | | | | | | | | | |
| 739 | (Mpa)RGDD(tBuG)CAKNH2 (123) | | | | | | | | | | | |
| 940 | RGD(YOMe)RENH2 (138) | | | 2.1 | | | >400 | 0.82 | | 0.0042 | 10 | 0.43 |

FIG. 2E

*- Numbers in parentheses next to sequences are SEQ ID NOS:

FIG. 3

CYCLIC RGD PEPTIDES

5  G-Pen-R-A-R-G-D-D-L-C-A (SEQ ID NO: 48)
   G-Pen-R-A-R-G-D-D-nL-C-A (SEQ ID NO: 49)
   G-Pen-A-A-R-G-D-D-I-C-A (SEQ ID NO: 50)
   G-dPen-G-R-G-D-D-V-C-NH$_2$
   βAla-R-A-R-G-D-N-P-D-NH$_2$ (SEQ ID NO: 51)
10 Ac-Pen-A-A-R-G-D-Orn-P-C-NH$_2$ (SEQ ID NO: 42)
   Ac-Pen-F-A-R-G-D-N-Pgl-C-NH$_2$ (SEQ ID NO: 52)
   Ac-C-A-A-R-G-D-T-P-C-NH$_2$ (SEQ ID NO: 21)
   Ac-F-C-R-G-D-T-F-C-NH$_2$ (SEQ ID NO: 22)
   Ac-C-I-F-R-G-D-T-F-C-NH$_2$ (SEQ ID NO: 23)
15 Ac-Pen-I-(p-Cl-F)-R-G-D-T-F-C-NH$_2$ (SEQ ID NO: 53)
   R-G-D-S-Tic-E-NH$_2$ (SEQ ID NO: 54)

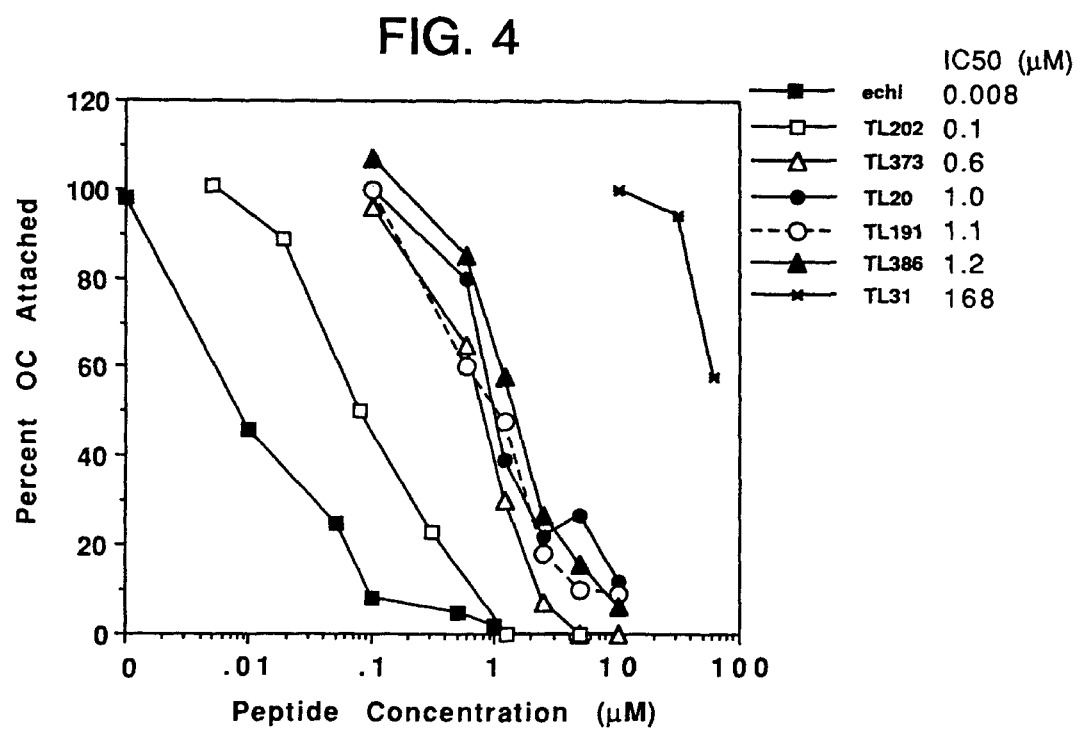

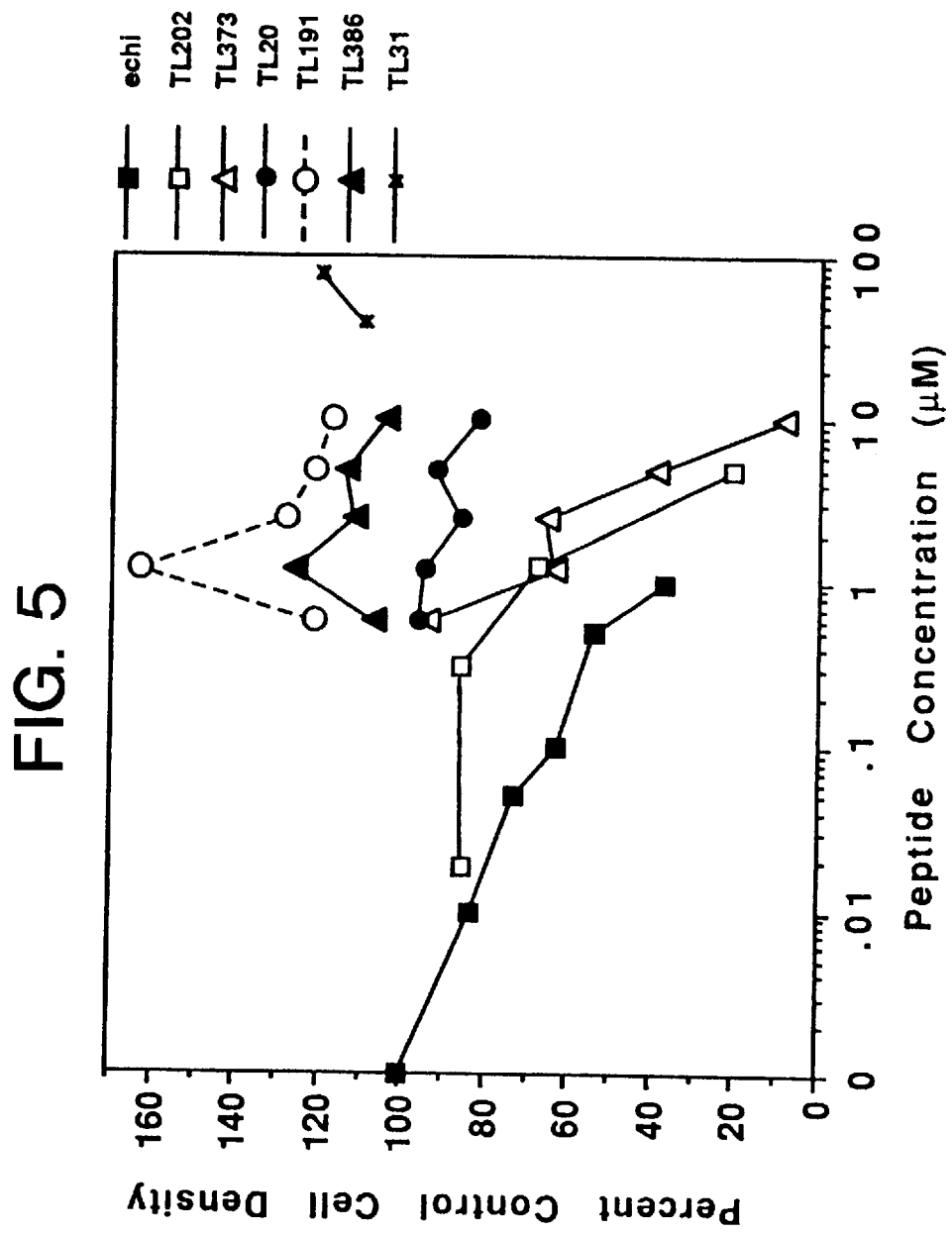

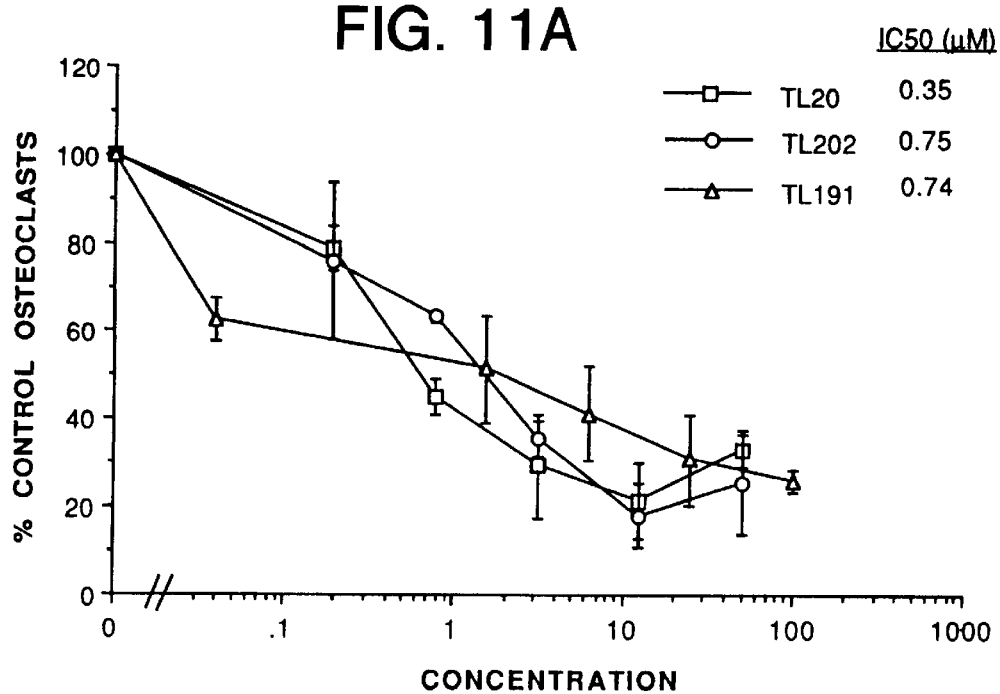
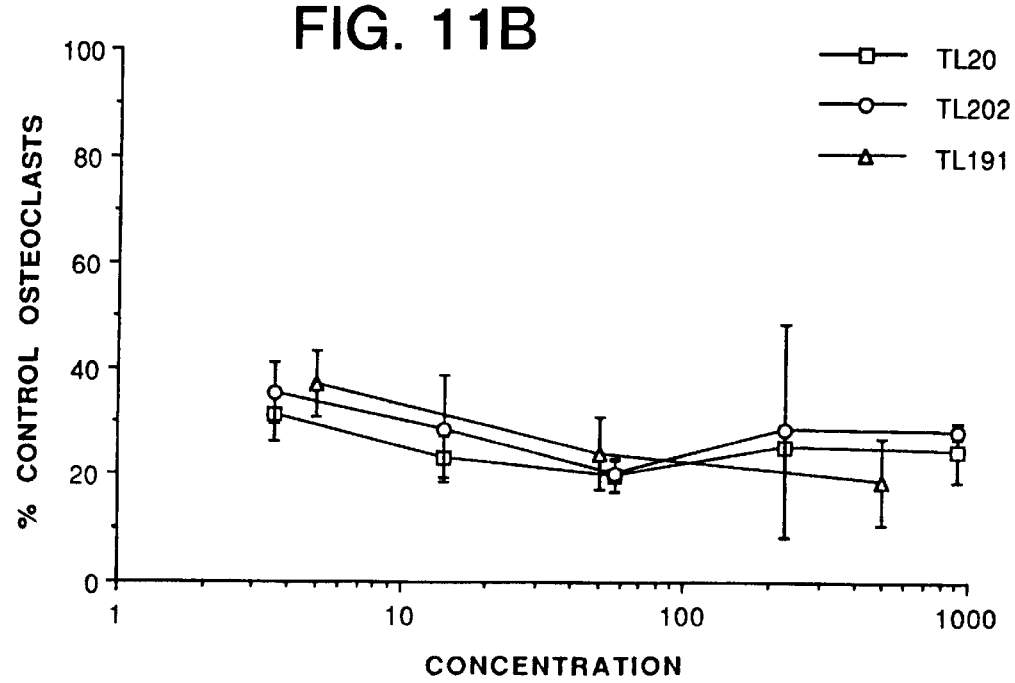

PEPTIDES USEFUL FOR ALTERING BONE RESORPTION

BACKGROUND OF THE INVENTION

This application is a continuation-in-part of U.S. Ser. No. 08/303,052, filed Sep. 8, 1994, which is a continuation-in-part of U.S. Ser. No. 08/227,316, filed Apr. 13, 1994, now abandoned.

FIELD OF THE INVENTION

This invention relates generally to the field of medicine and more specifically to peptides that can reduce or inhibit bone resorption, angiogenesis and restenosis.

Background Information

Bone is a dynamic tissue that is continually remodeled throughout life depending on factors such as nutrition and the load the bone must carry. Normal bone formation depends on the delicate balance between new bone addition and old bone resorption. Bone resorption is initiated when an osteoclast attaches to the surface of mineralized bone, forms a tight sealing zone and secretes enzymes that begin the resorption process. After a period of several hours to days, the osteoclast detaches from the bone, leaving a pit on the bone surface. Under normal conditions, the pit is a target for osteoblasts, which deposit a material that ultimately becomes new bone.

Bone loss can result when the bone resorptive process is dominant over the bone formative process. Such a condition can occur, for example, when a previously active person becomes sedentary or incapacitated due to an injury or illness, when a person fails to ingest an adequate amount of vitamins and minerals or in various pathological conditions. A condition of excessive bone loss, which is called osteoporosis, is common in elderly persons.

When osteoporosis is caused by a mineral or vitamin deficiency, the condition often can be treated by supplementing the person's diet with the appropriate nutrient. However, diet supplementation is not always effective and, in most cases, osteoporosis cannot be treated. In severe cases, osteoporosis can result in the formation of fragile bones that readily fracture when placed under a minimal load or stress. Thus, a need exists for agents that can reduce or inhibit bone resorption in a subject or to achieve net bone accumulation. The present invention satisfies this need and provides related advantages as well.

SUMMARY OF THE INVENTION

The present invention provides non-naturally occurring RGD-containing peptides useful for reducing or inhibiting bone resorption, angiogenesis or restenosis and for altering an integrin receptor-mediated interaction. In addition, the invention provides pharmaceutical compositions comprising a non-naturally occurring RGD-containing peptide.

The invention also provides methods for specifically altering $\alpha_V\beta_3$ integrin receptor-mediated binding of a cell to a matrix. The invention provides, for example, methods of reducing or inhibiting osteoclast binding to a matrix, altering angiogenesis and reducing or inhibiting bone resorption or restenosis in a subject. The invention further provides methods for using an RGD-containing peptide to alter the binding of a ligand to an $\alpha_V\beta_3$ integrin receptor.

BRIEF DESCRIPTION OF THE FIGURES

FIG. 1 shows the names and structures of Tic and representative Tic analogs.

FIG. 2 lists and demonstrates the activity of various RGD peptides of the invention. All of the peptides are cyclic except peptides 1, 2, 233 and 425, which are linear. Values indicated are mean 50% inhibitory concentration (IC50; $\mu$M) for the interactions listed across the top of the table. IC50 values were determined by linear regression analysis (1 to 5 assays), except that numbers in parentheses in the column headed "rat OC attach (FCS)" were obtained from a single experiment using 5 $\mu$M peptide and represent the percent of osteoclasts remaining adherent in the presence of peptide as compared to osteoclasts remaining adherent in the absence of peptide. OC, osteoclast; FCS, fetal calf serum; Echi, echistatin; JY, human B lymphocyte-derived JY cell line; Vn, vitronectin; Hep, heparin. Regarding the peptide sequences, "NH2" indicates the presence of an amide group at the C-terminus; dE indicates the D-amino acid form of glutamic acid; dF indicates the D-amino acid form of phenylalanine. Other abbreviations are listed in Table 1 (see, also, FIG. 1, for Tic and Tic analogs). SEQ ID NO. is listed for peptides containing only L-amino acids.

FIG. 3 lists additional RGD peptides of the invention. Underlining indicates the amino acids in the cyclic region of the peptide. SEQ ID NO. is listed for peptides containing only L-amino acids. dPen indicates the D-amino acid form of penicillamine. Other abbreviations are listed in Table 1 (see, also, FIG. 1, for Tic and Tic analogs).

FIG. 4 demonstrates the dose response of various RGD peptides in the chick osteoclast cell detachment assay. The IC50 was calculated by determining the dose of a peptide that results in the detachment of 50% of the osteoclasts and is shown for each peptide. Echi indicates echistatin. Peptide TL31 is a negative control.

FIG. 5 demonstrates the selectivity of various peptides in the chick total cell detachment assay. A selective peptide produces a curve that is shifted to the right and has a horizontal shape.

FIG. 11 demonstrates the effectiveness of various RGD peptides of the invention in the rat osteoclast attachment assay using collagen as substrate .

DETAILED DESCRIPTION OF THE INVENTION

Figure 6A:
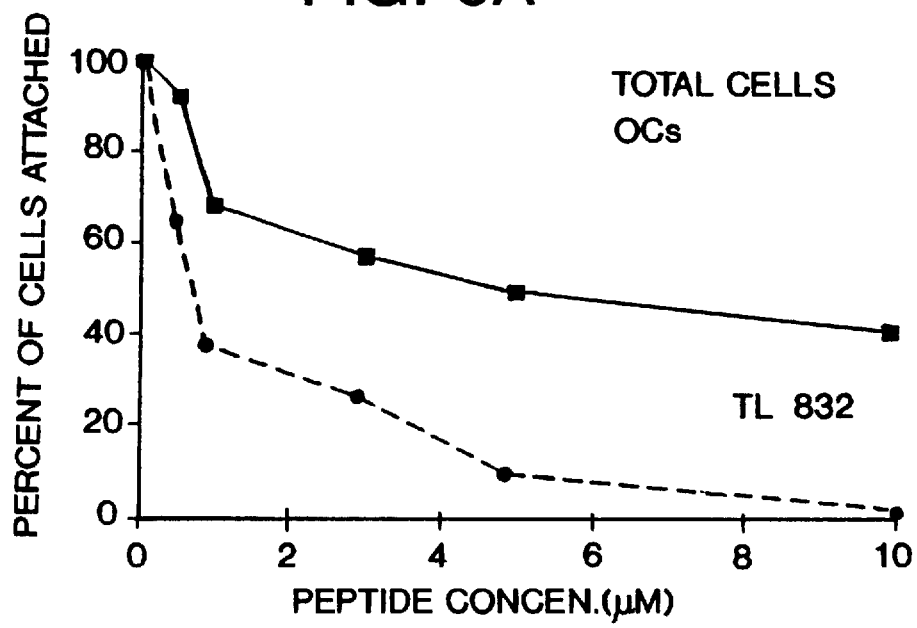
FIG. 6 compares various peptides in both the chick osteoclast detachment assay (OCs) and chick total cell detachment assay (Total Cells). Peptides showing a greater difference in the ability to detach osteoclasts as compared to total cells are considered more selective.
Figure 6B:
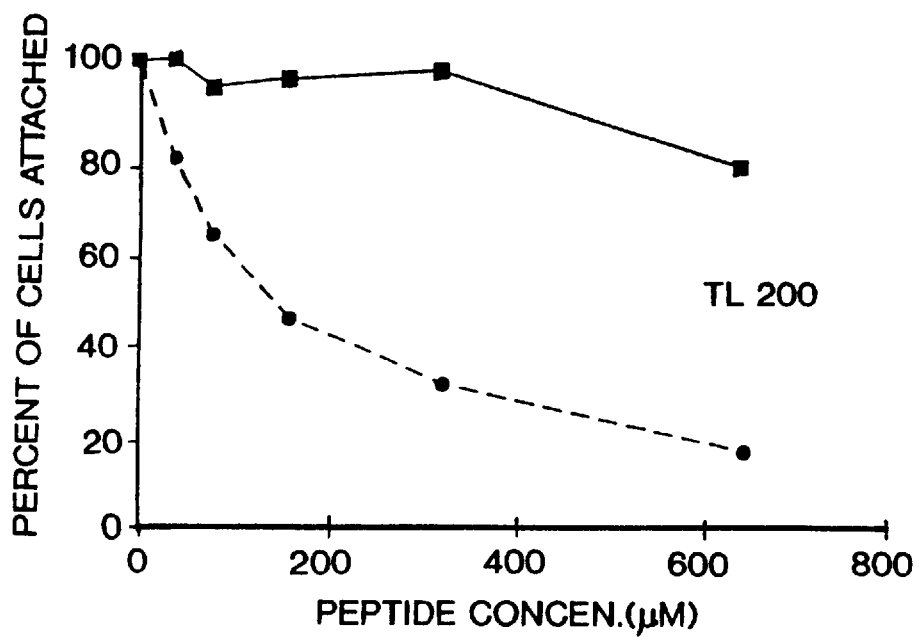
Figure 6C:
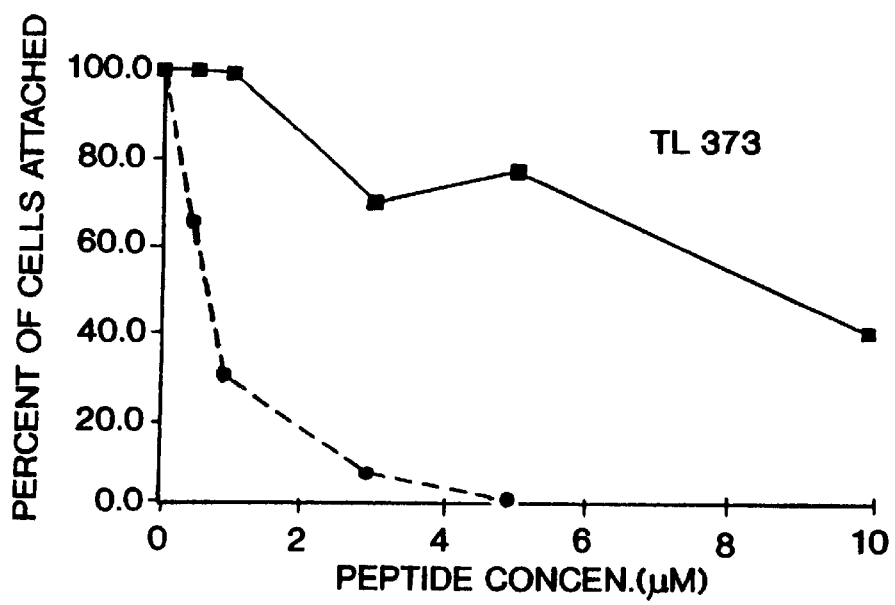
Figure 6D:
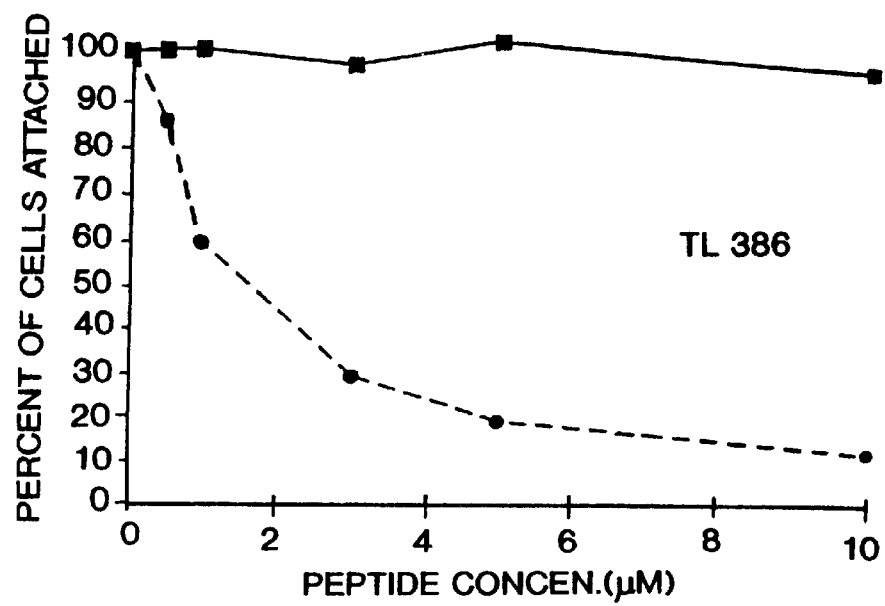

The present invention provides non-naturally occurring Arg—Gly—Asp (RGD) peptides that can inhibit bone resorption and can inhibit the binding of an osteoclast to a matrix such as bone (see, for example, Davies et al., *J. Cell. Biol.* 109:1817 (1989); Horton et al., *Expt. Cell Res.* 135:368 (1990)). RGD peptides of the invention also can bind the $\alpha_V\beta_3$ integrin and, therefore, can inhibit or promote $\alpha_V\beta_3$-mediated cell attachment depending on whether they are presented to the cell in a soluble form or bound to a solid substrate, respectively. Since $\alpha_V\beta_3$ integrins are involved in angiogenesis and in the restenosis that can occur following angioplasty, the RGD peptides of the invention can be useful for altering angiogenesis and for reducing or inhibiting restenosis in a subject (see Choi et al., *J. Vasc. Surg.* 19:125 (1994); Brooks et al., *Cell* 79:1157–1164 (1994a); Brooks et al., *Science* 264:569 (1994b), each of which is incorporated herein by reference).

As used herein, the term "Arg—Gly—Asp peptide" or "RGD peptide" means a peptide having at least one Arg—Gly—Asp-containing sequence, as defined below, which can function as a binding site for an integrin type receptor (see Table 1 for amino acid codes). Integrin receptors can bind a variety of RGD-containing peptides (see, for example, Ruoslahti et al., In *Morphoregulatory Molecules* (G. M. Edelman et al., eds. 1990); Ruoslahti, *J. Clin. Invest.* 87:1–5 (1991)).

It is intended that the term "RGD peptide" in its broadest sense includes a peptide comprising Arg—Gly—Asp or a functional equivalent of Arg—Gly—Asp. For example, an amino acid such as lysine, homoarginine (homoArg), N-methyl arginine or a mimic of these amino acids is a functional equivalent of arginine. Similarly, mimics of Gly and Asp are functional equivalents of glycine and aspartic acid, respectively. Therefore, a peptide comprising, for example, Lys—Gly—Asp is considered an "RGD peptide" within the meaning of the present invention. As used herein, the term "mimic" means an amino acid or an amino acid analog that has the same or a similar functional characteristic of an amino acid. Thus, for example, an arginine analog can be a mimic of arginine if the analog contains a side chain having a positive charge at physiologic pH, as is characteristic of the guanidinium side chain reactive group of arginine. A peptide mimetic or peptidomimetic is an organic molecule that retains similar peptide chain pharmacophore groups as are present in the corresponding

TABLE 1

| Single letter code | Three letter code | Amino acid*+ |
|---|---|---|
| | Adp | γ-aminoadipic acid |
| A | Ala | Alanine |
| | βAla | β-alanine |
| | α-Aba | α-Amino isobutyric acid |
| R | Arg | Arginine |
| N | Asn | Asparagine |
| D | Asp | Aspartic acid |
| | Cha | Cyclohexyl-alanine |
| | Chg | cyclohexyl-glycine |
| | Cit | Citrulline |
| C | Cys | Cysteine |
| Q | Gln | Glutamine |
| E | Glu | Glutamic acid |
| G | Gly | Glycine |
| | t-BuG | tert-butyl Glycine |
| H | His | Histidine |
| | Hpa | Homophenylalanine |
| I | Ile | Isoleucine |
| L | Leu | Leucine |
| | nL | norleucine |
| K | Lys | Lysine |
| M | Met | Methionine |
| | Mpa | β-Mercaptopropionic acid |
| | Msa | β-[(methylsulfonyl)amino]alanine |
| | Mamb | m-(aminomethyl) benzoic acid |
| | N-Me-R | N-methyl-arginine |
| | Npg | neopentyl-glycine |
| | OMeTic | O-methyl-Tic+ |
| | Orn | Ornithine |
| | p-amino-Phe | para-amino-phenylalanine |
| | Pen | Penicillamine |
| | PgL | phenyl-glycine |
| F | Phe | Phenylalanine |
| | p-Cl-F | para-chloro-phenylalanine |
| | p-iodo-Phe | para-iodo-phenylalanine |
| | Pmc | β,β-pentamethylene cysteine |
| | Pmp | β,β-pentamethylene-β-mercaptopropionic acid |
| P | Pro | Proline |
| | homoP | homoproline |
| | dhP | dehydroproline |
| | fp | 3-phenylproline |
| | Psa | β-[(phenylsulfonyl)amino]alanine |
| S | Ser | Serine |
| | Tca | 1,2,3,4-tetrahydro-β-carboline-3-carboxylic acid |
| | tetA | β-(1(2)H-tetrazol-5-yl)-alanine |
| T | Thr | Threonine |
| | Tfsa | β-[(trifluoromethyl sulfonyl)amino]alanine |
| W | Trp | Tryptophan |
| Y | Tyr | Tyrosine |
| | YOMe | O-methyl-tyrosine |
| V | Val | Valine |
| | 2-Nal | β-(2-naphthyl) Ala-OH |
| | 1-Nal | β-(1-naphthyl) Ala-OH |

\* — includes amino acids and analogs thereof
+ — for Tic and Tic analogs, see FIG. 1 peptide. Peptide mimetics also can be functional equivalents of Arg—Gly—Asp.

In one aspect, the RGD peptides of the invention are grouped based on the pharmacophore. As used herein, the term "pharmacophore" is defined as a particular three-dimensional arrangement of functional groups that is required for a compound to produce a particular response or have a desired activity. The invention provides, for example, a pharmacophore, abbreviated "RGDNTic," (SEQ ID NO:

31) which is contained within a non-naturally occurring peptide comprising the sequence:

$$X_1X_2X_3X_4GD\ X_5X_6X_7X_8 \quad \text{(SEQ ID NO: 32)}$$

wherein $X_1$ is $R_1R_2N$ (wherein $R_1$ is an H or alkyl group and $R_2$ is an H, alkyl, $CH_3CO$, alkyl—CO or phenyl—CO group) or 0 to 10 amino acids, which can be protected by acetylation at the N-terminus; $X_2$ is 0 or 1 amino acid, which, when $X_2$ is one amino acid, can form a bridge with $X_7$; $X_3$ is 0, 1 or 2 amino acids, which, when $X_3$ is two amino acids, the amino acids can be a pair consisting of Phe—Ala, Ala—Ala, Glu—Ala, Tyr—Ala, Arg—Ala, Ile—Ala, Glu—Pro, Ile—Phe, (2-Nal)—Ala, YOMe—Ala or analogs or mimics thereof; $X_4$ is a positively charged amino acid such as Arg, Lys, homoArg, N—Me—Arg or analogs or mimics thereof; $X_5$ is an amino acid such as Asn, Ser, Thr or mimics or analogs thereof, which can provide a hydrogen bond interaction with an integrin receptor; $X_6$ is an amino acid such as Tic, Pro, Phe, Ile or analogs or mimics thereof, which have the characteristics of hydrophobicity and/or conformational constraint; $X_7$ is a residue capable of forming a bond with an amino acid of $X_2$, or with $X_3$ when $X_2$ is 0, or with $X_4$ when $X_2$ and $X_3$ are 0, to conformationally restrain the peptide; and $X_8$ is —$CONR_3R_4$ (wherein $R_3$ is an H or alkyl group and $R_4$ is an H or alkyl group) or —$COOR_5$ (wherein $R_5$ is an H or alkyl group) or 0 to 10 amino acids, which can be protected as an amide at the C-terminus, and wherein when $X_5$ is serine and $X_6$ is proline, $X_3$ is 0 or 2 amino acids. The abbreviation "RGDN-Tic" (SEQ ID NO: 31) includes all peptides encompassed by this formula.

The invention also provides, for example, a pharmacophore, abbreviated "RGDDV," (SEQ ID NO: 1) which is contained within a non-naturally occurring peptide comprising the sequence:

$$X_1X_2X_3X_4GD\ X_5X_6X_7X_8 \quad \text{(SEQ ID NO: 33)}$$

wherein $X_1$ is $R_1R_2N$ (wherein $R_1$ is an H or alkyl group and $R_2$ is an H, alkyl, $CH_3CO$, alkyl—CO or phenyl—CO group) or 0 to 10 amino acids, which can be protected by acetylation at the N-terminus; $X_2$ is 0 or 1 amino acid, which, when $X_2$ is one amino acid, can form a bridge with $X_7$; $X_3$ is 0, 1 or 2 amino acids, which when $X_3$ is two amino acids, the amino acids can be a pair consisting of Glu—Ala, Tyr—Ala, Arg—Ala, Ile—Gly, Glu—Pro, or a hydrophobic amino acid followed by a second amino acid such as Ile—Ala, Ile—Phe, (2-Nal)—Ala, Phe—Ala or Ala—Ala, or analogs or mimics thereof; $X_4$ is a positively charged amino acid such as Arg, Lys, homoArg, N—Me—Arg or analogs or mimics thereof; $X_5$ is an amino acid such as Asp, Glu, β-(1(2)H-tetrazol-5-yl)-alanine or analogs or mimics thereof such as the sulfonamide derivatives, Msa, Psa or Tfsa (see Example I.D.), which can form an ionic or similar interaction with an integrin receptor; $X_6$ is an amino acid such as Leu, Ile, Val, Thr, Nle or analogs or mimics thereof, which has an aliphatic side chain, or is an aliphatic non-natural amino acid that is hydrophobic such as t-BvG, Cha, Chg, Npg or phenylglycine; X, is a residue capable of forming a bond with a bridging amino acid of $X_2$, or with $X_3$ when $X_2$ is 0, or with $X_4$ when $X_2$ and $X_3$ are 0, to conformationally restrain the peptide; and $X_8$ is —$CONR_3R_4$ (wherein $R_3$ is an H or alkyl group and $R_4$ is an H or alkyl group) or —$COOR_5$ (wherein $R_5$ is an H or alkyl group) or 0 to 10 amino acids, which can be protected as an amide at the C-terminus. The abbreviation "RGDDV" (SEQ ID NO: 1) includes all peptides encompassed by this formula.

In another aspect, the present invention provides RGD-containing cyclic peptides having the following sequences: G-R-G-D-E-P-D-G (SEQ ID NO: 16); R-G-D-N-I-E-NH$_2$ (SEQ ID NO: 25); G-Pmc-R-G-D-C-A (SEQ ID NO: 34); G-Pen-G-R-G-D-N-Y-C-A (SEQ ID NO: 35); G-Pen-G-E-R-G-D-N-Y-C-A (SEQ ID NO: 36); G-Pen-A-A-R-G-D-V-P-C-A-NH$_2$ (SEQ ID NO: 37); G-Pen-E-L-R-G-D-G-W-C-NH$_2$ (SEQ ID NO: 38); G-Pen-G-F-R-G-D-E-P-C-NH$_2$ (SEQ ID NO: 39); K-Pen-G-F-R-G-D-E-P-C-R (SEQ ID NO: 40); K-Pen-G-F-R-G-D-D-P-C-R (SEQ ID NO: 41); Ac-Pen-A-A-R-G-D-Orn-P-C-NH$_2$(SEQ ID NO: 42); (Mpa)-R-G-D-(YOMe)-(t-BuG)-C-NH$_2$ (SEQ ID NO:43) and (Mpa)-R-G-D-(Cha)-(t-BuG)-C-NH$_2$ (SEQ ID NO:44) (underlined amino acid residues indicate the cyclic region of a peptide). In an additional aspect, the invention provides a linear peptide having the sequence: Ac-R-G-D-D-V-G-NH$_2$ (SEQ ID NO: 2). These and other peptides are useful for practicing the invention.

As used herein, the term "amino acid" is meant in its broadest sense to include naturally occurring proteogenic amino acids and imino acids as well as non-naturally occurring amino acids and imino acids and analogs and mimics thereof. As used herein, the term "proteogenic" indicates that the amino acid can be incorporated into a protein in a cell through well known metabolic pathways. In view of this broad definition of an amino acid, one skilled in the art would know that reference herein to an amino acid, unless specifically indicated otherwise, includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. For example, Tic is a conformationally constrained analog of Phe and a benzo-fused analog of Pro. Tic analogs include, for example, Idc, Dic, Oic, Tca, and 7-OMe-Tic (see FIG. 1 for structure and full names of Tic and Tic analogs). Other conformationally constrained amino acids are known in the art and include, for example, proline derivatives (Chung et al., *J. Org. Chem.* 55:270–275 (1990), which is incorporated herein by reference).

The choice of including an (L)- or a (D)-amino acid in an RGD peptide of the present invention depends, in part, on the desired characteristics of the peptide. For example, the incorporation of one or more (D)-amino acids can confer increased stability on the peptide in vitro or in vivo, above that provided by conformational constraint, and can allow the peptide to remain active in the body for an extended period of time. The incorporation of one or more (D)-amino acids also can increase or decrease the pharmacological activity of the peptide as determined, for example, using the assays described in Examples II and III, below, or other in vitro or in vivo assays for determining, for example, osteoclast binding to a matrix or osteoclast activity. The skilled artisan can determine the desirable characteristics required of an RGD peptide of the invention by taking into consideration, for example, the age and general health of a subject.

Increased stability of a disulfide bonded peptide of the invention also can be conferred by incorporating a hydrophobic amino acid residue such as phenylalanine at position $X_1$ or $X_8$ or both $X_1$ and $X_8$ in an RGDNTic (SEQ ID NO: 31) or RGDDV (SEQ ID NO: 1) pharmacophore as disclosed herein. The presence of such a residue can stabilize the disulfide bond against enzymatic degradation (see Bauer et al., *Life Sciences* 31:1133–1140 (1982)). For example, peptide 220 (see FIG. 2), which is within the RGDNTic (SEQ ID NO: 31) class of peptides, contains a phenylalanine residue at position $X_1$ and exhibits a relatively long half-life in serum. Methods for determining pharmacokinetic properties of a peptide of the invention such as half-life of a peptide in serum are routine in the art (see, for example, *Experimental and Surgical Technique in the Rat,* 2d ed., chapters 1, 2 and 3 (H. B. Waynforth and P. A. Flecknell; Academic Press Ltd., London 1992); *Applied Biopharmaceutics and Pharmacokinetics,* 3d ed., chapters 3–5 and 9 (L. Shargel and A. B. C. Yu; Appelton and Lange, USA 1993), each of which is incorporated herein by reference). In addition, the half-life of a peptide in a subject can be determined, for example, by high performance liquid chromatography (HPLC) of serum samples collected from the subject at various times following administration of the peptide. One skilled in the art would know how to select appropriate elution buffers for HPLC based on the physicochemical properties of a particular peptide.

The RGD peptides of the invention can be chemically synthesized using, for example, an automated synthesizer (see Example I). Selective modification of a reactive group such as an amino acid side chain or an N- or C-terminal group in a peptide can impart desirable characteristics to an RGD peptide of the invention. A peptide can be manipulated while still attached to the resin following chemical synthesis or after cleavage from the resin to obtain, for example, an N-terminal modified peptide such as the acetylated peptides disclosed herein (see Example I and FIGS. 2 and 3). Peptides also can be synthesized containing the C-terminal carboxy group or a C-terminal amide as described in Example I. A newly synthesized peptide can be purified using a method such as reverse phase HPLC (RP-HPLC), as described in Example I, or other methods of separation based on the size or charge of the peptide. Similarly, well known methods such as amino acid sequence analysis or mass spectrometry, as described in Example I, are available for characterizing the structure of the RGD peptide.

An RGD peptide of the invention can be constrained by various methods, including, for example, formation of a disulfide bond or a lactam bond between $X_7$ and one of either $X_2$, $X_3$ or $X_4$. Residues capable of forming a disulfide bond include Cys, Pen, Pmp, Pmc and Mpr (βMercaptopropionic acid) (see Table 1). Residues capable of forming a lactam bridge include Asp, Glu, Lys, Orn, α,β-diaminopropionic acid, γ-amino-adipic acid and m-(aminomethyl)benzoic acid. The RGD peptides disclosed herein can cyclize, for example, via a lactam bond, which can utilize a side chain group of $X_7$ to form a covalent attachment to the N-terminal amine of $X_2$ or $X_3$ (when $X_2$ is 0) or $X_4$ (when $X_2$ and $X_3$ are 0). In particular, $X_7$ in a lactam-bonded peptide can be an Asp or a Glu residue. Conformational constraint also can be effected by the choice of a residue such as proline that is incorporated into a peptide or by synthesis of a peptidomimetic having a particular conformation or by any other means known to one skilled in the art.

RGD peptides of the invention comprising an RGDNTic (SEQ ID NO: 31) pharmacophore or an RGDDV (SEQ ID NO: 1) pharmacophore are exemplified by peptides shown in FIGS. 2 and 3. The minimal elements of the cyclic RGD peptides of the invention include 1) a five amino acid pharmacophore such as the pharmacophores abbreviated RGDNTic (SEQ ID NO: 31) or RGDDV (SEQ ID NO: 1) and 2) a means of conformational restraint. Peptide 812 (Ac-CRGDS(Tic)C-NH$_2$; SEQ ID NO: 45) from the RGDNTic (SEQ ID NO: 31) pharmacophore group and peptide 386 (RGDDVE-NH$_2$; SEQ ID NO: 3) from the RGDDV (SEQ ID NO: 1) pharmacophore group exemplify RGD peptides that have these minimally essential elements and demonstrate activity (see FIG. 2). Peptides are referred to herein by a number, which can be shown either alone or preceded by the letters, TL (see, also, FIG. 2, numbers listed in the left hand column).

Peptides of the RGDNTic (SEQ ID NO: 31) pharmacophore group are characterized, in general, as having increased potency, whereas the peptides of the pharmacophore RGDDV (SEQ ID NO: 1) group generally have higher receptor selectivity. However, RGD peptides having both characteristics also were identified (see, for example, peptides 750, 487, 191 and 159; FIG. 2). As used herein, the term "potency" or "potent" means that a peptide of the invention is active at a relatively low concentration in the assays described in Examples II and III. A potent peptide of the invention can be identified, for example, using the assays described in Examples II and III.

As used herein, the term "selective" means that a peptide of the invention preferentially reduces or inhibits the migration or binding to a matrix of cells such as osteoclasts, which are involved in bone resorption, endothelial cells, which are involved in angiogenesis, or smooth muscle cells, which are involved in neointimal hyperplasia. Selectivity can be due, for example, to the ability of a peptide of the invention to bind to $\alpha_V\beta_3$ with greater affinity than it binds to other integrins. Thus, in addition to having selectivity, for example, for osteoclast binding to a matrix, a peptide of the invention also can display receptor selectivity and, therefore, more specifically alter receptor-mediated binding, for example, of an endothelial cell to a matrix or receptor-mediated migration or binding, for example, of a smooth muscle cell to a region of arterial injury. It is recognized that a peptide of the invention can specifically bind more than one integrin, yet still be considered selective because it does not non-specifically bind any integrin. Thus, a peptide such as TL940, which can specifically bind both the $\alpha_V\beta_3$ and the $\alpha_{IIb}\beta_3$ integrin receptors, is considered an example of a selective peptide that specifically binds two integrins.

As used herein, the term "receptor selectivity" means that a peptide of the invention can bind to one or more integrin receptors with greater affinity than it can bind to other receptors. Thus, a peptide of the invention is selective in that it specifically binds one or a few integrins, but does not non-specifically bind any integrin. For example, peptides such as peptides 487, 750, 368, 814, 191, 84 and 159 have a low IC50 value for $\alpha_V\beta_3$ binding as compared to $\alpha_V\beta_5$ binding or $\alpha_5\beta_1$ binding (see FIG. 2) and, therefore, are receptor selective for $\alpha_V\beta_3$. Methods for identifying a selective peptide are described in Example II.

Figure 13:
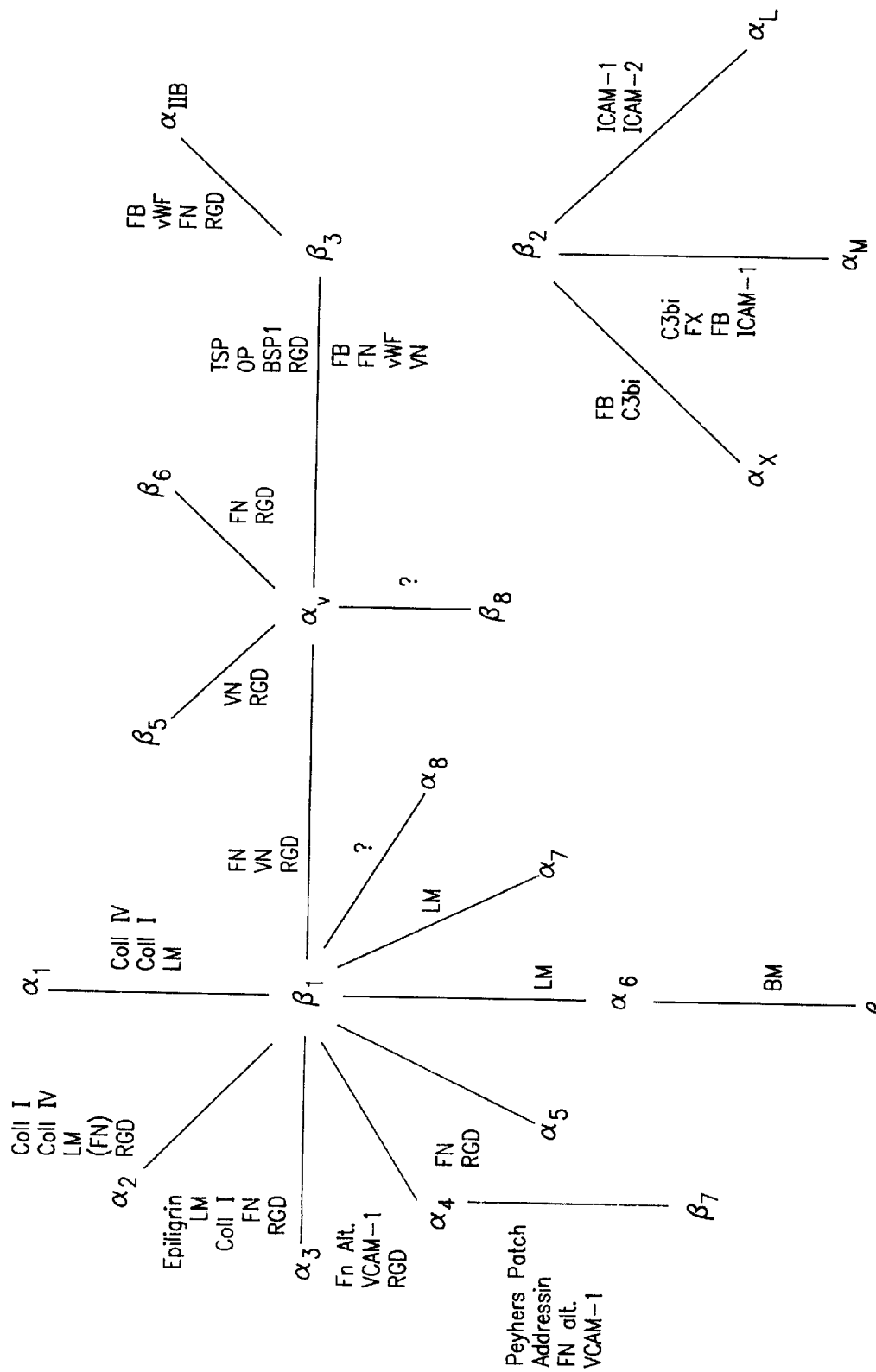
FIG. 13 presents the members of the integrin family. The known subunits, the subunit combinations that form the known integrins and the known ligands for these integrins are shown. The RGD specificity of those integrins that bind RGD also are shown. The more recently identified $\beta_6$ subunit tentatively has been assigned to the $\alpha_V$ group. FN, fibronectin; VN, vitronectin; FB, fibrinogen; LM, laminin; vWF, von Willebrand factor; COLL, collagen; OP, osteopontin; BSP1, bone sialoprotein 1; ICAM-1 and ICAM-2 are intercellular adhesion molecules; C3bi, complement component C3bi; Fn Alt, fibronectin alternatively spliced domain.

Integrins are heterodimeric molecules comprised of an α and a β subunit. The αβ integrin receptor binds to molecules in the extracellular matrix, commonly via the Arg—Gly—Asp sequence present in such molecules. Numerous α and β subtypes have been identified and the combination of a particular α subtype with a particular β subtype contributes to the ligand specificity of the integrin (see FIG. 13). Some integrins can adopt subtle conformational changes specific to a particular cell type, thus providing an additional level of cell type integrin specificity (Chuntharapai et al., *Exp. Cell Res.* 205:345–352 (1993)).

As used herein, the terms "matrix" and "ligand" are used in the broadest sense to mean a material to which a cell such as an osteoclast, an endothelial cell or a smooth muscle cell can bind to or migrate across. Cells can bind to or migrate across extracellular matrix components such as fibronectin, vitronectin, laminin and collagen. In addition, it is well known that osteoclasts, for example, can bind to bone and to bone matrix proteins such as osteopontin and bone sialoprotein.

As disclosed herein, osteoclasts also can bind, for example, to a matrix such as a serum-coated microtiter plate or to a plate having attached thereto an RGD peptide of the invention. In addition, an osteoclast can express specific integrin receptors on its cell surface and, therefore, can bind to a matrix component recognized by the receptor. For example, JY cells express $\alpha_V\beta_3$ integrin receptors and, accordingly, can bind a matrix such as vitronectin (see Example II). Vitronectin is a ligand of the $\alpha_V\beta_3$ receptor.

Vascular cells such as endothelial cells and smooth muscle cells also can migrate across and bind to a matrix such as the basement membrane region of blood vessels. Such interactions of endothelial cells and smooth muscle cells are involved, for example, in angiogenesis and restenosis. Angiogenesis, for example, is important for normal development and wound healing. In addition, however, angiogenesis is required for the growth of solid tumors and neovascularization serves as a conduit for metastasis. Anti-$\alpha_V\beta_3$ antibodies and relatively non-selective peptide antagonists for $\alpha_V\beta_3$ integrin receptor-mediated cell binding suppressed angiogenesis in tumors in the chick chorioallantoic membrane assay (Brooks et al., supra, 1994a; 1994b). These results indicate that $\alpha_V\beta_3$ integrin receptor-mediated binding is involved in the vascular cell adhesion to the extracellular matrix that occurs in angiogenesis.

The $\alpha_V\beta_3$ integrin receptor also is involved in the migration and binding of cells to a region of vascular injury such as occurs during restenosis. Of the approximately 350,000 angioplasties performed each year, restenosis occurs in greater than 30% of the treated patients within one year. A peptide that binds the $\alpha_V\beta_3$ receptor inhibited the neointimal hyperplasia that normally occurs following arterial injury in a rabbit model of atherosclerosis (Choi et al., supra, 1994). In addition, an anti-$\beta_3$ antibody reduced clinical restenosis (Topol et al., *Lancet* 343:881 (1994)). Since $\beta_3$ can associate with $\alpha_{IIb}$ as well as $\alpha_V$, more than one integrin can be involved in the vascular cell migration, binding and proliferation that results in restenosis.

Osteoclasts attach to bone matrix via integrin-type receptors present on the osteoclast cellular membrane. Integrin receptor-mediated osteoclast binding, for example, to bone matrix is involved in bone resorption. Since integrin receptor binding is involved in the interaction of cells with a matrix, a process such as bone resorption, angiogenesis or restenosis can be reduced or inhibited by reducing or inhibiting, for example, $\alpha_V\beta_3$ integrin receptor-mediated binding of a cell such as an osteoclast to bone matrix or of endothelial cell or smooth muscle cell to vascular matrix.

Osteoclasts can express an $\alpha_V\beta_3$ integrin receptor, as well as $\alpha_V\beta_1$ and $\alpha_2\beta_1$ integrin receptors (Nesbitt et al., *J. Biol. Chem.* 268:16737–16745 (1993)). $\alpha_V\beta_1$ is a fibronectin receptor. As discussed above, the $\alpha_V\beta_3$ integrin is a vitronectin receptor, which can be involved in bone resorption. For example, a monoclonal antibody against $\alpha_V\beta_3$ blocked bone resorption in vitro (Horton et al., *Exp. Cell Res.* 195:368–375 (1991)). The vitronectin receptor present on rat osteoclasts can bind a wide variety of RGD-containing extracellular matrix and bone proteins in vitro, including osteopontin and bone sialoprotein (Helfrich et al., *J. Bone Miner. Res.* 7:335–343 (1992); Reinholt et al., *Proc. Natl. Acad. Sci. USA* 87:4473–4475 (1990); Miyauchi, et al., *J. Biol. Chem.* 266:20369–20374 (1991)). The $\alpha_2\beta_1$ integrin interacts with collagen and laminin and may be involved in the sealing event necessary for resorption to occur (Horton et al., supra, 1991). An agent such as the RGD peptides of the invention, which can inhibit ligand binding to these and other integrins present on osteoclasts, is useful for disrupting the binding of osteoclasts to bone and, therefore, reducing or inhibiting the process of bone resorption.

As discussed above, the $\alpha_V\beta_3$ integrin receptor also is involved in angiogenesis and is required for neovascularization (Brooks et al., supra, 1994b). Antagonists of $\alpha_V\beta_3$ can disrupt newly forming blood vessels but do not affect preexisting vasculature. Systemic administration of $\alpha_V\beta_3$ antagonists can inhibit angiogenesis associated with tumor growth and metastasis and can cause regression of various histologically distinct human tumors (Brooks et al., supra, 1994a). As disclosed herein, the claimed peptides, including the RGDNTic (SEQ ID NO: 31) and RGDDV (SEQ ID NO: 1) pharmacophores, are useful for altering angiogenesis, which can be associated with a pathology such as cancer or retinopathy or with various inflammatory diseases (see, for example, Blood and Zetter, *Biochim. Biophys. Acta* 1032:88–118 (1990); Folkman, *Sem. Canc. Biol.* 3:65–71 (1992)). The peptides of the invention also can be useful for promoting neovascularization, for example, by immobilizing a peptide onto a desirable matrix, thus promoting adhesion and migration of migratory endothelial cells on the matrix. Although reference is made herein generally to endothelial cells, it should be recognized that the $\alpha_V\beta_3$ integrin receptor is expressed by migratory endothelial cells but not necessarily by all endothelial cells.

The $\alpha_V\beta_3$ integrin receptor also can be involved in the migration, binding and proliferation of smooth muscle cells at a site of arterial injury, resulting in a pathology characterized, for example, by the neointimal hyperplasia associated with restenosis of an artery following angioplasty. Antagonists of the $\alpha_V\beta_3$ integrin receptor, including, for example, an anti-$\alpha_V\beta_3$ antibody and the peptide G(Pen) GRGDSPCA, (SEQ ID NO: 46), can inhibit neointimal hyperplasia (Choi et al., supra, 1994). As disclosed herein, the RGD peptides of the invention can be useful for reducing or inhibiting restenosis and, in addition, can provide the advantage of having greater potency or selectivity or both as compared to G(Pen GRGDSPCA (SEQ ID NO: 46).

A $\beta_3$-containing integrin receptor such as the platelet $\alpha_{IIb}\beta_3$ integrin receptor also can be involved in restenosis (Topol et al., supra, 1994). Thus, a peptide of the invention such as TL200 or TL697, both of which selectively bind the $\alpha_{IIb}\beta_3$ integrin receptor, can be used alone or in combination with a peptide that selectively binds the $\alpha_V\beta_3$ integrin receptor to reduce or inhibit restenosis in a subject. In addition, a peptide of the invention such as TL940, which binds both the $\alpha_V\beta_3$ and $\alpha_{IIb}\beta_3$ integrin receptors, can be administered alone to a subject in order to reduce or inhibit restenosis in the subject.

The invention provides a method of reducing or inhibiting bone resorption, angiogenesis or restenosis in a subject, comprising administering an RGD peptide as disclosed herein. As used herein, the terms "reducing" and "inhibiting" have their common meanings. The terms are used together, here, to avoid any ambiguity as to the extent to which an RGD peptide of the invention acts. It is recognized that an RGD peptide can decrease, for example, the level of bone resorption below a level that is detectable using a particular assay. In this situation, one would be unable to determine whether the rate of bone resorption was reduced to a lower level or inhibited such that no resorption was occurring. The use of these terms together precludes the need to distinguish such events.

The peptides of the invention also can alter $\alpha_V\beta_3$ integrin receptor-mediated binding. As used herein, the term "alter"

is used in its broadest sense to indicate an increase or decrease in binding. For example, when present in solution, the peptides of the invention can decrease $\alpha_v\beta_3$ binding to a ligand by competing with the ligand for the integrin receptor. A peptide of the invention also can be attached to a solid substrate, which can increase binding of the $\alpha_v\beta_3$ receptor to the substrate. Thus, a peptide of the invention can be useful, for example, for altering angiogenesis in a tissue. For example, an endothelial cell can be contacted with a peptide of the invention, which can inhibit the binding of an endothelial cell to a matrix, thereby reducing or inhibiting angiogenesis. Alternatively, a peptide of the invention can be immobilized onto a matrix such that endothelial cells can bind to the matrix, thereby increasing angiogenesis in or around the matrix.

Integrin-ligand binding can be inhibited and binding can be disrupted by synthetic peptides comprising the RGD sequence (see, for example, U.S. Pat. No. 4,614,517 issued Sep. 30, 1986; U.S. Pat. No. 4,792,525 issued Dec. 20, 1988; U.S. Pat. No. 4,988,621 issued Jan. 29, 1991, each of which is incorporated herein by reference). RGD-containing peptides have been shown to block osteoclast adhesion in vitro (Horton et al., *J. Bone Miner. Res.* 8:239–247 (1993)). Echistatin is a natural RGD-containing protein that is isolated from snake venom. Echistatin binds to osteoclasts in a nonselective manner and inhibits bone resorption in vitro (Sato et al., *J. Cell Biol.* 111:1713–1723 (1990); EP 437,367) and in vivo (Fisher et al., *Endocrinology* 132:1411–1413 (1993).

The potency and selectivity of an RGD peptide toward an integrin receptor can be improved by restricting the number of conformations the peptide can adopt (Pierschbacher and Ruoslahti, *J. Biol. Chem.* 262:17294–17298 (1987); WO 89/05150). Conformational restraint of a peptide can be induced by various means including, for example, cyclization. The concept of using cyclic RGD peptides, modeled after echistatin, to inhibit osteoclast attachment to bone has been broadly described (EP 437,367), and osteoclast attachment inhibiting activities of several cyclic RGD peptides have been reported (Bertolini et al., In *13th Ann. Mtg. Am. Soc. Bone Miner. Res.,* abstract 252 (1991); Horton et al., supra, 1993).

In one aspect, an RGD peptide useful as a therapeutic for unwanted bone resorption, angiogenesis or restenosis is receptor selective in targeting only the one or few integrins involved in bone resorption, angiogenesis or restenosis, respectively, and not others. As a result, an RGD peptide of the invention can preferentially inhibit, for example, the binding of osteoclasts, as compared to other cell types, to bone. In another aspect, a therapeutically useful RGD peptide is potent and, therefore, effective at a relatively low dose. A peptide having both potency and selectivity is particularly useful for reducing or inhibiting bone resorption. In comparison, a peptide such as TL940 that is potent but can bind both $\alpha_v\beta_3$ and $\alpha_{IIb}\beta_3$ receptors can be useful for reducing or inhibiting restenosis. The present invention provides RGD peptides having one or more of these characteristics and provides methods for evaluating RGD peptides to identify selective and potent peptides and methods of using the RGD peptides of the invention to inhibit bone resorption, angiogenesis or restenosis.

The present invention also provides a series of in vitro and in vivo assays useful for screening a panel of peptides in order to identify peptides that can reduce or inhibit bone resorption or that can alter integrin binding such as $\alpha_v\beta_3$ integrin receptor-mediated binding. Such peptides can include, for example, peptides within the pharmacophore groups exemplified herein or peptides within other pharmacophore groups. The series of assays disclosed herein is particularly useful for determining the selectivity and potency of a peptide for reducing or inhibiting bone resorption. The selectivity of a peptide for an integrin receptor involved in osteoclast binding to bone can be determined, for example, using the integrin receptor assays and cell attachment and detachment assays described herein. Use of cell-based assays in conjunction with receptor-based assays is informative because the receptor ELISAs provide useful information regarding the binding characteristics of a particular peptide toward a particular integrin and because the cell-based assays confirm that those characteristics are relevant to the $\alpha_v\beta_3$ receptor or to bone resorption.

A peptide that selectively binds an integrin receptor involved in osteoclast binding to bone and that causes detachment of osteoclasts, but not other cell types, can be identified as a selective peptide and can be further examined for its potency by comparing the IC50 value of the peptide with other peptides. Thus, the disclosed series of assays provides a means for identifying a potent and/or selective peptide, which can reduce or inhibit bone resorption or alter $\alpha_v\beta_3$ binding.

A potent or selective RGD peptide can be administered to a subject such as a human in order to reduce or inhibit bone resorption, angiogenesis or restenosis in the subject. With regard to bone resorption, the subject has a pathology that is characterized by an undesirable balance of bone resorption as compared to bone formation, resulting in excessive bone resorption. An elderly person suffering from osteoporosis is an example of a subject having such a pathology. Other relevant pathologies include, for example, Paget's disease, osteoclastoma and the pathological loss of bone that occurs in an astronaut during a space mission or in a person exposed to a minimal gravity environment. Furthermore, bone loss can occur in a bone that is immobilized in a cast, in a subject restricted to a prolonged period of bed rest and in a subject undergoing kidney dialysis. Administration of an RGD peptide of the invention can reduce or inhibit the rate of bone resorption in each of these subjects. Thus, the peptides of the invention are particularly useful as medicaments, wherein administration of such a peptide to a subject can decrease the amount of bone loss, angiogenesis or restenosis in the subject.

An $\alpha_v\beta_3$ selective peptide of the invention also can be useful in a pathology such as cancer, provided the cancer cell, for example, expresses the $\alpha_v\beta_3$ integrin. Administration of a peptide of the invention to a subject having such a pathology can inhibit attachment of the $\alpha_v\beta_3$ integrin-containing cell to extracellular matrix proteins or other relevant ligands involved in tumor cell metastasis (Nip et al., *J. Clin. Invest.* 90:1406–1413 (1992); Gladson and Cheresh, *J. Clin. Invest.* 88:1924–1932 (1991), each of which is incorporated herein by reference). Peptides of the invention that can inhibit $\alpha_v\beta_3$ integrin binding to a ligand and, thus, can be effective in treating a pathology such as cancer are evaluated using methods known in the art and described, for example, by Hardan et al., *Intl. J. Canc.* 55:1023–1028 (1993); Murthy et al., *Clin. Expt. Metast.* 10:39–47 (1992); and Komazawa et al., *Clin. Expt. Metast.* 11:482–491 (1993), each of which is incorporated herein by reference.

The $\alpha_v\beta_3$ integrin also is involved in the binding of endothelial cells to von Willebrand factor (VWF). This binding is necessary for maintaining the integrity of the blood vessel wall and permitting new blood vessel formation and blood vessel wall repair (Denis et al., *Blood* 82: 3622–3630 (1993)). $\alpha_v\beta_3$ receptor selective peptides can be used to strengthen attachment of endothelial cells to vessel walls or to inhibit the interaction of an endothelial cell and VWF. Similarly, angiogenesis depends on interactions between endothelial cells and $\alpha_v\beta_3$ integrins (Brooks et al., supra, 1994a). Pathologies such as diabetic retinopathy, rheumatoid arthritis and cancer can result due to pathologies affecting these interactions. Thus, peptides that are selective for binding to the $\alpha_v\beta_3$ integrin can bind $\alpha_v\beta_3$ and block its binding to a ligand. Such selective binding by a peptide of the invention can provide a means of treating an $\alpha_v\beta_3$-related pathology, including, for example, the restenosis that occurs in an arterial wall following angioplasty or the angiogenesis that occurs during growth and metastasis of a tumor.

Peptides selective for binding to $\alpha_v\beta_3$ also can affect binding to the $\alpha_{IIb}\beta_3$ integrin, which is involved in platelet aggregation. For example, the peptide RGD(YOMe)RE-NH$_2$ (SEQ ID NO: 47) (TL940; see FIG. 2) has an IC50 value of 0.0042 $\mu$M in an $\alpha_v\beta_3$ ELISA and is highly potent at inhibiting platelet aggregation (IC50=0.82 $\mu$M). Thus, an $\alpha_v\beta_3$ selective peptide also can be useful, for example, for treating a pathology such as restenosis, which involves the $\alpha_{IIb}\beta_3$ receptor (Choi et al., supra, 1994; Topol et al., supra, 1994). Similarly, peptide ligands for the $\alpha_{IIb}\beta_3$ receptor can be useful for inhibiting bone resorption or for reducing or inhibiting restenosis. Assays useful for evaluating the reactivity of a peptide with $\alpha_{IIb}\beta_3$, including whether the peptide can inhibit platelet aggregation, are known in the art and described herein and, for example, in International Publication No. WO91/15515, published Oct. 17, 1991, which is incorporated herein by reference.

The in vitro assays disclosed in Example II also can be used to identify receptor selective peptides of the invention that have various specific in vitro and in vivo utilities. For example, a receptor selective peptide of the invention can be immobilized on a supporting matrix such as a natural or synthetic surface. Such a peptide coated surface can be useful for separating in vitro a population of cells that express a specific receptor from cells that do not express the receptor. For example, a peptide that selectively binds $\alpha_v\beta_5$ but not $\alpha_5\beta_1$ or $\alpha_v\beta_3$ can be used to isolate a population of normal articular chondrocytes, which primarily express $\alpha_v\beta_5$ integrin receptors, from cells that express $\alpha_v\beta_3$ and/or $\alpha_5\beta_1$ integrins. A peptide coated matrix can be produced by immobilizing the peptide on the matrix, for example, through a covalent or non-covalent bond or other interaction such that the peptide is associated with the matrix.

Various receptor selective peptides are disclosed herein or can be identified using the methods in Example II. For example, peptides 159, 487 and 750 have higher affinity for $\alpha_v\beta_3$ than for $\alpha_v\beta_5$ and $\alpha_5\beta_1$. Thus, peptides 159, 487 and 750 can bind with greater affinity to a cell such as an osteoclast, which expresses $\alpha_v\beta_3$ as compared to a cell that expresses $\alpha_v\beta_5$ and $\alpha_5\beta_1$ receptors. In comparison, peptides 100, 825, 390 and 310 are more selective toward $\alpha_5\beta_1$ than toward $\alpha_v\beta_5$ and can be useful to isolate a population of cells expressing an $\alpha_5\beta_1$ receptor.

The receptor selectivity of a peptide of the invention also can be used advantageously in vivo. For example, a peptide coated matrix as described above can be implanted into a subject in order to facilitate localization of cells expressing a specific integrin receptor at the implant site. For example, peptide 214 as described above can be useful for inducing the localization of osteoclasts at a site of bone hypertrophy as occurs in a pathology, such as osteopetrosis or senile ankylosing hyperostosis of the spine, or can be useful for inducing angiogenesis, for example, when performing natural or artificial vascular grafts or dermal replacements. Thus, a peptide of the invention can be useful for increasing angiogenesis where such angiogenesis is otherwise insufficient. In addition, peptides 100, 825, 390 and 310, as described above, can be useful for inducing $\alpha_5\beta_1$-mediated fibronectin matrix assembly, for example, in a wound. If desired, the peptides of the invention can be administered to a subject in soluble form and, therefore, can be useful for preventing $\alpha_5\beta_1$-mediated fibronectin matrix assembly in a wound in order to prevent, for example, excessive scarring. Thus, the receptor selectivity of the disclosed peptides as shown, for example, in FIG. 2 defines various utilities for the specific peptides.

An RGD peptide of the invention also can be used to reduce or inhibit angiogenesis under conditions where the occurrence or amount of angiogenesis is inappropriate. As used herein, the term "inappropriate" when used in reference to angiogenesis means an unwanted or excessive growth of blood vessels. For example, tumor growth is dependent, in part, on angiogenesis, which facilitates nutrient transport to the proliferating tumor cells. Such angiogenesis is unwanted from a clinical perspective and, therefore, inappropriate as defined herein. In addition, a pathology can be associated with excessive angiogenesis, in which a case a peptide of the invention can be useful for reducing or inhibiting angiogenesis. Thus, an objective of the present invention is to provide an RGD peptide of the invention to a subject having a pathology characterized, in part, by inappropriate angiogenesis for the purpose of reducing or inhibiting such angiogenesis.

The invention provides pharmaceutical compositions comprising an RGD peptide of the invention, which can reduce or inhibit bone resorption, angiogenesis or restenosis or alter $\alpha_v\beta_3$ binding, and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters. A peptide of the invention also can be encapsulated within a biodegradable or non-biodegradable polymer.

A pharmaceutically acceptable carrier can contain physiologically acceptable compounds that act, for example, to stabilize an RGD peptide of the invention or to increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the RGD peptide and on the particular physicochemical characteristics of the specific peptide.

A pharmaceutical composition comprising an RGD peptide of the invention can be useful for ameliorating the severity of a pathology characterized, in part, by the involvement of $\alpha_v\beta_3$ integrin receptor-mediated binding of a cell. Such pathologies are manifested, for example, by an undesirable level or occurrence of bone resorption, angiogenesis, neointimal hyperplasia or restenosis in a subject, wherein the undesirable level can be undesirably high or undesirably low. For example, a pathology such as osteoporosis or cancer is characterized, in part, by undesirably high levels of bone resorption or angiogenesis, respectively. In these cases, an objective of the present invention is to decrease $\alpha_v\beta_3$ integrin receptor-mediated binding of a cell to a matrix. In addition, a pathology can be characterized, in part, by an undesirably low level, for example, of bone resorption and, therefore, an objective would be to increase osteoclast binding to the bone matrix by coating the matrix with an RGD peptide of the invention. Thus, the term "pathology" is used broadly herein to include any condition characterized, in part, by an undesirable level of bone resorption, angiogenesis or restenosis. The present invention provides compositions and methods for ameliorating the severity of such a pathology. As used herein, the term "ameliorate" has its commonly known meaning of "make better," "improve," "alleviate" or "relieve."

A peptide of the invention can be administered, for example, to a subject suffering from a pathology such as osteoporosis, which is characterized, in part, by bone resorption, or a pathology such as cancer, which is characterized, in part, by angiogenesis of the growing tumor, wherein such administration can ameliorate the severity of the pathology. Similarly, an RGD peptide of the invention can be administered to a subject treated by angioplasty in order to ameliorate the severity of restenosis, which can be a pathologic response to angioplasty.

A peptide of the invention also can be administered to a subject experiencing, for example, abnormal bone growth, in which case the RGD peptide can be used to increase the $\alpha_v\beta_3$ integrin receptor-mediated binding of osteoclasts to the bone by coating the bone matrix with an RGD peptide of the invention such that the peptide is immobilized on the matrix. In addition, a peptide of the invention that is selective for $\alpha_5\beta_1$ binding can be useful, for example, for treating osteoporosis by immobilizing such peptides to a bone surface in order to promote adhesion of osteoblasts, which are involved in bone formation, to the bone surface. In view of the present disclosure, other uses for the RGD peptides of the invention would be known to those skilled in the art and are described, for example, by Grzesik and Robey, *J. Bone Min. Res.* 9:487 (1994). Furthermore, it is recognized that a peptide of the invention can be useful in a soluble form, in which case it can interfere with the binding of an $\alpha_v\beta_3$-containing cell with a matrix, or can be useful when immobilized on a matrix, in which case it can mediate the binding of an $\alpha_v\beta_3$-containing cell to the coated matrix.

One skilled in the art would know that a pharmaceutical composition comprising an RGD peptide of the invention can be administered to a subject having a pathology characterized, in part, by bone resorption, angiogenesis or restenosis by various routes including, for example, orally or parenterally, such as intravenously, intramuscularly, subcutaneously or intraperitoneally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or solution, or active, for example, using a nasal spray or inhalant. A pharmaceutical composition comprising an RGD peptide of the invention also can be administered as a topical spray, in which case one component of the composition can be an appropriate propellant. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In order to ameliorate the severity of a pathology characterized, in part, by bone resorption, angiogenesis or restenosis in a subject or to alter $\alpha_v\beta_3$ or other integrin binding, an RGD peptide of the invention must be administered in a therapeutically effective amount, which is about 0.01 to 100 mg/kg body weight/day. As used herein, the term "therapeutically effective amount" means an amount of a peptide that can ameliorate the severity of a pathology characterized, in part, by bone resorption, angiogenesis or restenosis in a subject.

A therapeutically effective amount of a peptide can be determined using methods known to those in the art, including the methods described in Examples II and III, below. A therapeutically effective amount of a peptide can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of an RGD peptide of the invention required to obtain a therapeutically effective amount in a subject depends on many factors including the age and general health of the subject as well as the route of administration and the number of treatments to be administered. In view of these factors, the skilled artisan would adjust the particular dose so as to obtain a therapeutically effective amount for ameliorating the severity of a pathology characterized, in part, by bone resorption, angiogenesis or restenosis in a subject.

An RGD peptide of the invention is useful for reducing or inhibiting osteoclast binding to a matrix in vitro. As generally described in U.S. Pat. Nos. 4,614,517, 4,792,525 and 4,988,621, supra, RGD-containing peptides in solution bind to integrins that are expressed on the surface of a cell and either prevent the cell from attaching to a matrix or effect detachment of the cell from a matrix. In addition, when RGD-containing peptides are coated onto a surface, a cell that expresses an integrin reactive with the peptide can bind to the surface. Thus, the peptides of the invention can be used to alter the ability of a cell expressing an integrin to attach to a solid matrix such as a tissue culture plate, a prosthetic device or an artificial extracellular matrix (see, for example, WO 90/06767, which is incorporated herein by reference). Since peptides of the invention also can demonstrate receptor selectivity, they are particularly useful for inhibiting the binding of a cell expressing the integrin to such a matrix.

The following examples are intended to illustrate but not limit the present invention.

EXAMPLE I

Synthesis of RGD Peptides

This example provides methods for chemically synthesizing the RGD peptides of the invention.

A. Synthesis of Cyclic Peptides Having Disulfide Bonds

Peptides were synthesized by the solid-phase method utilizing an automated synthesizer (Applied Biosystems, Inc. Model 431A) (see Steward and Young, In Solid Phases Peptide Synthesis, 2nd ed. (Pierce Chemical Co., Rockford, Ill., 1984), which is incorporated herein by reference). Peptides having a C-terminal amide were synthesized using p-methylbenzhydrylamine (pMBHA) resin. Peptides having a C-terminal acid were synthesized using chloromethylated resin. Peptides having an N-terminal acetyl group were acetylated using a mixture of acetic anhydride (20 eq) and diisopropylethylamine (20 eq) in N-methylpyrrolidone.

N-terminal tertbutyloxycarbonyl (Boc) protection was employed for all amino acids. Boc—Arg(Tos)—OH, Boc—Asp(OcHx)—OH, Boc—Cys(4-MeBzl)—OH, Boc—Gly—OH, Boc—Hpa—OH, Boc—Lys(CZ)—OH, Boc—Pen(4-MeBzl)—OH, Boc—(D)Pen(4-MeBzl)—OH, Boc—Pro—OH, Boc—Tic—OH, Boc-7-OMe—Tic and Boc—Tyr(Me)—OH were purchased from Bachem Inc. (Torrance, Calif.). The following compounds were synthesized using the methods described in the indicated references: Boc—Idc—OH (Sancy, In *Organic Syntheses* 63:160–170 (1984)); Boc—Dic—OH (Martin et al., EP 432,695); Boc—OiC—OH (Vincent et al., *Tetr. Lett.* 23:1677–1680 (1982)); and Boc—Tca—OH (Yabe et al., *Chem. Pharm. Bull.* 26:993–997 (1978), each of which is incorporated herein by reference). Mamb (m-(aminomethyl) benzoic acid) was prepared as described by Jackson et al. (*J. Am. Chem. Soc.* 116:3220–3230 (1994), which is incorporated herein by reference) and was incorporated into a peptide using an oxime resin. Dicyclohexylcarbodiimide and hydroxybenzyltriazole were used in the coupling reactions. The extent of the reactions was monitored using the standard ninhydrin test.

Following synthesis, the peptides were removed from the resin and deprotected by adding anhydrous hydrogen fluoride (HF; 10 ml/g of resin-bound peptide) containing anisole (1 ml/g) at 0° C. for 60 min. The HF was removed by evaporation and the residue was washed with anhydrous ether. The crude peptides were extracted with water or 15% aqueous acetic acid and the aqueous fractions were combined and lyophilized. Peptides were purified and characterized as described below.

The crude acyclic peptide was dissolved in 0.1M ammonium bicarbonate (0.5 mg/ml) and stirred uncovered. The course of the reaction was monitored by HPLC. After cyclization was complete (several hours to several days), the solution was filtered and the peptides were purified and characterized as described below.

B. Synthesis of Cyclic Peptides Having Lactam Bridges

Cyclic peptides having a lactam bridge were synthesized as outlined herein. The protected peptide resin was synthesized using the PMBHA resin. The lactam bridge was formed while the peptide was on the resin using the method described by Felix et al., *Int. J. Pept. Prot. Res.* 31:231 (1988) and by Felix et al., *Int. J. Pept. Prot. Res.* 32:441 (1988), each of which is incorporated herein by reference.

Essentially, the method of Felix et al. uses $N^\alpha$—Boc-amino acids together with 9-fluorenylmethyl ester (OFm) side-chain protection. Asp and Glu were introduced using Boc—Asp(OFm)—OH and Boc—Glu(OFm)—OH. After coupling the final amino acid, OFm protecting groups were selectively removed by treating the peptide resin with 50% piperidine in dimethylformamide for 1 hr. The peptide resin was washed with 3×40 ml dichloromethane and mixed with a 6-fold excess of BOP reagent (benzotriazol-1-yl-oxy-tris-(dimethylamino)phosphonium hexafluorophosphate) in the presence of an 8-fold excess of diisopropylamine for 5 hr. Coupling reactions were repeated until the resin gave the negative ninhydrin test.

After the cyclization reaction was complete, peptides were removed from the resin and deprotected using anhydrous HF (10 ml/g of resin-bound peptide) containing anisole (1 ml/g) at 0° C. for 60 min. The HF was removed by evaporation and the residue was washed with anhydrous ether. The crude peptides were extracted with water or 15% aqueous acetic acid and the aqueous fractions were combined and lyophilized and purified and characterized as described below.

C. Purification and Characterization of the Peptides

The crude peptides were purified via preparative RP-HPLC on a $C_{18}$ silica gel column "WATERS DELTA-PAK" Column, 15 μm, 300A, 47×300 mm) eluting with a linear acetonitrile gradient (0–30%) with a constant concentration of trifluoroacetic acid (TFA; 0.1%, v/v) over 30 min at a flow rate of 40 ml/min. The purified peptides were analyzed by analytical RP-HPLC using a C-18 column (Vydac, 5 μm, 300A, 4.5×250 mm). The purified peptides were recovered by lyophilization of the HPLC fractions and were at least 95% pure. For analytical HPLC, a binary solvent system, water containing 0.1% TFA and acetonitrile containing 0.1% TFA as the organic modifier, was used. The solvent programs involved linear gradients as follows: (1) 10–45% acetonitrile over 35 min with a flow rate of 1.5 ml/min and (2) 0–70% acetonitrile over 30 min with flow rate of 1.5 ml/min.

In some cases, the peptide was adjusted to a neutral pH and potassium ferricyanide was added to the TFA peptide to minimize polymerization that might result due to the presence of the reducing agent. The potassium ferricyanide was removed by ion exchange chromatography and the peptides were lyophilized. The presence of thiol reducing agents, which indicates the need to add potassium ferricyanide, can be detected using Ellman's test (*Arch. Biochem. Biophys.* 82: 70 (1959), which is incorporated herein by reference).

To confirm the correct amino acid sequences as shown in FIGS. 2 and 3 were synthesized, the peptides were characterized by fast atom bombardment mass spectroscopy and by amino acid analysis. Amino acid analysis was performed on a Pickering Labs-Trione amino acid analyzer that was equipped with spectra-physics UV detector. Hydrolysis of peptide samples for amino acid analysis was performed on 1 mg samples with 1 ml constant oiling 6N HCl. Samples were degassed, sealed under vacuum nd heated for 24 hr at 110° C.

D. Synthesis of β-[(methylsulfonyl)amino]alanine

This example describes the synthesis of β[(methylsulfonyl)amino]alanine (Msa). Psa and Tfsa were synthesized according to the same procedure, except that methanesulfonylchloride was replaced with phenylsulfonylchloride for synthesis of Psa and with trifluoromethylsulfonylchloride for synthesis of Tfsa.

Msa was synthesized using the general procedure of Krchnak et al., *Collection Czechoslov. Chem. Comm.* 44:2161–2164 (1979), which is incorporated herein by reference). To a stirred solution of $N^\alpha$-tertbutyloxy carbonyl-α,β-diaminopropionic acid (700 mg, 3.43 mmol) in 1 N NaOH (34 ml) was added a solution of methanesulfonyl chloride (530 μl, 6.86 mmol) in acetone (30 ml).

After 1 hr, the reaction was extracted 2× with ether and acidified to pH 2 using 1 N HCl. The aqueous phase was extracted 3× with ethyl acetate and the combined organic phases were dried ($MgSO_4$) and concentrated to produce an oil. Msa was purified by silica gel chromatography using ethyl acetate/ethanol/acetic acid (95.8:4:0.2) as eluant. 300 mg Msa was obtained and was used in the standard solid phase peptide synthesis protocol. $^1$H-NMR analysis: (MeOH, $D_4$; 300 MHz) 4.2 ppm; (m, 1H). 3.3–3.6 ppm; (m, 2H). 2.95 ppm; (s, 3H). 1.4 ppm (s, 9H).

EXAMPLE II

RGD Peptide Activity In Vitro

This example describes a series of assay useful for determining the activity of an RGD peptide for inhibiting bone resorption, including inhibiting the binding of an osteoclast to a matrix in vitro.

A. Preparation of Assay Reagents

1. Isolation of Human Vitronectin

Human plasma was clotted by adjusting the sample to 20 mM $CaCl_2$, then stirring for 1 hr at room temperature (RT), followed by 2 hr at 4° C. The plasma was fractionated by centrifugation at 3000 rpm for 15 min ("SORVALL" centrifuge with GS3 rotor) and the supernatant was retained.

The supernatant was adjusted to 1 mM phenylmethylsulfonyl fluoride (PMSF)/5 mM EDTA. A column containing 75 ml "SEPHAROSE CL-4B" (beaded agarose) (Pharmacia; Piscataway N.J.) was equilibrated using five column volumes (5 vol) phosphate buffered saline (PBS), the supernatant was added and the flow-through fraction was collected. The flow-through fraction was applied to a column containing 50 ml heparin- "SEPHAROSE" (beaded agarose) which was made by swelling heparin-"SEPHAROSE CL-6B" (beaded agarose) (Pharmacia) with PBS for 5 min in a sintered glass funnel, then washing with PBS for 15 min. The heparin-"SEPHAROSE" (beaded agarose) was poured into a column, washed with 3 vol Buffer B (5 mM EDTA, 2M NaCl, 10 mM sodium phosphate, pH 7.7) and equilibrated with 5 vol PBS. The dye-colored flow-through fraction was collected, solid urea was added to a final concentration of 8M and the sample was incubated with stirring for 2 hr at RT.

The heparin "SEPHAROSE" (beaded agarose) column was washed with at least 3 vol Buffer C (5 mM EDTA, 8M urea, 10 mM sodium phosphate, pH 7.7, 10 mM 2-mercaptoethanol, 2M NaCl) and equilibrated with 5 vol Buffer A (5 mM EDTA, 8M urea, 10 mM sodium phosphate, pH 7.7). The flow-through fraction from above was loaded onto the column. The column was washed with 3 vol Buffer A, followed by 3 vol Buffer A containing 140 mM NaCl and by 1 vol Buffer A containing 140 mM NaCl/10 mM 2-mercaptoethanol. After 2 hr, the column was washed with 3 vol of the same final buffer.

Vitronectin (Vn) was eluted using Buffer D Buffer A containing 0.5M NaCl). The fractions were evaluated by 8% sodium dodecyl sulfate polyacrylamide gel electrophoresis (SDS-PAGE) under non-reducing conditions. The presence of Vn was confirmed by identifying the characteristic 65 kilodalton (kDa) and 75 kDa bands. In some instances, Vn was confirmed by western blot analysis using a specific anti-Vn antibody (8Eb; Hayman et al., *Proc. Natl. Acad. Sci., USA* 80:4003–4007 (1983), which is incorporated herein by reference). Western blot analysis was performed using a standard method as described, for example, by Sambrook et al., *Molecular Cloning: A laboratory manual* (Cold Spring Harbor Laboratory Press 1989), which is incorporated herein by reference.

2. Isolation of Human Fibronectin

Frozen human plasma was thawed at RT, then adjusted to 100 μM PMSF. The plasma was fractionated by centrifugation at 3000 rpm for 15 min in a "SORVALL" centrifuge (GS3 rotor) and the supernatant was collected.

A column containing 300–500 ml "SEPHAROSE-4B" (beaded agarose) was equilibrated with 1 l Buffer E (8 g KCl, 8 g $KH_2PO_4$, 320 g NaCl, 86.8 g $NaH_2PO_4$ per liter). The plasma supernatant was added to the column and the flow-through was collected from the time the yellow-colored plasma enters the "SEPHAROSE" (beaded agarose) until the time the eluate became clear. Two vol Buffer E were added to the column as a wash buffer to "push" the plasma through the column.

A column containing 50 ml gelatin "SEPHAROSE-4B" (beaded agarose) was prepared in a Kontes column and equilibrated with 500 ml Buffer E. The flow-through from the "SEPHAROSE-4B" (beaded agarose) column was loaded at a rate of 2 ml/min or slower. The column was washed with 500–1000 ml Buffer E or until $OD_{280}$ was below 0.10.

Three to five vol Buffer F (0.05M Tris, 4.5M urea, pH 7.0) were used to elute plasma fibronectin (Fn). One-quarter column vol fractions were collected and evaluated by 8% SDS-PAGE under reducing conditions. The presence of Fn was confirmed by identifying the characteristic band migrating at approximately 210–250 kDa. In some cases, the presence of Fn was confirmed by western blot analysis using a specific anti-Fn antibody (3E1; Pierschbacher et al., *Cell* 26:259–267 (1981), which is incorporated herein by reference).

Peak fractions containing Fn were pooled and the optical density was measured. If necessary, the pooled fraction was diluted until an $OD_{280}$ reading corresponding to 1 mg/ml Fn was obtained. The sample then was dialyzed against PBS and stored at –20° C. in PBS in a non-frost free freezer.

3. Preparation of 110 kDa Fibronectin Fragment

Fibronectin was purified as described above and dialyzed against 3 changes of 100 vol Buffer G (0.05M Tris, 0.3M NaCl, pH 8.3–8.5). The urea concentration decreased to below 0.1M.

Chymotrypsin was added at a concentration of 0.001 mg chymotrypsin/mg Fn. The digestion mixture was incubated overnight at 4° C. with gentle rocking. The presence of complete digestion was confirmed by SDS-PAGE analysis of pre- and post-digestion samples. The digested Fn sample was dialyzed against 2 changes of 100 vol Buffer H (0.1M $NaHCO_3$, 0.5M NaCl, pH 8.0). The pH of the dialyzed digest was between pH 8–9.

4. Purification of Human $\alpha_V\beta_5$ Vitronectin Receptor (VnR)

Human placenta was homogenized and washed on ice in 225 ml of Tris-buffered saline (TBS; pH 7.4–7.5; 4° C.), then fractionated by centrifugation at 3000 rpm for 15 min at 4° C. The supernatant was discarded and the pellet was extracted with 225 ml TBS containing 100 mM octyl-glucopyranoside (OG). Extraction was performed at 4° C., on ice, for 30 min, with stirring every 10 min. The extract was fractionated by centrifugation at 3000 rpm for 20 min and the supernatant was collected. The supernatant, which contained the $\alpha_V\beta_5$ Vn receptor (VnR), was adjusted to 3 mM $CaCl_2$.

Two tandem Kontes (Fisher Scientific) columns were prepared using equal volumes of "SEPHAROSE" (beaded agarose) 4B or 6B. Both columns were equilibrated with 10 vol cold (4° C.) Buffer I (1X TBS, pH 7.4, 50 mM OG, 3 mM $CaCl_2$, 20 μg/ml PMSF). One column contained Vn (Vn column) and was prepared as follows. Vn was dialyzed against 2 to 3 changes of coupling buffer (0.1M NaHCO$_3$, 0.5M NaCl, pH 8.3). CnBr-"SEPHAROSE" (beaded agarose) was swelled in 1 mM HCl, washed with coupling buffer, then combined with Vn. Coupling proceeded for 2 hr at RT or overnight at 4° C., followed by blocking with 1M ethanolamine or 0.2M glycine (pH 8.0) for 2 hr at RT.

The filtered, calcium supplemented placental extract was loaded onto the "SEPHAROSE" (beaded agarose) column, then run through the Vn column at 4° C. The flow-through was collected in a polypropylene container for disposal. The Vn column was washed with 5 vol cold (4° C.) Buffer I, allowed to equilibrate to RT, then washed with another 5 vol Buffer I at RT. The column was slowly eluted with 3 vol Buffer J (1X TBS, pH 7.4, 50 mM OG, 100 μg/ml GRGDSP (SEQ ID NO: 4) peptide, 20 μg/ml PMSF). Fractions were collected and evaluated by 8% SDS-PAGE under non-reducing conditions. Fractions showing bands migrating at the characteristic 150, 145 and 90 kDa molecular mass of the VnR were pooled, dialyzed against TBS (pH 7.5) containing 50 mM OG/3 mM CaCl$_2$ and concentrated using an "AMICON YM 30" filter.

5. Purification of Human $\alpha_5\beta_1$ Fibronectin Receptor (FnR)

Fibronectin receptor (FnR) was purified from 100 mM octyl-glucopyranoside-extracted human placenta. The procedure for purifying the FnR was the same as described for purifying the VnR through the initial "SEPHAROSE" (beaded agarose) chromatography step. Then, for purifying the FnR, the Sepharose 4B column flow-through was adjusted to 3 mM Mn$^{2+}$ and the resulting solution was fractionated using affinity chromatography on columns containing a GRGDSPK (SEQ ID NO: 5) peptide and the 110 kDa fibronectin fragment. Column washes and elutions were the same as described for purifying VnR, except that MnCl$_2$ rather than CaCl$_2$ was included in the wash buffer.

Briefly, an unmodified "SEPHAROSE 4B" (beaded agarose) column was equilibrated with 5 vol cold (4° C.) Buffer K (TBS, pH 7.5, 50 mM octylglucoside, 3 mM CaCl$_2$). The flow through was collected and adjusted to a final concentration of 3 mM CaCl$_2$. A GRGDSPK-"SEPHAROSE" (beaded agarose) affinity column (20–40 ml) was prepared using the method for preparing the Vn column, above, except that lyophilized GRGDSPK (SEQ ID NO: 5) was suspended in the coupling buffer and the sample was not dialyzed. The column was equilibrated with 200–400 ml Buffer K and placental extract was applied. The flow-through fraction was collected and adjusted to 6 mM MnCl$_2$.

The 110 kDa Fn fragment-"SEPHAROSE" (beaded agarose) column was prepared as described for the Vn column. The column was preequilibrated with 5 vol cold Buffer L (TBS, pH 7.5, 50 mM octylglucoside, 3 mM MnCl$_2$), the extract was applied and the flow-through fraction was collected. The column was washed with 5 vol cold Buffer L, allowed to come to RT (about 30 min), then another 5 vol Buffer L at RT was added. When the OD$_{280}$ of the flow through was below 0.02, FnR was eluted using 3 vol Buffer M (TBS, pH 7.5, 50 mM octylglucoside, 10 mM EDTA) at RT and one-quarter column volume fractions were collected. The fractions were evaluated by 8% SDS-PAGE under non-reducing conditions and fractions exhibiting bands migrating at the characteristic 155 kDa and 110 kDa molecular masses of FnR (Hemler, Ann. Rev. Immunol. 8:365–400 (1990), which is incorporated herein by reference) were pooled, dialyzed into TBS (pH 7.5) containing 50 mM octylglucoside/3 mM MnCl$_2$ and concentrated using an "AMICON YM 30" filter.

6. Purification of Human $\alpha_V\beta_3$ Vitronectin Receptor

The $\alpha_V\beta_3$ receptor was purified from octylglucopyranoside-extracted human placenta prepared as described in Example II.4., above. Two tandem Kontes (Fischer Scientific) columns were prepared using equal volumes of "SEPHAROSE" (beaded agarose) 4B or 6B. The peptide VTRGDVFTK (SEQ ID NO: 6) was coupled to one column using the method described in Example II.5., above (peptide column). The other column was not modified (plain column). Both columns were equilibrated with 5 vol cold (4° C.) Buffer N (1X TBS, 50 mM octylglucoside, 3 mM MnCl$_2$).

The placental extract was applied to the plain column and the flow through was applied to the peptide column. Following application of the flow through, the peptide column was washed with 10–15 vol Buffer N; half the washes were conducted at 4° C. and half were at RT. Elution was with 4 vol Buffer 0 (1X TBS, 50 mM octylglucoside, 10 mM EDTA) and ¼ vol fractions were collected. The fractions were evaluated on 8% SDS-PAGE under non-reducing conditions. Fractions containing bands migrating at the characteristic apparent 150 kDa and 90 kDa molecular masses of the $\alpha_V\beta_3$ receptor were pooled and dialyzed overnight against 20 mM Tris (pH 8.0), 34.5 mM octylglucoside, 2 mM CaCl$_2$, and 2 mM MgCl$_2$.

The dialyzed receptor was loaded onto a "MONO-Q" quaternary amine column (HR 5/51; Pharmacia). The pumps were washed with a gradient of Buffer A$_1$ and B$_1$ before sample loading. Buffer A$_1$ is 20 mM Tris, pH 8.0, 34.5 mM octylglucoside, 2 mM CaCl$_2$, 2 mM MgCl$_2$; Buffer B$_1$ is Buffer A$_1$ containing 1M NaCl. Both buffers were filtered and degassed prior to adding octylglucoside.

The sample was loaded onto the sample loop (valve 1.1, 1 ml/min, 0% B) and injected onto the column (valve 1.2). One ml fractions were collected at 0.05 or 0.1 absorbance units. The appropriate fractions were run on SDS-PAGE and fractions containing $\alpha_V\beta_3$ integrin were pooled and dialyzed against TBS and 50 mM octylglucoside. The integrin was concentrated using an "AMICON" YM 30 filter.

7. Preparation of Recombinant Human Osteopontin

Human osteopontin was produced in CHO cells using standard recombinant DNA methods (see, for example, Sambrook et al., supra, 1989). Plasmid pBS/OP (Young et al., Genomics 7:491–502 (1990), which is incorporated herein by reference), which contains the cDNA sequence encoding human osteopontin, was digested with XhoI, then treated with DNA polymerase (Klenow) and dinucleotide triphosphates to generate blunt ends. The plasmid was digested with XbaI and the approximately 1493 bp fragment containing the osteopontin cDNA insert was purified by electrophoresis on a 0.8% agarose gel.

Plasmid PRC/CMV (Invitrogen; San Diego Calif.) was digested with BstXI and treated with DNA polymerase (Klenow) and dinucleotide triphosphates to generate blunt ends. The plasmid was digested with XbaI and the linearized vector was purified on a 0.8% agarose gel. The 1493 bp osteopontin cDNA was ligated with the linearized vector to produce the human osteopontin expression vector, hOP/PRC/CMV, which exhibited a 1900 bp band following digestion with BamHI and electrophoresis in a 0.9% agarose gel.

Approximately 10 μg purified hOP/PRC/CMV DNA was cotransfected with 1 μg pSV2-dhfr into 80% confluent CHO cells (ATCC CRL 9096) (Subramani et al., *Mol. Cell. Biol.* 1:854–864 (1981), which is incorporated herein by reference). Positive transfectants were grown in the presence of methotrexate and selected on the basis of dhfr expression. Recombinant human osteopontin was purified from the CHO cell medium by immunoaffinity using rabbit anti-human osteopontin antibody (Telios; San Diego Calif.) coupled to CNBr "SEPHAROSE 4B" (Pharmacia). Purified osteopontin was analyzed by SDS-PAGE and migrated with an apparent molecular mass of about 72–76 kDa under non-reducing conditions.

B. In Vitro Assays for Determining RGD Peptide Activity

1. Chick Cell Detachment Assay

Peptides were evaluated for their ability to detach osteoclasts from a matrix consisting of serum-coated microtiter plates. In prescreening assays, 5 μM of the various RGD peptides was used to identify RGD peptides that released at least 60% of the osteoclasts from the matrix.

For RGD peptides that were in the active range as determined by the prescreen, the concentration of active RGD peptide that resulted in the release of 50% of the osteoclasts (IC50) was determined (see FIG. 4). In general, RGD peptides having an IC50 of 3.0 μM or less were selected for further examination using the assays described below. However, some peptides having IC50 values greater than 3.0 μM also were analyzed.

Osteoclasts were isolated from embryonic chicks using a modification of the methods of Boyde et al., *Br. Dent. J.* 156:216 (1984) and Chambers et al., *Endocrinology* 116:234 (1985), each of which is incorporated herein by reference. Briefly, chick long bones (femur and tibia) were dissected free of soft tissue and minced in prewarmed minimum essential medium (MEM, pH 7.2; Irvine Scientific; Irvine, Calif.) with Earl's salts, supplemented with 10% heat-inactivated fetal calf serum (FCS) and 200 mM glutamine and containing 100 μg/ml streptomycin and 100 IU/ml penicillin. Cells were removed from bone fragments by vigorous shaking in a capped centrifuge tube. Large particulate material was allowed to settle prior to removal of the cell suspension. After repeated agitation of the cells with a large transfer pipette, 100 μl aliquots of cells were added in triplicate to Corning 96 well microtiter plates that had been preincubated for 1 hr with 100 μl of MEM/FCS media.

The cells were incubated for 90 min at 37° C. in an atmosphere containing 10% $CO_2$. Following incubation, the cell layers were carefully washed 2x with 200 μl sterile PBS, then 100 μl of fresh MEM/FCS was added. Peptides were diluted in the same medium and added to each well. The cells were incubated overnight as described above. After 20 to 24 hr, media were aspirated and the cells were fixed in 10% formalin and washed 2x with distilled water to remove nonadherent cells and debris. Cell layers were stained for. 5 min using 0.1% crystal violet and multinucleated osteoclasts were counted by light microscopy.

FIG. 2 shows the IC50 values obtained for various RGD peptides and for the naturally occurring protein, echistatin (ECHI), using the chick osteoclast attachment assay (column designated "chick OC detach (FCS)"). FIG. 4 shows the dose response curves for selected RGD peptides.

The chick cell detachment assay also was used to characterize the selectivity of an RGD peptide. The chick cell preparation contains a heterogeneous population of cells, including osteoclasts, osteoblasts, fibroblasts, monocytes and other cell types. A nonselective peptide can inhibit the attachment of these various cell types to the matrix in this assay, whereas a selective peptide according to this invention primarily will inhibit osteoclasts binding.

RGD peptides that are selective for releasing osteoclasts, but not the other cell types, from the matrix were identified by extracting the crystal violet stain from fixed cells and comparing the amount of staining in a control well (no peptide) with the amount of staining following incubation of the cells with an RGD peptide. Crystal violet was extracted using 20% acetic acid and the optical density of the resulting solution was measured in 96 well microtiter plates by spectrophotometry at 562 nm.

Selectivity of a peptide can be characterized as shown in FIG. 5. A peptide that was relatively nonselective indiscriminately detached an increasing number of cells with increasing dose, yielding a declining percent attachment dose-response curve. In contrast, more highly selective peptides detached primarily osteoclasts and had no additional effect once osteoclasts were detached from the matrix until high concentrations of the peptides were attained. Such a selective peptide yielded a curve that was shifted to the right relative to the nonselective peptides; i.e., much higher concentrations of selective peptides were needed to detach cells other than osteoclasts. As shown in FIG. 5, peptides 386 and 20, for example, yielded a curve that is shifted to the right, which indicates that peptides 386 and 20 caused selective detachment of osteoclasts as compared to other cell types. FIG. 6 provides a different visualization of the cell type selectivity data and shows that increasing concentrations of a peptide can selectively detach osteoclasts, as evidenced by the sharp decline in the percent of attached cells, as compared to other cell types, which are not readily detached.

2. Rat Osteoclast Bone Resorption Assay

RGD peptides that were active in the osteoclast detachment assay were evaluated for their ability to inhibit bone resorption. The bone resorption assay further characterizes the potency of an RGD peptide.

Bovine bone femurs were obtained from Pel-Freeze (Rogers, Ariz.). One inch transverse slices were cut using a hand saw and bone plugs were cut on a drill press equipped with a ¼ inch plug cutter. 600 μm thick bone slices were made using a Buehler "ISOMET 2000" diamond saw (Irvine, Calif.). Slices were stored in a 48 well plate containing 10% ethanol.

To remove debris, each slice was sonicated ("FISHER 50 SONIC DISMEMBRATOR" in in ethanol and transferred to a sterile 96 well plate. Alternatively, the bovine bone slices were stored and sonicated in PBS, then placed in individual wells of a chamber slide (Lab-Tek; Nunc; Naperville Ill.). 100 μl of a medium containing 10% FCS and 2% streptomycin/penicillin/glutamine was added to the wells and the plates were incubated at 37° C. for 4 hr.

In addition, tibias, femurs and humeruses were removed from ten or twelve two-day old rat pups (Harlan Sprague, Indianapolis, Ind.) and soft tissue and periosteum was removed. The bones were placed in a petri dish on ice and 3 ml (10 rat pups) or 4 ml (12 rat pups) of medium as above was added. The bones were minced, transferred to a 15 ml conical tube and vigorously shaken for 2 min. The suspension was poured through a 100 μm nylon mesh, which then was washed with 2–5 ml of medium.

In some cases, after transfer to the 15 ml conical tube, the suspension was triturated vigorously for 2 min instead of shaken. The suspension was poured through the 100 μm nylon mesh and 2–5 ml medium was added to the bone fragments remaining in the tube. After 2 min trituration, the suspension was filtered as before.

The cell suspension was agitated using a sterile transfer pipette, medium was removed from the wells containing bovine bone slices and 100 µl of the cell suspension (about $4\times10^4$ cells) was added to each well containing a bone slice. Peptides were diluted in PBS, 5 µl of the peptide solution was added to each well and the plates were incubated for 18 to 22 hr at 37° C. in an atmosphere containing 10% $CO_2$.

When chamber slides were used, the cell suspensions were added and the samples were incubated for 30 min at 37° C., 12.5% $CO_2$. The cells then were gently removed from the slide chamber, leaving the bone slices in their gasket on the slide. Tweezers were used to remove the bone slices, which were washed in warm medium for 8 sec. The slices were placed into the wells of a 12 well tissue culture plate (Corning; Corning N.Y.) containing various peptide dilutions and incubated for 18–22 hr at 37° C., 12.5% $CO_2$.

Following incubation, the supernatant was aspirated and 0.5% trypsin (1× trypsin-EDTA solution; Irvine Scientific; Santa Ana, Calif.) was added to each well containing a bovine bone slice. After 5 or 10 min, the wells were aspirated and 1% "TRITON X-100" (polyoxyethylene ether) (Sigma; St. Louis, Mo.) was added to dissolve the cells. The plate was shaken for 1 hr, then each slice was placed in deionized water, sonicated, dehydrated in 70% ethanol for 5 min and air dried. The bone slices were stained with Millipore-filtered 1% toluidine blue in 1% sodium borate for 30 sec, then washed 3× with deionized water. "WHATMAN" No. 1 filter paper was used to blot the sample, then the slices were air dried. The number of pits per slice was determined by light microscopy ("LABPHOT-2" microscope, Nikon; Melville, N.Y.). The IC50 value was obtained by comparing the number of pits on a bone slice that was treated with a peptide as compared to an untreated slice. The control is set at 100%, which was at least 15 pits/slice. Active peptides reduce the number of pits/slice.

The results of the bone resorption assay are shown in FIG. 2 (column designated "Rat Bone (Pits)"). A low IC50 value in this assay indicated that a relatively low concentration of the RGD peptide inhibited at least one essential step in bone resorption. RGD peptides that were active in this assay were considered particularly promising candidates for use as a pharmacological agent, since this assay utilizes a mammalian system and measures the ability of a peptide to effect the desired end point of inhibiting bone resorption.

3. Rat Osteoclast Attachment Assay

To determine the effect of a peptide on the attachment of rat osteoclasts in vitro, 100 µl aliquots of the rat pup bone cell suspension described in Example II.B.2., above, were added in triplicate to 96 well "MAXISORP" plates coated with specific substrates or with FCS. Substrate coated plates were used to determine the ability of peptides to inhibit attachment or induce detachment of an osteoclast from a ligand such as vitronectin, fibronectin, osteopontin or collagen I (Collaborative Research), which are ligands present in bone. Substrates were added to 96 well plates (50 µl of a 5–10 µg/ml solution in sodium carbonate, pH 9.5) and incubated for 2 hr at 37° C. For FCS control wells, 100 µl 10% FCS was added. Wells were aspirated, then washed 2× with PBS and blocked with 1% bovine serum albumin in PBS for 2 hr at 37° C. Wells were aspirated and washed again 2× with PBS. Cells were seeded in duplicate at $4\times10^4$ cells/well.

Immediately following addition of the cells, peptides were added to each well and the plates were incubated for 1 hr at 37° C., 10% $CO_2$. Alternatively, peptide was added before cell addition. PBS was aspirated from the precoated wells and 10 µl of each peptide dilution was added, then 100 µl of cell suspension (about $4\times10^4$ cells/well) was added. The plate incubated for 1 hr at 37° C., 10% $CO_2$.

Figure 7:
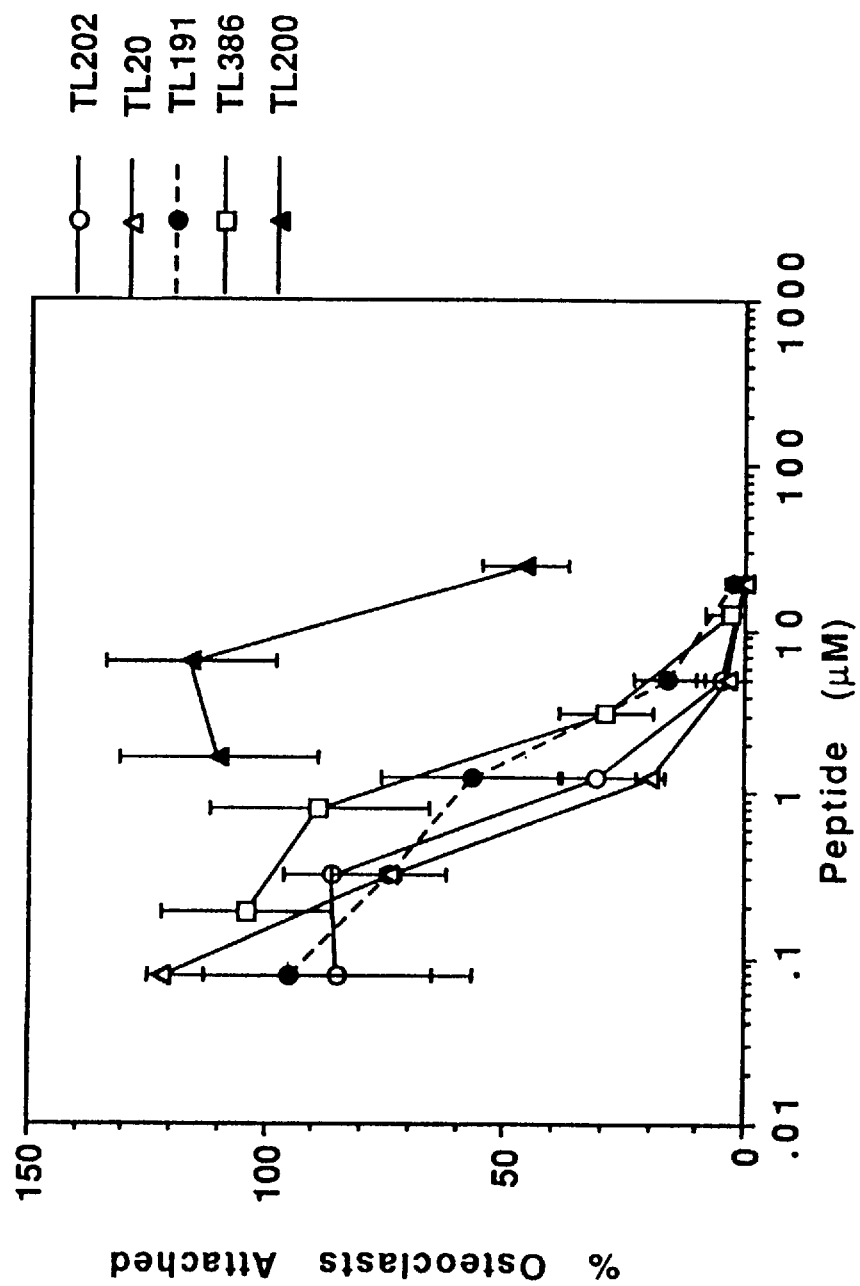
FIG. 7 demonstrates the effectiveness of various peptides in the rat osteoclast attachment assay using fetal calf serum as substrate.
Figure 10A:
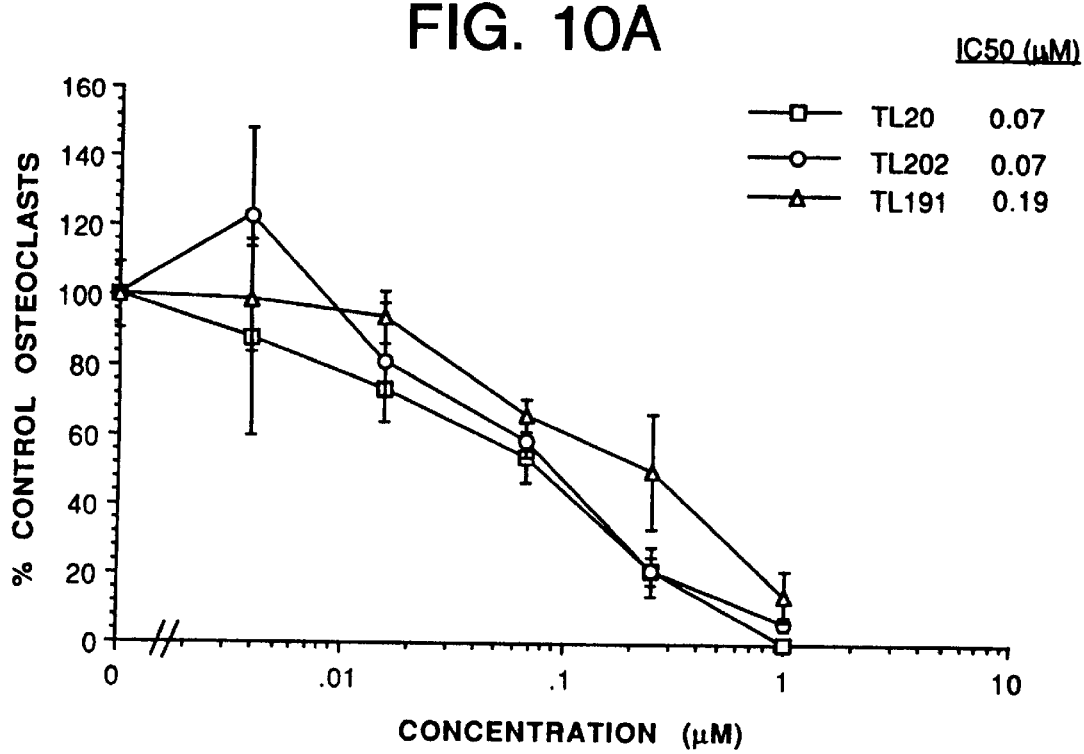
FIG. 10 demonstrates the effectiveness of various RGD peptides of the invention in the rat osteoclast attachment assay using osteopontin (OPN) or vitronectin (Vn) as substrate.
Figure 10B:
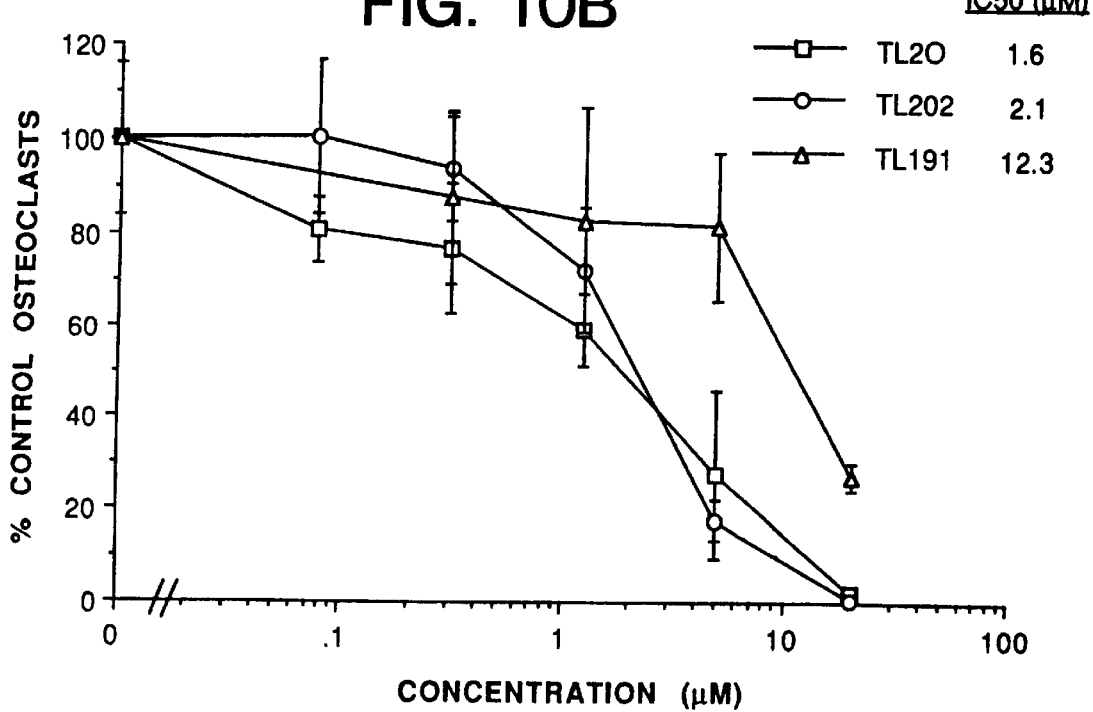
Figure 12:
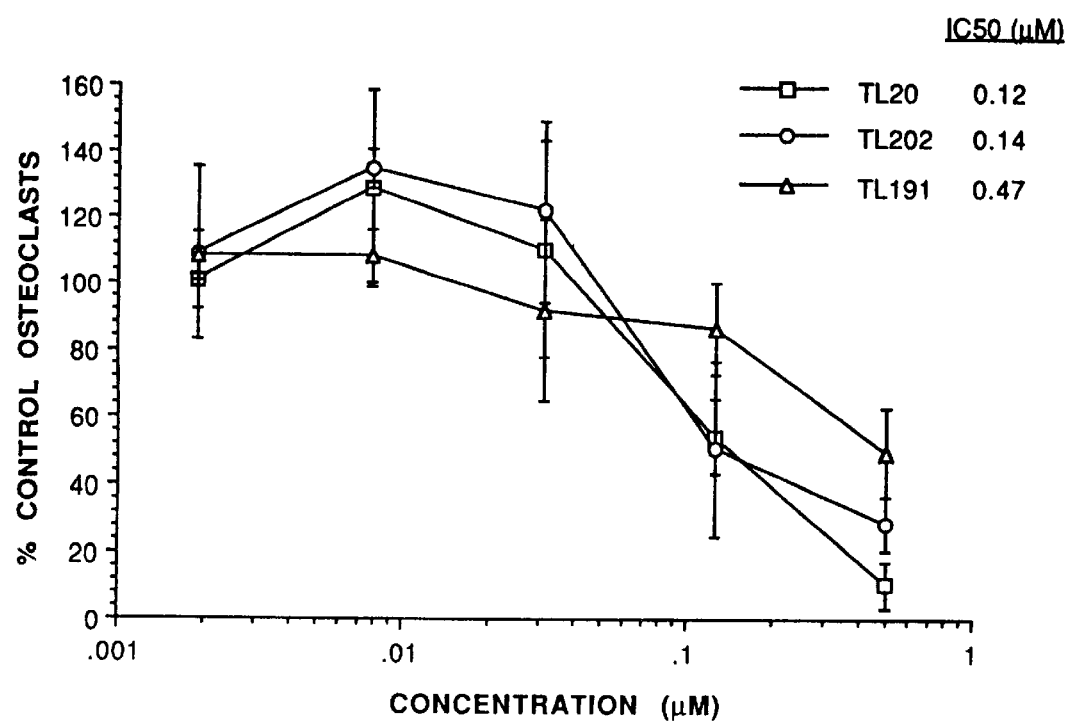
FIG. 12 demonstrates the effectiveness of various RGD peptides of the invention in the rat osteoclast attachment assay using fibronectin as substrate.

Following incubation, the medium and nonadherent cells were removed by aspiration from each well. Cells were fixed in acetone/citrate, washed 2× with distilled water, then stained with 0.1% crystal violet for 5 min. Adherent osteoclasts were counted by light microscopy. The results of these experiments are shown in FIG. 7 (FCS), FIG. 10 (osteopontin and vitronectin), FIG. 11 (collagen) and FIG. 12 (fibronectin).

Adherent osteoclasts also were counted using immunocytochemistry. Following the 1 hr incubation of the cells with the peptides, 200 µl blocking solution was added to each well and incubated for 1 hr at RT (blocking solution is 10% normal goat serum in 1X TBSC (1X TBSC is 0.3% casein in TBS). Immediately after aspiration, 50 µl of 0.1 µg/ml primary antibody was added to the appropriate wells and incubated 1 hr at RT on a shaker. The primary antibody was F-11 (Pharmingen; San Diego Calif.) diluted to 0.1 mg/ml with TBSC adjusted to 1:66 of normal goat serum. The cells then were rinsed in TBST (10X TBST is 200 µl "TRITON X-100" (polyoxyethylene ether) and 100 ml of 10X TBS) and the wells were filled with TBST. The wells were allowed to stand for 20 min on the shaker.

Immediately after aspiration of TBST, 50 µl 1:300 biotinylated goat anti-mouse Ab (Vector; Temecula Calif.) was added to each well. Antibody dilution was in TBSC as above. Incubation and rinsing were as described above for the F-11 antibody, except that the incubation time was 30 min and the shaking rinse time was to 15 min.

After aspiration of the second rinse, an inhibiting solution (10 ml 50% methanol, 400 µl hydrogen peroxide, 200 µl sodium azide) was added to each well and allowed to stand for 15 min at RT. The wells were rinsed with water, then filled with water and allowed to stand for 5 min. After aspiration, this rinsing procedure was repeated with 1X TBSABC (90 ml 10X TBS, 20.22 g NaCl, volume adjusted to 1 liter); the second rinse was allowed to stand for 10 min before aspiration.

ABC solution (1:50 avidin solution and 1:50 biotin solution (Vector) in 1X TBSABC; freshly made) was added to each well and incubated for 30 min at RT. The wells were washed with TBSABC and shaken at low speed for 20 min on the shaker. After aspiration, bound antibody was detected using VIP Substrate (Vector) according to the manufacturer's recommendations. After aspiration and air-drying, adherent osteoclasts were counted by light microscopy.

Mammalian osteoclasts primarily express $\alpha_V\beta_3$, $\alpha_2\beta_1$ and $\alpha_V\beta_1$ integrins. Human MG63 osteosarcoma cells and normal rat kidney (NRK) cells contain $\alpha_V\beta_5$, $\alpha_2\beta_1$ and $\alpha_5\beta_1$ surface receptors. For comparison to osteoclasts, these cells are considered normal with respect to the expression of multiple integrins capable of attachment to more than one ligand. Because MG63 and NRK cells lack high expression of $\alpha_V\beta_3$, the range of activity of peptides on these cells reflects the range of selectivity.

MG63 and NRK cell lines were purchased from ATTC (Rockville Md.). Cultures were maintained in DMEM containing 10% FCS. For attachment assays, cells were trypsinized, resuspended in serum-free DMEM and seeded in duplicate at $4\times10^4$ cells/well in 96 well microtiter plates that had been precoated with 10% FCS. Peptides were added and the cells were incubated for 1 hr at 37° C., 5% $CO_2$.

Following incubation, cell layers were washed gently with warm DMEM, fixed in 10% formalin for 25 min, then stained with 0.1% crystal violet for 5 min. Following staining, the stain was extracted with 20% acetic acid and the $OD_{562}$ of the extracted stain was determined. The OD values obtained for wells containing peptide were compared to control wells, which represent maximum binding. The results of these experiments on NRK cells are shown in FIG. 8 and in FIG. 2 for both cell types.

Figure 8:
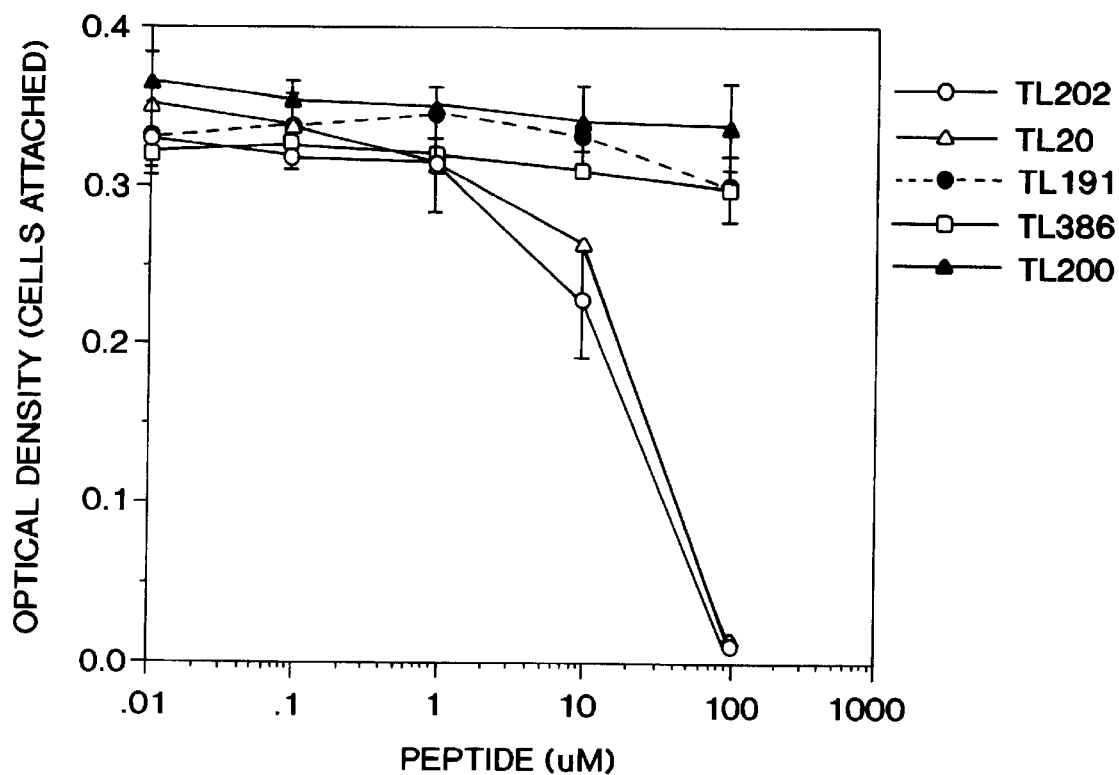
FIG. 8 demonstrates the selectivity of various peptides in the rat kidney cell attachment assay. Peptides that are selective for binding $\alpha_V\beta_3$ integrin, which is not present on normal rat kidney cells, do not affect attachment of the cells, whereas peptides that are nonselective for this integrin show a dose response for inhibition of cell attachment.

Selectivity of a peptide can be determined by comparing the results of FIGS. 7 and 8 (see, also FIG. 2). Peptides that were highly active (low IC50) both on osteoclast attachment and on MG63 or NRK attachment are considered relatively nonselective. In contrast, peptides that were highly active on osteoclast attachment but were less active on MG63 or NRK attachment are considered selective (TL191, TL386, TL159, TL487 and TL750).

4. JY Cell Attachment Assay

JY cells are human-derived B lymphocyte cells that express the $\alpha_V\beta_3$ VnR, which is the receptor that most likely is involved in osteoclast binding to bone (Stupack et al., *Expt. Cell Res.* 203:443–448 (1992), which is incorporated herein by reference). JY cells do not express the $\alpha_V\beta_5$ VnR. RGD peptides were analyzed for their ability to inhibit the attachment of JY cells to vitronectin-coated plates.

Binding in the JY attachment assay is particularly relevant as a measure of the potency of a peptide, since JY cells are human cells and the $\alpha_V\beta_3$ VnR present on JY cells likely is the primary receptor involved in osteoclast attachment to bone. In chick osteoclasts, both $\alpha_V\beta_3$ and $\alpha_V\beta_5$ are expressed and likely involved in attachment. In addition, the JY attachment assay, when compared with the receptor-specific enzyme-linked immunosorbent assays (ELISAs) described below, demonstrates the selectivity of RGD peptides for inhibiting binding due to the $\alpha_V\beta_3$ VnR.

JY cells were grown in suspension in RPMI media (Irvine Scientific; Irvine, Calif.) supplemented with 10% heat inactivated fetal bovine serum (FBS) and 200 mM glutamine and containing 100 IU/ml penicillin and 100 µg/ml streptomycin. A 96 well ELISA plate (Linbro, Titertek) was coated with 100 µl/well of 5 µg/ml human Vn in sodium carbonate (pH 9.5) and incubated overnight at 4° C. The plate was rinsed 3× with PBS and blocked by adding 100 µl/well of 2 mg/ml BSA in PBS and incubating for 1 hr. Following blocking, the wells were washed 2× with PBS.

While the wells were being blocked, the JY cells were rinsed 2× with PBS, then resuspended to $10 \times 10^5$ cells/ml in serum-free RPMI containing 2 mg/ml BSA, 200 mM glutamine, 100 IU/ml penicillin, 100 µg/ml streptomycin and 0.5 mM $MnCl_2$. At this time, 50 ng/ml phorbol myristate acetate (PMA; Sigma) was added to the cell suspension. PMA stimulates the cells and allows them to bind Vn.

RGD peptides were diluted in the serum-free RPMI and 50 µl of each dilution was added to duplicate wells. 50 µl of the JY cell suspension was added to each well and the plate was incubated at 37° C. for 45 min, 7% $CO_2$. Nonadherent cells were gently aspirated from the wells and the wells were rinsed 1× with PBS. Cells were fixed in 10% formalin in PBS for 10 min, then stained with 0.1% toluidine blue for 1 hr. The plate was rinsed with distilled water and the cells were solubilized using 1% SDS. The amount of staining was determined by spectrophotometry at 595 nm and the IC50 was calculated as the concentration of an RGD peptide that inhibited JY cell binding to Vn by 50% (see FIG. 2, column designated "JY attach ($\alpha_V\beta_3$/Vn)").

5. Effect of RGD Peptides on Binding to $\alpha_V\beta_5$, $\alpha_5\beta_1$ and $\alpha_V\beta_3$ Integrin Receptors—ELISA Peptide binding to purified human $\alpha_V\beta_5$ and $\alpha_V\beta_3$, which are VnR's, and to $\alpha_5\beta_1$, which is a FnR, was determined using competitive ELISA assays as described below. If desired, an $\alpha_{IIb}\beta_3$ ELISA can be performed as described in WO91/15515.

a. $\alpha_V\beta_5$ ELISA

For the $\alpha_V\beta_5$ assays, Vn was immobilized and the binding of solubilized $\alpha_V\beta_5$ in the presence of various concentrations of a peptide analogue was detected using a mouse monoclonal antibody to human $\alpha_V$ (clone VNR 147; Gibco; Gaithersburg, Md.). Binding of the antibody was visualized using a second antibody conjugated to horseradish peroxidase (BioRad; Richmond, Calif.).

Microtiter plates were coated at RT by adding 100 µl of 10 µg/ml human Vn in 0.05M sodium carbonate buffer (pH 9.6). The plates were incubated overnight at 4° C., then washed 3× with TBS containing 0.05% "TWEEN 20" (polyoxyethylenesorbitan monolaurate) ("TWEEN 20" (polyoxyethylenesorbitan monolaurate)). RGD peptides were diluted in TBS containing 20 mM OG, 2 mM $CaCl_2$ and 2 mM $MgCl_2$ and 50 µl was added to each well at 10-fold serial dilutions. Human $\alpha_V\beta_5$ was diluted in the same buffer and 50 µl was added to each well. Similar results were observed when the receptor was added prior to addition of the peptide.

The plates were incubated for 3 hr at RT, then washed with 300 µl TBS/"TWEEN 20" (polyoxyethylenesorbitan monolaurate) buffer. Bound receptor was incubated with 100 µl of the monoclonal anti-$\alpha_V$ antibody (diluted in TBS/"TWEEN 20" (polyoxyethylenesorbitan monolaurate) for 2 hr, then the wells were washed three times with TBS/"TWEEN 20" (polyoxyethylenesorbitan monolaurate). 100 µl of a 1:3000 dilution of affinity purified goat anti-mouse IgG conjugated to horseradish peroxidase was added to each well and the plates were incubated overnight at 4° C. Following incubation, the plates were washed 3× with TBS/"TWEEN 20" (polyoxyethylenesorbitan monolaurate) and 100 µl of the substrate mixture (10 mg O-phenylenediamine in 25 ml 0.1M citrate phosphate buffer, pH 5.0, 6 µl 30% $H_2O_2$) was added to the wells. The reaction was allowed to develop for 10–15 min in the dark, then the development reaction was stopped by adding 50 µl of 4 N $H_2SO_4$ to each well.

The amount of reaction product was quantitated by spectrophotometry at 490 nm. The IC50 was determined by computer using a Molecular Devices microplate reading spectrophotometer and "SOFTMAX" 2.2 software using 4-parameter analysis. Nonspecific binding of antibody was measured in wells that did not contain receptor and this value was subtracted from total binding measured in wells containing receptor to yield the specific binding.

b. $\alpha_5\beta_1$ ELISA

Peptide binding to purified human $\alpha_5\beta 1$ (FnR) also was determined using a competitive ELISA. In these assays, Fn was immobilized to the wells and the binding of solubilized FnR in the presence of various concentrations of a peptide analogue was determined using a mouse monoclonal antibody to human $\beta_1$ (clone P4C10; Gibco) and specific binding was visualized using a second antibody.

Microtiter wells were coated at RT by adding 100 µl of 2 µg/ml human Fn in TBS and incubating the plates overnight at 4° C. Following incubation, the plates were washed 3× with TBS/"TWEEN 20" (polyoxyethylenesorbitan monolaurate). RGD peptides were diluted in TBS containing 20 mM OG and 2 mM $MnCl_2$ and 50 μl was added to wells at 10-fold serial dilutions. FnR was diluted in the same buffer and 50 μl was added to each well.

The plates were incubated for 3 hr at RT and washed with 300 μl TBS/"TWEEN 20" (polyoxyethylenesorbitan monolaurate). Bound receptor was incubated with 100 μl of the monoclonal anti-$β_1$ antibody for 2 hr, then washed 3× with TBS/"TWEEN 20" (polyoxyethylenesorbitan monolaurate). 100 μl of a 1:3000 fold dilution of affinity purified goat anti-mouse IgG conjugated to horseradish peroxidase was added to each well and incubated overnight at 4° C. The amount of bound second antibody was determined as described above.

c. $α_Vβ_3$ ELISA

Peptide binding to purified $α_Vβ_3$ receptor was determined by using a competitive ELISA, in which $α_Vβ_3$ receptor was immobilized and the binding of solubilized VN, in the presence of various concentrations of peptide analogue, was detected using a monoclonal mouse IgG anti-VN antibody and a labelled anti-mouse IgG conjugate. A monoclonal anti-VN antibody can be obtained using routine methods (see, for example, Harlow and Lane, *Antibodies: A laboratory manual* (Cold Spring Harbor Laboratory Press 1988), which is incorporated herein by reference).

96 well microtiter plates were coated overnight at RT with 100 μl/well of $α_Vβ_3$ receptor (0.5 μg/ml in 1X TBS, 4 mM octylglucoside, 1 mM $CaCl_2$). The wells were blocked with 200 μl/well of 1% BSA in 1X TBS, 1 mM $CaCl_2$ for at least 30 min. The plates were washed 2× with 1X TBS, 1 mM $CaCl_2$. 50 μl peptide in 1X TBS, 1 mM $CaCl_2$, 0.05% "TWEEN 20" (polyoxyethylenesorbitan monolaurate) was added in 10-fold serial dilutions. 50 μl of Vn in the same buffer then was added to each well.

The plates were incubated for 3 hr at RT, then washed 3× with 1X TBS, 0.05% "TWEEN 20" (polyoxyethylenesorbitan monolaurate). 100 μl of 8E6 (Telios) diluted to 1:6000 in 1X TBS, 0.05% "TWEEN 20" (polyoxyethylenesorbitan monolaurate) was added to the wells and the plates were incubated for 1 hr at RT. Plates were washed 3× with 1X TBS, 0.05% "TWEEN 20" (polyoxyethylenesorbitan monolaurate). Affinity purified goat anti-mouse IgG conjugated to horseradish peroxidase (100 μl/well; BioRad; Hercules Calif.) was added to each well and incubated for 1 hr at RT. Plates were washed 3× with 1X TBS, 0.05% "TWEEN 20" (polyoxyethylenesorbitan monolaurate). 100 μl/well of substrate mixture (10 mg O-phenylenediamine in 25 ml 0.1M citrate-phosphate buffer, pH 5.0, 6 μl 30% $H_2O_2$) was added to the plates and allowed to develop. The development process was stopped by adding 50 μl to 4 N $H_2SO_4$ to each well. The plates were read at 490 nm and the data analyzed by four parameter fit.

d. Analysis of ELISA results

The IC50 values for various RGD peptides were calculated by determining the concentration of a peptide that inhibited binding of Vn to $α_Vβ_5$ or $α_Vβ_3$ or of Fn to $α_5β_1$ by 50%. The results of these assays are shown in FIG. 2 (columns designated "Receptor Assays").

Comparison of the IC50 values generated using the JY cell assay and the $α_Vβ_3$ ELISA, which measure binding of the $α_Vβ_3$ receptor involved in osteoclast binding to bone, with the $α_Vβ_5$ and $α_5β_1$ receptor-specific ELISAs, which represent receptors that likely are not involved in osteoclast attachment, provides insight into the receptor selectivity of the peptides. For example, a peptide such as peptide 368, which has an IC50 value for the $α_Vβ_3$ ELISA or the $α_Vβ_3$ VnR present on JY cells that is significantly lower than its IC50 value for the $α_Vβ_5$ and $α_5β_1$ receptors indicates that peptide 368 is a selective peptide.

In summary, the above series of assays are useful for determining the potency and selectivity of a peptide. Examples of particularly receptor selective peptides include 386, 814, 191, 228, 186, 368, 138, 448, 159, 487 and 750. Examples of particularly potent peptides include 373, 202, 196, 206, 197, 199, 183, 832, 812, 20, 437, 441, 429, 110, 214, 108, 431 and 751. Examples of peptides that are both potent and selective include 191, 368, 159, 487 and 750.

6. Effect of RGD Peptides on Platelet Aggregation

This example provides a method for performing a platelet aggregation assay, which is a measure of peptide binding to the platelet $α_{IIb}β_3$ integrin receptor.

Platelet-rich plasma (PRP) was prepared fresh from heparinized whole blood. 0.6 ml PRP was placed in a 1.5 ml microcentrifuge tube and centrifuged for 4 min at 14,000×g. Following centrifugation, 0.5 ml supernatant (platelet poor plasma; PPP) was transferred to a 1 ml silicon coated aggregometer tube (Chrono-Log Corp.; Havertown Pa.) and placed in the PPP slot of a Chrono-Log Model 400VS aggregometer (see Tschopp et al., *Thromb. Haem.* 72:119–124 (1994), which is incorporated herein by reference).

Platelet concentration of the PRP sample was determined using a cell counter and the sample was diluted with homologous PPP to obtain 300,000 platelets/μl. 0.5 ml of the diluted PRP was placed in an aggregometer tube with a stir bar and incubated for 5 min at 37° C. without stirring. The tube was transferred to the PRP slot in the aggregometer and the sample was stirred at 1200 rpm for 5–10 min at 37° C. Peptides were dissolved in physiological saline and added at various concentrations to a PRP sample in the aggregometer. Saline, alone, was added for control reactions.

Platelet aggregation was initiated by adding adenosine diphosphate (ADP) to a concentration of 10 μM. Platelet aggregation was measured in 2 mm units from baseline (before ADP addition) to response at two min from the time of ADP addition or maximal response (if before 2 min), whichever is larger. Peptide inhibitory activity was determined by comparing aggregation in the presence and absence of peptide and the concentration (μM) of peptide that inhibited platelet aggregation by 50% (IC50) was determined.

As shown in FIG. 2, the peptides of the invention were variously effective in inhibiting platelet aggregation (column labelled "Plate. Aggreg. (hep)"). Peptides 754 and 940 were particularly effective in inhibiting platelet aggregation at a low concentrations. These peptides also are relatively potent for binding the $α_Vβ_3$ and, therefore, can be useful for reducing or preventing restenosis (see Choi et al., supra, 1994; Topol et al., supra. 1994).

7. Effect of RGD Peptides on Angiogenesis

This example describes the use of the chick chorioallantoic membrane (CAM) assay to identify peptides of the invention that reduce or inhibit angiogenesis.

The CAM assay is performed as described by Brooks et al., supra, 1994a, 1994b). Tumor culture on the chick CAM is accomplished using 10 day old chick embryos. A small hole is made through the egg shell at the end of the egg directly over the sac using a small crafts drill (Dremel; Racine Wis.). A second hole is drilled on the broad side of the egg directly over embryonic blood vessels. Negative pressure is applied to the original hole, resulting in the CAM pulling away from the shell on the opposing side. A 1×1 cm window is cut in the shell and 50 mg fragments of human tumor, which are grown on a separate embryo CAM, is placed on the CAM of the new embryo. The window is covered with tape and the embryo is incubated 24 hr at 37° C.

Following the 24 hr incubation period, the embryo is inoculated with 300 μg of a peptide or with saline (control). Incubation then is continued for an additional 3 days, after which the tumor is resected and analyzed for angiogenesis, or for an additional 7 days, after which the tumor is removed and weighed to determine the change from the original weight. Tumors can be analyzed histologically using standard fixation and paraffin embedding procedures.

EXAMPLE III

RGD Peptide Activity In Vivo

This example provides methods for determining the activity of an RGD peptide of the invention to reduce or inhibit bone resorption or restenosis in vivo.

A. Effect of RGD Peptides on Parathyroid Hormone-induced Hypercalcemia in Mice This example demonstrates that the RGD peptides of the invention can inhibit parathyroid hormone-induced hypercalcemia, which is a measure of osteoclast activation in a subject. Parathyroid hormone (PTH) activates osteoclasts, which are involved in bone resorption. Associated with the increased osteoclast activity is an increase in serum calcium. The PTH-induced hypercalcemia assay measures the level of serum calcium, which is an indication of bone resorption in a subject (Fischer et al., *Endocrinology* 132:1411–1413 (1993), which is incorporated herein by reference).

Swiss-Webster mice, which had been parathyroidectomized two weeks prior to beginning the assay, were obtained from Taconic Lab Animals and Services (Germantown N.Y.). Femoral vein catheters (PE-50 fused with PE10 polyethylene tubing; Becton Dickinson; Parsippany, N.J.) were installed in the mice, flushed and locked with heparinized saline (1:10), sutured to adjacent muscle and internalized within the inguinal space of the incision before closing the incision with wound clips. Baseline serum ionized calcium levels were less than 1.29 mM for mice selected for this study. Serum calcium measurements were performed by atomic absorption spectrophotometry using a Perkin-Elmer model 2380 AA spectrophotometer (Perkin-Elmer; Norwalk Conn.).

The experiment was initiated by feeding the mice a calcium-deficient diet overnight, then injecting the mice the following morning with a bolus of 0.2 mg PTH/kg (hPTH 1–34; Bachem; Torrance Calif.), intravenously. An ionized serum calcium level was obtained 30 min prior to PTH infusion. Various doses of a peptide or vehicle were infused into an animal for 4 hr, then ionized serum calcium again was measured. Lyophilized peptide was redissolved in PBS or in water, depending on the solubility at a particular concentration. Serum calcium measurements were expressed as the difference between the value 30 min before the PTH pulse and 4 hr after peptide infusion was started.

Figure 9:
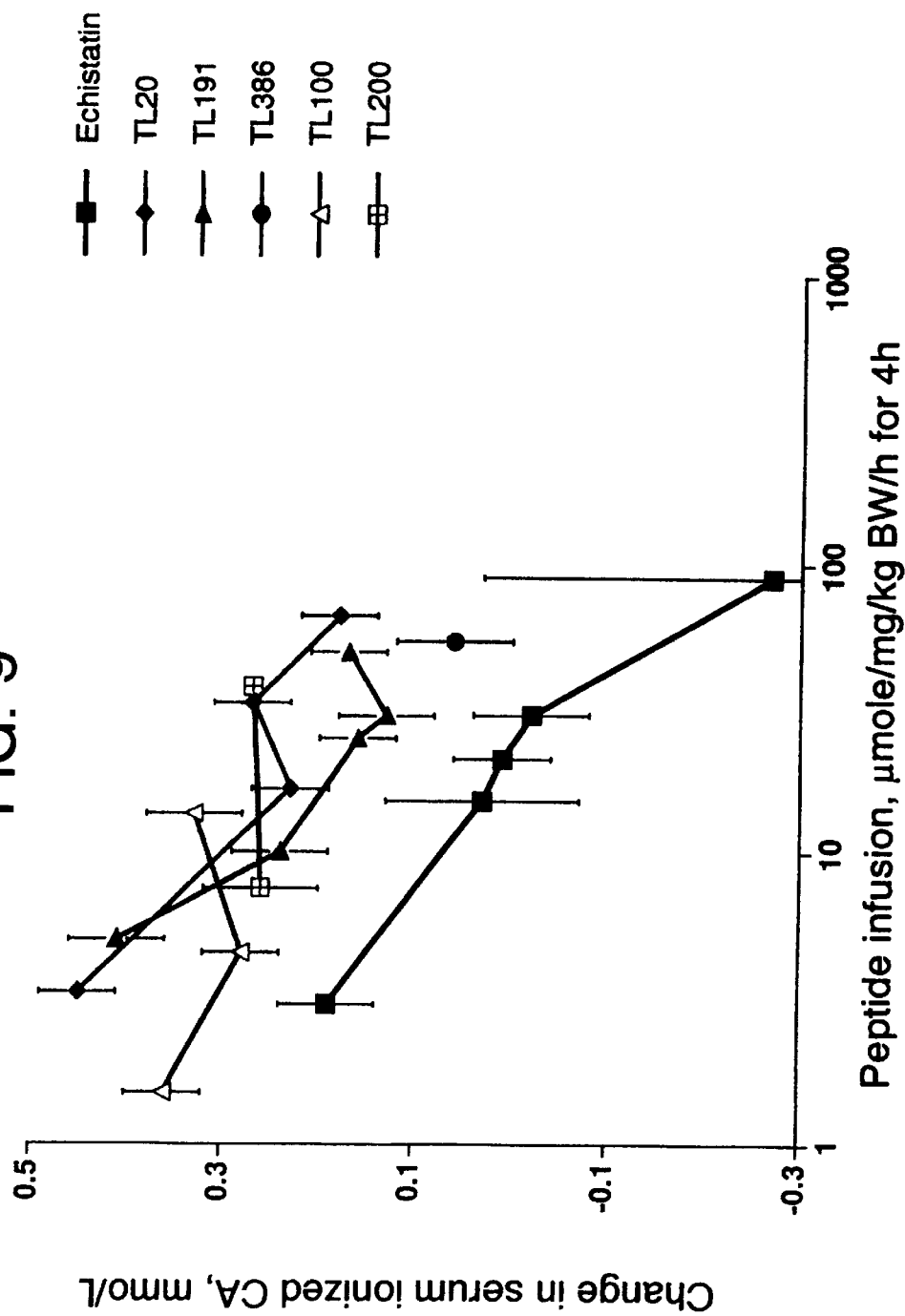
FIG. 9 shows the change in serum ionized calcium resulting from infusion of various peptides at the indicated concentrations.

One control peptide used for this experiment was echistatin (Bachem; Torrance Calif.), which was administered at doses ranging from 0–30 mg/kg/hr. Another control peptide was TL200, an RGD-containing peptide that is selective for the GPIIbIIIa integrin receptor present on platelets. The data presented in FIG. 9 demonstrate a dose responsive effect of the peptides. Peptides TL20 and TL191 decreased the PTH-induced rise in serum ionized calcium in a dose responsive manner. Peptide TL386 was analyzed at a single dose, which resulted in a relatively low level of serum calcium measured in animals within this group. The control peptide, TL200, did not show a dose responsive effect, confirming the selective nature of the TL20, TL191 and TL 386 peptides.

The ability of the peptides of the invention to reduce or inhibit bone resorption also is evaluated by determining the inhibition of bone loss in an ovariectomized rat, which is a model for estrogen deficiency-induced bone loss as occurs in post-menopausal women. The assay is performed as described by Kalu, *Bone Miner.* 15:175–192 (1991), which is incorporated herein by reference. In addition, useful animal model systems for evaluating the effectiveness of a peptide to reduce or inhibit bone resorption are described by Rogers et al., *Bone* 14:369–377 (1993), which is incorporated herein by reference.

In experiments using these model systems, a peptide is administered to an ovariectomized animal and bone loss is measured over a period of time such as over a five week period. A composition comprising the peptide can be administered in any of various ways such as intravenous, intraperitoneal, intramuscular or subcutaneous injection. In particular, a composition can be administered subcutaneously in the form of peptide-containing microcapsules.

The skilled artisan will understand that an effective peptide can be identified by administering various amounts of a peptide to groups of animals in order to obtain statistically significant results. For example, a range of peptide doses of about 0.1, 1, 10 or 100 mg/kg/day can provide an indication of an effective amount of a peptide, which can reduce or inhibit bone resorption. One or more groups of animals can serve as appropriate controls.

B. Effect of RGD Peptides on Restenosis in Guinea Pigs

This example provides a method for identifying RGD peptides of the invention that can reduce or inhibit restenosis. Various animal models of restenosis are well known (see, for example, Choi et al., supra, 1994; see, also, Jackson, *Trends Cardiovasc. Med.* 4:122–130 (1994)). A guinea pig model of restenosis as described herein also is useful for identify effective peptides.

Guinea pigs (300–400. g; 2–3 months old) are anesthetized and the left common carotid artery (LCCA) and right internal jugular vein are exposed through a midline incision in the neck. The internal vein is isolated and ligated. A silastic tube (PE-160) attached to an "ALZET" osmotic minipump (2 ml; Alza; Palo Alto Calif.) is introduced into the open end of the same vessel and the pump is placed in a subcutaneous tunnel on the dorsal surface of the animal. A 2F Fogarty balloon catheter is introduced into the left external carotid artery (LECA), inflated and withdrawn three times to denude the endothelium in the LCCA. The catheter then is removed, the LECA is ligated and the surgical wound is clamped.

Saline (control) or various concentrations of peptide are delivered via the minipump at a rate of about 10 μl/hr for 7 days. Three weeks after balloon injury, guinea pigs are anesthetized and an abdominal incision is made to expose the abdominal aorta. An 18 gauge IV catheter is used to flush (50 ml Ringer's lactate) and fix (200 ml 4% formaldehyde) in vivo during a lethal injection of pentothal via the tail vein. Histological sections are prepared by cutting the LCCA in serial 2 mm sections and staining with hematoxylin-eosin and with Lawson's elastic-van Gieson stain on separate slides. Morphometric analyses are performed using a computerized digital microscopy algorithm to measure the cross-sectional area of the lumen, intima, media and adventitia for the extent of neointimal thickening.

Although the invention has been described with reference to the examples provided above, it should be understood that various modifications can be made without departing from the spirit of the invention. Accordingly, the invention is limited only by the claims.

---

We claim:

1. A method of altering bone resorption in a subject in need thereof, comprising administering to the subject a peptide having the structure:

$X_1\ X_2\ X_3\ X_4\ GD\ X_5\ X_6\ X_7\ X_8$ wherein:

$X_1$ is $R_1R_2$, wherein $R_1$ is an H or alkyl group and $R_2$ is an H, alkyl, $CH_3CO$, alkyl-CO or phenyl-CO group; or 0 to 10 amino acids, which can be protected by acetylation at an N-terminus;

$X_2$ is 0 or 1 amino acid;

$X_3$ is 0, 1 or 2 amino acids;

$X_4$ is N-Me-Arg;

$X_5$ is an amino acid that provides an ionic interaction with an integrin receptor or is Msa, Psa or Tfsa;

$X_6$ is an amino acid having an aliphatic side chain or is a non-natural amino acid that is hydrophobic or is Thr;

$X_7$ is a residue capable of forming a bond with a bridging amino acid of $X_2$; or with $X_3$ when $X_2$ is 0; or with $X_4$ when $X_2$ and $X_3$ are 0, to conformationally restrain the peptide;

$X_8$ is —$NR_3R_4$, wherein $R_3$ is an H or alkyl group and $R_4$ is an H or alkyl group; or —$OR_5$, wherein $R_5$ is an H or alkyl group; or 0 to 10 amino acids, which can be protected as an amide at the C-terminus; and, wherein bone resorption is altered.

2. A method of altering osteoclast binding to a matrix in a subject in need thereof, comprising contacting the osteoclast with an effective amount of a peptide having the structure:

$X_1\ X_2\ X_3\ X_4\ GD\ X_5\ X_6\ X_7\ X_8$ wherein:

$X_1$ is $R_1R_2$, wherein $R_1$ is an H or alkyl group and $R_2$ is an H, alkyl, $CH_3CO$, alkyl-CO or phenyl-CO group; or 0 to 10 amino acids, which can be protected by acetylation at an N-terminus;

$X_2$ is 0 or 1 amino acid;

$X_3$ is 0, 1 or 2 amino acids;

$X_4$ is N-Me-Arg;

$X_5$ is an amino acid that provides an ionic interaction with an integrin receptor or is Msa, Psa, or Tfsa;

$X_6$ is an amino acid having an aliphatic side chain or is a non-natural amino acid that is hydrophobic or is Thr;

$X_7$ is a residue capable of forming a bond with a bridging amino acid of $X_2$; or with $X_3$ when $X_2$ is 0; or with $X_4$ when $X_2$ and $X_3$ are 0, to conformationally restrain the peptide;

$X_8$ is —$NR_3R_4$, wherein $R_3$ is an H or alkyl group and $R_4$ is an H or alkyl group; or —$OR_5$, wherein $R_5$ is an H or alkyl group; or 0 to 10 amino acids, which can be protected as an amide at the C-terminus; and, wherein osteoclast binding to a matrix is altered.

* * * * *

UNITED STATES PATENT AND TRADEMARK OFFICE
CERTIFICATE OF CORRECTION

PATENT NO. : 5,807,819
DATED : September 15, 1998
INVENTOR(S) : Cheng et al.

Page 1 of 2

It is certified that error appears in the above-identified patent and that said Letters Patent is hereby corrected as shown below:

Column 5,
Line 57, please delete "t-BvG," and replace therefor -- t-(BuG), --.
Line 58, please delete "X, is" and replace therefor -- $X_7$ is --.

Column 6,
Lines 3-13, please delete "G-R-G-D-E-P-D-G (SEQ ID NO: 16); R-G-D-N-I-E-$NH_2$ (SEQ ID NO: 25); G-Pmc-R-G-D-C-A (SEQ ID NO: 34); G-Pen-G-R-G-D-N-Y-C-A (SEQ ID NO: 35); G-Pen-G-E-R-G-D-N-Y-C-A (SEQ ID NO: 36); G-Pen-A-A-R-G-D-V-P-C-A-$NH_2$ (SEQ ID NO: 37); G-Pen-E-L-R-G-D-G-W-C-$NH_2$ (SEQ ID NO: 38); G-Pen-G-F-R-G-D-E-P-C-$NH_2$ (SEQ ID NO: 39); K-Pen-G-F-R-G-D-E-P-C-R (SEQ ID NO: 40); K-Pen-G-F-R-G-D-D-P-C-R (SEQ ID NO: 41); Ac-Pen-A-A-R-G-D-Orn-P-C-$NH_2$(SEQ ID NO: 42); (Mpa)-R-G-D-(YOMe)-(t-Bug)-C-$NH_2$ (SEQ ID NO:43) and (Mpa)-R-G-D-(Cha)-(t-BuG)-C-$NH_2$ (SEQ ID NO:44)" and replace therefor -- G-R-G-D-E-P-D-G (SEQ ID NO: 16); R-G-D-N-I-E-$NH_2$ (SEQ ID NO: 25); G-Pmc-R-G-D-C-A (SEQ ID NO: 34); G-Pen-G-R-G-D-N-Y-C-A (SEQ ID NO: 35); G-Pen-G-E-R-G-D-N-Y-C-A (SEQ ID NO: 36); G-Pen-A-A-R-G-D-V-P-C-A-$NH_2$ (SEQ ID NO: 37); G-Pen-E-L-R-G-D-G-W-C-$NH_2$ (SEQ ID NO: 38); G-Pen-G-F-R-G-D-E-P-C-$NH_2$ (SEQ ID NO: 39); K-Pen-G-F-R-G-D-E-P-C-R (SEQ ID NO: 40); K-Pen-G-F-R-G-D-D-P-C-R (SEQ ID NO: 41); Ac-Pen-A-A-R-G-D-Orn-P-C-$NH_2$ (SEQ ID NO: 42); (Mpa)-R-G-D-(YOMe)-(t-BuG)-C-$NH_2$ (SEQ ID NO: 43) and (Mpa)-R-G-D-(Cha)-(t-BuG)-C-$NH_2$ (SEQ ID NO: 44) --.

Column 17,
Line 46, please delete "PMBHA" and replace therefore -- pMBHA --.

Column 18,
Line 9, please delete ""WATERS" and replace therefor -- ("WATERS --.
Line 41, please delete "vacuum nd" and replace therefor -- vacuum and --.

Column 23,
Line 19-20, please delete carriage return.

Column 24,
Line 48, please delete "in in ethanol" and replace therefor -- in 10% ethanol --.

UNITED STATES PATENT AND TRADEMARK OFFICE
CERTIFICATE OF CORRECTION

PATENT NO. : 5,807,819
DATED : September 15, 1998
INVENTOR(S) : Cheng et al.

It is certified that error appears in the above-identified patent and that said Letters Patent is hereby corrected as shown below:

<u>Column 28,</u>
Line 22, please delete "("TWEEN" and replace therefor -- ("TBS/TWEEN --.
Line 59, please delete "$\alpha_5\beta1$" and replace therefor -- $\alpha_5\beta_1$ --.

<u>Column 32,</u>
Line 52, please delete "(300-400." and replace therefor -- (300-400 --.

Signed and Sealed this

Twenty-second Day of January, 2002

*Attest:*

JAMES E. ROGAN
*Attesting Officer*  *Director of the United States Patent and Trademark Office*

SEQUENCE LISTING ( 1 ) GENERAL INFORMATION:

( i i i ) NUMBER OF SEQUENCES: 138

( 2 ) INFORMATION FOR SEQ ID NO:1:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:1:

Arg Gly Asp Asp Val
 1        5

( 2 ) INFORMATION FOR SEQ ID NO:2:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /note= "Amino acid is acetylated at
   N- terminal."

( i x ) FEATURE:
  ( A ) NAME/KEY: Peptide
  ( B ) LOCATION: 6
  ( D ) OTHER INFORMATION: /note= "Amino acid is amidated at
   C- terminal."

( x i ) SEQUENCE DESCRIPTION: SEQ ID NO:2:

Arg Gly Asp Asp Val Gly
 1        5

( 2 ) INFORMATION FOR SEQ ID NO:3:

( i ) SEQUENCE CHARACTERISTICS:
  ( A ) LENGTH: 6 amino acids
  ( B ) TYPE: amino acid
  ( D ) TOPOLOGY: circular ( i i ) MOLECULE TYPE: peptide ( i x ) FEATURE:
  ( A ) NAME/KEY: Peptide
  ( B ) LOCATION: 6
  ( D ) OTHER INFORMATION: /note= "Amino acid is amidated at
   C- terminal."

( x i ) SEQUENCE DESCRIPTION: SEQ ID NO:3:

Arg Gly Asp Asp Val Glu
 1        5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Gly  Arg  Gly  Asp  Ser  Pro
    1                        5

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Gly  Arg  Gly  Asp  Ser  Pro  Lys
    1                        5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Val  Thr  Arg  Gly  Asp  Val  Phe  Thr  Lys
    1                        5

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 7
        ( D ) OTHER INFORMATION: /note= "Amino acid is amidated at
            C- terminal."

( x i ) SEQUENCE DESCRIPTION: SEQ ID NO:7:

Gly  Arg  Gly  Asp  Asp  Val  Asp
    1                        5

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1

( D ) OTHER INFORMATION: /note= "Amino acid is acetylated at
N- terminal."

( i x ) FEATURE:
( A ) NAME/KEY: Peptide
( B ) LOCATION: 7
( D ) OTHER INFORMATION: /note= "Amino acid is amidated at
C- terminal."

( x i ) SEQUENCE DESCRIPTION: SEQ ID NO:8:

Cys Lys Gly Asp Asp Val Cys
1               5

( 2 ) INFORMATION FOR SEQ ID NO:9:

( i ) SEQUENCE CHARACTERISTICS:
( A ) LENGTH: 8 amino acids
( B ) TYPE: amino acid
( D ) TOPOLOGY: circular ( i i ) MOLECULE TYPE: peptide ( x i ) SEQUENCE DESCRIPTION: SEQ ID NO:9:

Gly Arg Gly Asp Ser Pro Asp Gly
1               5

( 2 ) INFORMATION FOR SEQ ID NO:10:

( i ) SEQUENCE CHARACTERISTICS:
( A ) LENGTH: 8 amino acids
( B ) TYPE: amino acid
( D ) TOPOLOGY: circular ( i i ) MOLECULE TYPE: peptide ( x i ) SEQUENCE DESCRIPTION: SEQ ID NO:10:

Gly Arg Gly Asp Ser Pro Asp Phe
1               5

( 2 ) INFORMATION FOR SEQ ID NO:11:

( i ) SEQUENCE CHARACTERISTICS:
( A ) LENGTH: 8 amino acids
( B ) TYPE: amino acid
( D ) TOPOLOGY: circular ( i i ) MOLECULE TYPE: peptide ( x i ) SEQUENCE DESCRIPTION: SEQ ID NO:11:

Phe Arg Gly Asp Ser Pro Glu Gly
1               5

( 2 ) INFORMATION FOR SEQ ID NO:12:

( i ) SEQUENCE CHARACTERISTICS:
( A ) LENGTH: 7 amino acids
( B ) TYPE: amino acid
( D ) TOPOLOGY: circular ( i i ) MOLECULE TYPE: peptide ( i x ) FEATURE:
( A ) NAME/KEY: Peptide
( B ) LOCATION: 7
( D ) OTHER INFORMATION: /note= "Amino acid is amidated at
C- terminal."

( x i ) SEQUENCE DESCRIPTION: SEQ ID NO:12:

Gly Arg Gly Asp Thr Phe Glu
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 6
        ( D ) OTHER INFORMATION: /note= "Amino acid is amidated at C- terminal."

( x i ) SEQUENCE DESCRIPTION: SEQ ID NO:13:

Arg Gly Asp Ser Pro Glu
    1               5

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 9
        ( D ) OTHER INFORMATION: /note= "Amino acid is amidated at C- terminal."

( x i ) SEQUENCE DESCRIPTION: SEQ ID NO:14:

Gly Arg Ala Arg Gly Asp Asn Pro Glu
    1               5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 6
        ( D ) OTHER INFORMATION: /note= "Amino acid is amidated at C- terminal."

( x i ) SEQUENCE DESCRIPTION: SEQ ID NO:15:

Arg Gly Asp Thr Pro Glu
    1               5

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:16:

Gly Arg Gly Asp Glu Pro Asp Gly
    1               5

( 2 ) INFORMATION FOR SEQ ID NO:17:

( i ) SEQUENCE CHARACTERISTICS:
    ( A ) LENGTH: 7 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at
        N- terminal."

( i x ) FEATURE:
    ( A ) NAME/KEY: Peptide
    ( B ) LOCATION: 7
    ( D ) OTHER INFORMATION: /note= "Amino acid is amidated at
        C- terminal."

( x i ) SEQUENCE DESCRIPTION: SEQ ID NO:17:

Cys  Arg  Gly  Asp  Asp  Val  Cys
1                      5

( 2 ) INFORMATION FOR SEQ ID NO:18:

( i ) SEQUENCE CHARACTERISTICS:
    ( A ) LENGTH: 9 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at
        N- terminal."

( i x ) FEATURE:
    ( A ) NAME/KEY: Peptide
    ( B ) LOCATION: 9
    ( D ) OTHER INFORMATION: /note= "Amino acid is amidated at
        C- terminal."

( x i ) SEQUENCE DESCRIPTION: SEQ ID NO:18:

Cys  Ile  Ala  Arg  Gly  Asp  Asp  Val  Cys
1                      5

( 2 ) INFORMATION FOR SEQ ID NO:19:

( i ) SEQUENCE CHARACTERISTICS:
    ( A ) LENGTH: 9 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at
        N- terminal."

( i x ) FEATURE:
    ( A ) NAME/KEY: Peptide
    ( B ) LOCATION: 9
    ( D ) OTHER INFORMATION: /note= "Amino acid is amidated at
        C- terminal."

( x i ) SEQUENCE DESCRIPTION: SEQ ID NO:19:

Cys  Glu  Pro  Arg  Gly  Asp  Asp  Val  Cys
1                      5

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            N- terminal."

( i x ) FEATURE:
        ( A ) NAME/KEY: Peptide
        ( B ) LOCATION: 9
        ( D ) OTHER INFORMATION: /note= "Amino acid is amidated at
            C- terminal."

( x i ) SEQUENCE DESCRIPTION: SEQ ID NO:20:

Cys  Glu  Ala  Arg  Gly  Asp  Asp  Val  Cys
  1                      5

( 2 ) INFORMATION FOR SEQ ID NO:21:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            N- terminal."

( i x ) FEATURE:
        ( A ) NAME/KEY: Peptide
        ( B ) LOCATION: 9
        ( D ) OTHER INFORMATION: /note= "Amino acid is amidated at
            C- terminal."

( x i ) SEQUENCE DESCRIPTION: SEQ ID NO:21:

Cys  Ala  Ala  Arg  Gly  Asp  Thr  Pro  Cys
  1                      5

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            N- terminal."

( i x ) FEATURE:
        ( A ) NAME/KEY: Peptide
        ( B ) LOCATION: 8
        ( D ) OTHER INFORMATION: /note= "Amino acid is amidated at
            C- terminal."

( x i ) SEQUENCE DESCRIPTION: SEQ ID NO:22:

Phe  Cys  Arg  Gly  Asp  Thr  Phe  Cys
  1                      5

(2) INFORMATION FOR SEQ ID NO:23:

(i) SEQUENCE CHARACTERISTICS:
  (A) LENGTH: 9 amino acids
  (B) TYPE: amino acid
  (D) TOPOLOGY: circular (ii) MOLECULE TYPE: peptide (ix) FEATURE:
  (A) NAME/KEY: Peptide
  (B) LOCATION: 1
  (D) OTHER INFORMATION: /note= "Amino acid is acetylated at N- terminal."

(ix) FEATURE:
  (A) NAME/KEY: Peptide
  (B) LOCATION: 9
  (D) OTHER INFORMATION: /note= "Amino acid is amidated at C- terminal."

(xi) SEQUENCE DESCRIPTION: SEQ ID NO:23:

```
Cys Ile Phe Arg Gly Asp Thr Phe Cys
1               5
```

(2) INFORMATION FOR SEQ ID NO:24:

(i) SEQUENCE CHARACTERISTICS:
  (A) LENGTH: 6 amino acids
  (B) TYPE: amino acid
  (D) TOPOLOGY: circular (ii) MOLECULE TYPE: peptide (ix) FEATURE:
  (A) NAME/KEY: Peptide
  (B) LOCATION: 1
  (D) OTHER INFORMATION: /note= "Amino acid is acetylated at N- terminal."

(ix) FEATURE:
  (A) NAME/KEY: Peptide
  (B) LOCATION: 6
  (D) OTHER INFORMATION: /note= "Amino acid is amidated at C- terminal."

(xi) SEQUENCE DESCRIPTION: SEQ ID NO:24:

```
Arg Gly Asp Asp Val Gly
1               5
```

(2) INFORMATION FOR SEQ ID NO:25:

(i) SEQUENCE CHARACTERISTICS:
  (A) LENGTH: 6 amino acids
  (B) TYPE: amino acid
  (D) TOPOLOGY: circular (ii) MOLECULE TYPE: peptide (ix) FEATURE:
  (A) NAME/KEY: Peptide
  (B) LOCATION: 6
  (D) OTHER INFORMATION: /note= "Amino acid is amidated at C- terminal."

(xi) SEQUENCE DESCRIPTION: SEQ ID NO:25:

```
Arg Gly Asp Asn Ile Glu
1               5
```

(2) INFORMATION FOR SEQ ID NO:26:

(i) SEQUENCE CHARACTERISTICS:
  (A) LENGTH: 9 amino acids (B) TYPE: amino acid
              (D) TOPOLOGY: circular (ii) MOLECULE TYPE: peptide (ix) FEATURE:
              (A) NAME/KEY: Peptide
              (B) LOCATION: 1
              (D) OTHER INFORMATION: /note= "Amino acid is acetylated at
                    N- terminal."

(ix) FEATURE:
              (A) NAME/KEY: Peptide
              (B) LOCATION: 9
              (D) OTHER INFORMATION: /note= "Amino acid is amidated at
                    C- terminal."

(xi) SEQUENCE DESCRIPTION: SEQ ID NO:26:

Ala  Cys  Arg  Gly  Asp  Asp  Val  Cys  Ala
    1                        5

(2) INFORMATION FOR SEQ ID NO:27:

(i) SEQUENCE CHARACTERISTICS:
              (A) LENGTH: 9 amino acids
              (B) TYPE: amino acid
              (D) TOPOLOGY: circular (ii) MOLECULE TYPE: peptide (ix) FEATURE:
              (A) NAME/KEY: Peptide
              (B) LOCATION: 1
              (D) OTHER INFORMATION: /note= "Amino acid is acetylated at
                    N- terminal."

(ix) FEATURE:
              (A) NAME/KEY: Peptide
              (B) LOCATION: 9
              (D) OTHER INFORMATION: /note= "Amino acid is amidated at
                    C- terminal."

(xi) SEQUENCE DESCRIPTION: SEQ ID NO:27:

Ala  Cys  Arg  Gly  Asp  Glu  Val  Cys  Ala
    1                        5

(2) INFORMATION FOR SEQ ID NO:28:

(i) SEQUENCE CHARACTERISTICS:
              (A) LENGTH: 4 amino acids
              (B) TYPE: amino acid
              (D) TOPOLOGY: linear (ii) MOLECULE TYPE: peptide (xi) SEQUENCE DESCRIPTION: SEQ ID NO:28:

Arg  Gly  Asp  Ser
    1

(2) INFORMATION FOR SEQ ID NO:29:

(i) SEQUENCE CHARACTERISTICS:
              (A) LENGTH: 6 amino acids
              (B) TYPE: amino acid
              (D) TOPOLOGY: linear (ii) MOLECULE TYPE: peptide (xi) SEQUENCE DESCRIPTION: SEQ ID NO:29:

Gly  Arg  Gly  Glu  Ser  Pro
    1                   5

( 2 ) INFORMATION FOR SEQ ID NO:30:

( i ) SEQUENCE CHARACTERISTICS:
　　　　( A ) LENGTH: 10 amino acids
　　　　( B ) TYPE: amino acid
　　　　( D ) TOPOLOGY: circular ( i i ) MOLECULE TYPE: peptide ( i x ) FEATURE:
　　　　( A ) NAME/KEY: Peptide
　　　　( B ) LOCATION: 2
　　　　( D ) OTHER INFORMATION: /note= "Xaa = Pen"

( i x ) FEATURE:
　　　　( A ) NAME/KEY: Peptide
　　　　( B ) LOCATION: 10
　　　　( D ) OTHER INFORMATION: /note= "Amino acid is amidated at
　　　　　　C- terminal."

( x i ) SEQUENCE DESCRIPTION: SEQ ID NO:30:

Gly  Xaa  Ala  Ala  Arg  Gly  Asp  Glu  Pro  Cys
1                   5                        10

( 2 ) INFORMATION FOR SEQ ID NO:31:

( i ) SEQUENCE CHARACTERISTICS:
　　　　( A ) LENGTH: 5 amino acids
　　　　( B ) TYPE: amino acid
　　　　( D ) TOPOLOGY: circular ( i i ) MOLECULE TYPE: peptide ( i x ) FEATURE:
　　　　( A ) NAME/KEY: Peptide
　　　　( B ) LOCATION: 5
　　　　( D ) OTHER INFORMATION: /note= "Xaa is Tic"

( x i ) SEQUENCE DESCRIPTION: SEQ ID NO:31:

Arg  Gly  Asp  Asn  Xaa
1                   5

( 2 ) INFORMATION FOR SEQ ID NO:32:

( i ) SEQUENCE CHARACTERISTICS:
　　　　( A ) LENGTH: 10 amino acids
　　　　( B ) TYPE: amino acid
　　　　( D ) TOPOLOGY: linear ( i x ) FEATURE:
　　　　( A ) NAME/KEY: Peptide
　　　　( B ) LOCATION: 1
　　　　( D ) OTHER INFORMATION: /note= "Xaa = R1R2, (wherein R1 is
　　　　　　an H or alkyl group and R2 is an H, alkyl, CH3CO,
　　　　　　alkyl-CO or phenyl-CO group) or 0 to 10 amino acids,
　　　　　　which can be protected by acetylation at the N-terminus."

( i x ) FEATURE:
　　　　( A ) NAME/KEY: Peptide
　　　　( B ) LOCATION: 2
　　　　( D ) OTHER INFORMATION: /note= "Xaa = 0 or 1 amino acid"

( i x ) FEATURE:
　　　　( A ) NAME/KEY: Peptide
　　　　( B ) LOCATION: 3
　　　　( D ) OTHER INFORMATION: /note= "Xaa = 0, 1 or 2 amino
　　　　　　acids"

( i x ) FEATURE:
　　　　( A ) NAME/KEY: Peptide
　　　　( B ) LOCATION: 4
　　　　( D ) OTHER INFORMATION: /note= "Xaa = a positively charged
　　　　　　amino acid"

( i x ) FEATURE:
　　　　( A ) NAME/KEY: Peptide (B) LOCATION: 7
                    (D) OTHER INFORMATION: /note= "Xaa = an amino acid which
                        can provide a hydrogen bond interaction with an
                        integrin receptor"

(ix) FEATURE:
                    (A) NAME/KEY: Peptide
                    (B) LOCATION: 8
                    (D) OTHER INFORMATION: /note= "Xaa = an amino acid that
                        has the characteristics of hydrophobicity or
                        conformational constraint"

(ix) FEATURE:
                    (A) NAME/KEY: Peptide
                    (B) LOCATION: 9
                    (D) OTHER INFORMATION: /note= "Xaa = a residue capable of
                        forming a bond with a bridging amino acid of Xaa at
                        position 2, or with Xaa at position 3 when Xaa at
                        position 2 is 0, or with Xaa at position 4 when Xaa
                        at position 2 and Xaa at position 3 are 0, to
                        conformationally restrain the peptide."

(ix) FEATURE:
                    (A) NAME/KEY: Peptide
                    (B) LOCATION: 10
                    (D) OTHER INFORMATION: /note= "Xaa = -NR3R4, (wherein R3
                        is an H or alkyl group and R4 is an H or alkyl
                        group) or - OR5 (wherein R5 is an H or alkyl group)
                        or 0 to 10 amino acids, which can be protected as an
                        amide at the C-terminus, and wherein when Xaa at
                        position 7 is serine and Xaa at position 8 is proline,
                        Xaa at position 3 is 0 or 2 amino acids."

(xi) SEQUENCE DESCRIPTION: SEQ ID NO:32:

Xaa   Xaa   Xaa   Xaa   Gly   Asp   Xaa   Xaa   Xaa   Xaa
    1                       5                             10

(2) INFORMATION FOR SEQ ID NO:33:

(i) SEQUENCE CHARACTERISTICS:
                    (A) LENGTH: 10 amino acids
                    (B) TYPE: amino acid
                    (D) TOPOLOGY: linear (ix) FEATURE:
                    (A) NAME/KEY: Peptide
                    (B) LOCATION: 1
                    (D) OTHER INFORMATION: /note= "Xaa = R1R2, (wherein R1 is
                        an H or alkyl group and R2 is an H, alkyl, CH3CO,
                        alkyl-CO or phenyl-CO group) or 0 to 10 amino acids,
                        which can be protected by acetylation at the N-terminus."

(ix) FEATURE:
                    (A) NAME/KEY: Peptide
                    (B) LOCATION: 2
                    (D) OTHER INFORMATION: /note= "Xaa = 0 or 1 amino acid"

(ix) FEATURE:
                    (A) NAME/KEY: Peptide
                    (B) LOCATION: 3
                    (D) OTHER INFORMATION: /note= "Xaa = 0, 1 or 2 amino
                        acids"

(ix) FEATURE:
                    (A) NAME/KEY: Peptide
                    (B) LOCATION: 4
                    (D) OTHER INFORMATION: /note= "Xaa = a positively charged
                        amino acid"

(ix) FEATURE:
                    (A) NAME/KEY: Peptide
                    (B) LOCATION: 7
                    (D) OTHER INFORMATION: /note= "Xaa = an amino acid that
                        provides an ionic or similar interaction with an
                        integrin receptor, or is Msa, Psa or Tfsa."

(ix) FEATURE:
                    (A) NAME/KEY: Peptide (B) LOCATION: 8
(D) OTHER INFORMATION: /note= "Xaa = an amino acid having an aliphatic side chain or is an aliphatic non-natural amino acid that is hydrophobic, or is Thr."

(ix) FEATURE:
(A) NAME/KEY: Peptide
(B) LOCATION: 9
(D) OTHER INFORMATION: /note= "Xaa = a residue capable of forming a bond with a bridging amino acid of Xaa at position 2, or with Xaa at position 3 when Xaa at position 2 is 0, or with Xaa at position 4 when Xaa at position 2 and Xaa at position 3 are 0, to conformationally restrain the peptide."

(ix) FEATURE:
(A) NAME/KEY: Peptide
(B) LOCATION: 10
(D) OTHER INFORMATION: /note= "Xaa = -NR3R4, (wherein R3 is an H or alkyl group and R4 is an H or alkyl group) or - OR5 (wherein R5 is an H or alkyl group) or 0 to 10 amino acids, which can be protected as an amide at the C-terminus."

(xi) SEQUENCE DESCRIPTION: SEQ ID NO:33:

Xaa Xaa Xaa Xaa Gly Asp Xaa Xaa Xaa Xaa
1               5                   10

(2) INFORMATION FOR SEQ ID NO:34:

(i) SEQUENCE CHARACTERISTICS:
(A) LENGTH: 7 amino acids
(B) TYPE: amino acid
(D) TOPOLOGY: circular (ii) MOLECULE TYPE: peptide (ix) FEATURE:
(A) NAME/KEY: Peptide
(B) LOCATION: 2
(D) OTHER INFORMATION: /note= "Xaa is Pmc"

(xi) SEQUENCE DESCRIPTION: SEQ ID NO:34:

Gly Xaa Arg Gly Asp Cys Ala
1               5

(2) INFORMATION FOR SEQ ID NO:35:

(i) SEQUENCE CHARACTERISTICS:
(A) LENGTH: 10 amino acids
(B) TYPE: amino acid
(D) TOPOLOGY: linear (ii) MOLECULE TYPE: peptide (ix) FEATURE:
(A) NAME/KEY: Peptide
(B) LOCATION: 2
(D) OTHER INFORMATION: /note= "Xaa is Pen"

(xi) SEQUENCE DESCRIPTION: SEQ ID NO:35:

Gly Xaa Gly Arg Gly Asp Asn Tyr Cys Ala
1               5                   10

(2) INFORMATION FOR SEQ ID NO:36:

(i) SEQUENCE CHARACTERISTICS:
(A) LENGTH: 11 amino acids
(B) TYPE: amino acid
(D) TOPOLOGY: circular (ii) MOLECULE TYPE: peptide (ix) FEATURE:

(A) NAME/KEY: Peptide
(B) LOCATION: 2
(D) OTHER INFORMATION: /note= "Xaa is Pen"

(xi) SEQUENCE DESCRIPTION: SEQ ID NO:36:

Gly Xaa Gly Glu Arg Gly Asp Asn Tyr Cys Ala
1               5                   10

(2) INFORMATION FOR SEQ ID NO:37:

(i) SEQUENCE CHARACTERISTICS:
(A) LENGTH: 11 amino acids
(B) TYPE: amino acid
(D) TOPOLOGY: circular (ii) MOLECULE TYPE: peptide (ix) FEATURE:
(A) NAME/KEY: Peptide
(B) LOCATION: 2
(D) OTHER INFORMATION: /note= "Xaa is Pen"

(ix) FEATURE:
(A) NAME/KEY: Peptide
(B) LOCATION: 11
(D) OTHER INFORMATION: /note= "Amino acid is amidated at the C- terminal."

(xi) SEQUENCE DESCRIPTION: SEQ ID NO:37:

Gly Xaa Ala Ala Arg Gly Asp Val Pro Cys Ala
1               5                   10

(2) INFORMATION FOR SEQ ID NO:38:

(i) SEQUENCE CHARACTERISTICS:
(A) LENGTH: 10 amino acids
(B) TYPE: amino acid
(D) TOPOLOGY: circular (ii) MOLECULE TYPE: peptide (ix) FEATURE:
(A) NAME/KEY: Peptide
(B) LOCATION: 2
(D) OTHER INFORMATION: /note= "Xaa is Pen"

(ix) FEATURE:
(A) NAME/KEY: Peptide
(B) LOCATION: 10
(D) OTHER INFORMATION: /note= "Amino acid is amidated at the C- terminal."

(xi) SEQUENCE DESCRIPTION: SEQ ID NO:38:

Gly Xaa Glu Leu Arg Gly Asp Gly Trp Cys
1               5                   10

(2) INFORMATION FOR SEQ ID NO:39:

(i) SEQUENCE CHARACTERISTICS:
(A) LENGTH: 10 amino acids
(B) TYPE: amino acid
(D) TOPOLOGY: circular (ii) MOLECULE TYPE: peptide (ix) FEATURE:
(A) NAME/KEY: Peptide
(B) LOCATION: 2
(D) OTHER INFORMATION: /note= "Xaa is Pen"

(ix) FEATURE:
(A) NAME/KEY: Peptide
(B) LOCATION: 10
(D) OTHER INFORMATION: /note= "Amino acid is amidated at the C-terminal."

( x i ) SEQUENCE DESCRIPTION: SEQ ID NO:39:

Gly Xaa Gly Phe Arg Gly Asp Glu Pro Cys
1               5                       10

( 2 ) INFORMATION FOR SEQ ID NO:40:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:40:

Lys Xaa Gly Phe Arg Gly Asp Glu Pro Cys Arg
1               5                       10

( 2 ) INFORMATION FOR SEQ ID NO:41:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:41:

Lys Xaa Gly Phe Arg Gly Asp Asp Pro Cys Arg
1               5                       10

( 2 ) INFORMATION FOR SEQ ID NO:42:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N-terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 7
        ( D ) OTHER INFORMATION: /note= "Xaa is Orn"

( i x ) FEATURE:
        ( A ) NAME/KEY: Peptide
        ( B ) LOCATION: 9
        ( D ) OTHER INFORMATION: /note= "Amino acid is amidated at
            the C-terminal."

( x i ) SEQUENCE DESCRIPTION: SEQ ID NO:42:

Xaa Ala Ala Arg Gly Asp Xaa Pro Cys
1               5

( 2 ) INFORMATION FOR SEQ ID NO:43:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is (Mpa)"

( i x ) FEATURE:
        ( A ) NAME/KEY: Peptide
        ( B ) LOCATION: 5
        ( D ) OTHER INFORMATION: /note= "Xaa is (YOMe)"

( i x ) FEATURE:
        ( A ) NAME/KEY: Peptide
        ( B ) LOCATION: 6
        ( D ) OTHER INFORMATION: /note= "Xaa is (tBuG)"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:43:

Xaa Arg Gly Asp Xaa Xaa Cys
1               5

( 2 ) INFORMATION FOR SEQ ID NO:44:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is (Mpa)"

( i x ) FEATURE:
        ( A ) NAME/KEY: Peptide
        ( B ) LOCATION: 5
        ( D ) OTHER INFORMATION: /note= "Xaa is (Cha)"

( i x ) FEATURE:
        ( A ) NAME/KEY: Peptide
        ( B ) LOCATION: 6
        ( D ) OTHER INFORMATION: /note= "Xaa is (tBuG)"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:44:

Xaa Arg Gly Asp Xaa Xaa Cys
1               5

( 2 ) INFORMATION FOR SEQ ID NO:45:

( i ) SEQUENCE CHARACTERISTICS:

(A) LENGTH: 7 amino acids
        (B) TYPE: amino acid
        (D) TOPOLOGY: circular (ii) MOLECULE TYPE: peptide (ix) FEATURE:
        (A) NAME/KEY: Peptide
        (B) LOCATION: 1
        (D) OTHER INFORMATION: /note= "Amino acid is acetylated at
            the N- terminal."

(ix) FEATURE:
        (A) NAME/KEY: Peptide
        (B) LOCATION: 6
        (D) OTHER INFORMATION: /note= "Xaa is (Tic)"

(ix) FEATURE:
        (A) NAME/KEY: Peptide
        (B) LOCATION: 7
        (D) OTHER INFORMATION: /note= "Amino acid is amidated at
            the C- terminal."

(xi) SEQUENCE DESCRIPTION: SEQ ID NO:45:

Cys   Arg   Gly   Asp   Ser   Xaa   Cys
    1                       5

(2) INFORMATION FOR SEQ ID NO:46:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 2
        (D) OTHER INFORMATION: /note= "Xaa is Pen"

(xi) SEQUENCE DESCRIPTION: SEQ ID NO:46:

Gly   Xaa   Gly   Arg   Gly   Asp   Ser   Pro   Cys   Ala
    1                       5                             10

(2) INFORMATION FOR SEQ ID NO:47:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Peptide
        (B) LOCATION: 4
        (D) OTHER INFORMATION: /note= "Xaa is (YOMe)"

(ix) FEATURE:
        (A) NAME/KEY: Peptide
        (B) LOCATION: 6
        (D) OTHER INFORMATION: /note= "Amino acid is amidated at
            the C- terminal."

(xi) SEQUENCE DESCRIPTION: SEQ ID NO:47:

Arg   Gly   Asp   Xaa   Arg   Glu
    1                       5

(2) INFORMATION FOR SEQ ID NO:48:

(i) SEQUENCE CHARACTERISTICS:
        (A) LENGTH: 11 amino acids
        (B) TYPE: amino acid (D) TOPOLOGY: circular (ii) MOLECULE TYPE: peptide (ix) FEATURE:
 (A) NAME/KEY: Peptide
 (B) LOCATION: 2
 (D) OTHER INFORMATION: /note= "Xaa is Pen"

(xi) SEQUENCE DESCRIPTION: SEQ ID NO:48:

Gly Xaa Arg Ala Arg Gly Asp Asp Leu Cys Ala
1               5                   10

(2) INFORMATION FOR SEQ ID NO:49:

(i) SEQUENCE CHARACTERISTICS:
  (A) LENGTH: 11 amino acids
  (B) TYPE: amino acid
  (D) TOPOLOGY: circular (ii) MOLECULE TYPE: peptide (ix) FEATURE:
  (A) NAME/KEY: Peptide
  (B) LOCATION: 2
  (D) OTHER INFORMATION: /note= "Xaa is Pen"

(ix) FEATURE:
  (A) NAME/KEY: Peptide
  (B) LOCATION: 9
  (D) OTHER INFORMATION: /note= "Xaa is nL"

(xi) SEQUENCE DESCRIPTION: SEQ ID NO:49:

Gly Xaa Arg Ala Arg Gly Asp Asp Xaa Cys Ala
1               5                   10

(2) INFORMATION FOR SEQ ID NO:50:

(i) SEQUENCE CHARACTERISTICS:
  (A) LENGTH: 11 amino acids
  (B) TYPE: amino acid
  (D) TOPOLOGY: circular (ii) MOLECULE TYPE: peptide (ix) FEATURE:
  (A) NAME/KEY: Peptide
  (B) LOCATION: 2
  (D) OTHER INFORMATION: /note= "Xaa is Pen"

(xi) SEQUENCE DESCRIPTION: SEQ ID NO:50:

Gly Xaa Ala Ala Arg Gly Asp Asp Ile Cys Ala
1               5                   10

(2) INFORMATION FOR SEQ ID NO:51:

(i) SEQUENCE CHARACTERISTICS:
  (A) LENGTH: 9 amino acids
  (B) TYPE: amino acid
  (D) TOPOLOGY: circular (ii) MOLECULE TYPE: peptide (ix) FEATURE:
  (A) NAME/KEY: Peptide
  (B) LOCATION: 1
  (D) OTHER INFORMATION: /note= "Xaa is Beta-Ala"

(ix) FEATURE:
  (A) NAME/KEY: Peptide
  (B) LOCATION: 9
  (D) OTHER INFORMATION: /note= "Amino acid is amidated at the C- terminal."

( x i ) SEQUENCE DESCRIPTION: SEQ ID NO:51:

Xaa  Arg  Ala  Arg  Gly  Asp  Asn  Pro  Asp
1                       5

( 2 ) INFORMATION FOR SEQ ID NO:52:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
        the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 8
        ( D ) OTHER INFORMATION: /note= "Xaa is Pgl"

( i x ) FEATURE:
        ( A ) NAME/KEY: Peptide
        ( B ) LOCATION: 9
        ( D ) OTHER INFORMATION: /note= "Amino acid is amidated at
        the C- terminal."

( x i ) SEQUENCE DESCRIPTION: SEQ ID NO:52:

Xaa  Phe  Ala  Arg  Gly  Asp  Asn  Xaa  Cys
1                       5

( 2 ) INFORMATION FOR SEQ ID NO:53:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
        the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 3
        ( D ) OTHER INFORMATION: /note= "Xaa is (p-Cl-F)"

( i x ) FEATURE:
        ( A ) NAME/KEY: Peptide
        ( B ) LOCATION: 9
        ( D ) OTHER INFORMATION: /note= "Amino acid is amidated at
        the C- terminal."

( x i ) SEQUENCE DESCRIPTION: SEQ ID NO:53:

Xaa  Ile  Xaa  Arg  Gly  Asp  Thr  Phe  Cys
1                       5

( 2 ) INFORMATION FOR SEQ ID NO:54:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 5
        ( D ) OTHER INFORMATION: /note= "Xaa is Tic"

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:54:

```
Arg  Gly  Asp  Ser  Xaa  Glu
1                   5
```

( 2 ) INFORMATION FOR SEQ ID NO:55:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:55:

```
Gly  Xaa  Gly  His  Arg  Gly  Asp  Ser  Pro  Cys  Ala
1                   5                        10
```

( 2 ) INFORMATION FOR SEQ ID NO:56:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:56:

```
Gly  Xaa  Arg  Ala  Arg  Gly  Asp  Asn  Pro  Cys  Ala
1                   5                        10
```

( 2 ) INFORMATION FOR SEQ ID NO:57:

( i ) SEQUENCE CHARACTERISTICS:
        ( A ) LENGTH: 8 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is Pmp"

( i x ) FEATURE:
    ( A ) NAME/KEY: Peptide
    ( B ) LOCATION: 7
    ( D ) OTHER INFORMATION: /note= "Xaa is Pen"

( x i ) SEQUENCE DESCRIPTION: SEQ ID NO:57:

Xaa Arg Gly Asp Ser Pro Xaa Gly
1                      5

( 2 ) INFORMATION FOR SEQ ID NO:58:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
              the N- terminal."

( i x ) FEATURE:
        ( A ) NAME/KEY: Peptide
        ( B ) LOCATION: 7
        ( D ) OTHER INFORMATION: /note= "Xaa is (YOMe)"

( i x ) FEATURE:
        ( A ) NAME/KEY: Peptide
        ( B ) LOCATION: 9
        ( D ) OTHER INFORMATION: /note= "Amino acid is amidated at
              the C- terminal."

( x i ) SEQUENCE DESCRIPTION: SEQ ID NO:58:

Cys Asn Pro Arg Gly Asp Xaa Arg Cys
1                      5

( 2 ) INFORMATION FOR SEQ ID NO:59:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:59:

Gly Xaa Ala Ala Arg Gly Asp Asn Pro Cys Ala
1                      5                      10

( 2 ) INFORMATION FOR SEQ ID NO:60:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:60:

Gly Xaa Ile Phe Arg Gly Asp Thr Phe Cys Ala ( 2 ) INFORMATION FOR SEQ ID NO:61:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:61:

Gly Xaa Ala Ala Arg Gly Asp Ser Pro Cys Ala
    1                5                      10

( 2 ) INFORMATION FOR SEQ ID NO:62:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:62:

Gly Xaa Ile Ala Arg Gly Asp Asp Leu Cys Ala
    1                5                      10

( 2 ) INFORMATION FOR SEQ ID NO:63:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 8
        ( D ) OTHER INFORMATION: /note= "Xaa is (dhP)"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:63:

Xaa Ala Ala Arg Gly Asp Asn Xaa Cys
    1                5

( 2 ) INFORMATION FOR SEQ ID NO:64:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 8
        ( D ) OTHER INFORMATION: /note= "Xaa is (Tic)"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:64:

Cys  Ala  Ala  Arg  Gly  Asp  Asn  Xaa  Cys
   1                           5

( 2 ) INFORMATION FOR SEQ ID NO:65:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:65:

Gly  Xaa  Arg  Ala  Arg  Gly  Asp  Asp  Val  Cys  Ala
   1                           5                                        10

( 2 ) INFORMATION FOR SEQ ID NO:66:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:66:

```
Xaa Phe Ala Arg Gly Asp Asn Pro Cys
 1           5
```

( 2 ) INFORMATION FOR SEQ ID NO:67:

( i ) SEQUENCE CHARACTERISTICS:
        ( A ) LENGTH: 11 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:67:

```
Gly Xaa Glu Ala Arg Gly Asp Asn Pro Cys Ala
 1           5                   1 0
```

( 2 ) INFORMATION FOR SEQ ID NO:68:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 7
        ( D ) OTHER INFORMATION: /note= "Xaa is Pen"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:68:

```
Cys Arg Gly Asp Asn Pro Xaa
 1           5
```

( 2 ) INFORMATION FOR SEQ ID NO:69:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 9
        ( D ) OTHER INFORMATION: /note= "Amino acid is amidated at the C- terminal."

(x i) SEQUENCE DESCRIPTION: SEQ ID NO:69:

Xaa Ala Ala Arg Gly Asp Asn Ile Cys
1               5

(2) INFORMATION FOR SEQ ID NO:70:

(i) SEQUENCE CHARACTERISTICS:
        (A) LENGTH: 9 amino acids
        (B) TYPE: amino acid
        (D) TOPOLOGY: circular (i i) MOLECULE TYPE: peptide (i x) FEATURE:
        (A) NAME/KEY: Peptide
        (B) LOCATION: 1
        (D) OTHER INFORMATION: /note= "Amino acid is acetylated at
            the N- terminal."

(i x) FEATURE:
        (A) NAME/KEY: Peptide
        (B) LOCATION: 1
        (D) OTHER INFORMATION: /note= "Xaa is Pen"

(i x) FEATURE:
        (A) NAME/KEY: Peptide
        (B) LOCATION: 8
        (D) OTHER INFORMATION: /note= "Xaa is (Tic)"

(i x) FEATURE:
        (A) NAME/KEY: Peptide
        (B) LOCATION: 9
        (D) OTHER INFORMATION: /note= "Amino acid is amidated at
            the C- terminal."

(x i) SEQUENCE DESCRIPTION: SEQ ID NO:70:

Xaa Ala Ala Arg Gly Asp Asn Xaa Cys
1               5

(2) INFORMATION FOR SEQ ID NO:71:

(i) SEQUENCE CHARACTERISTICS:
        (A) LENGTH: 9 amino acids
        (B) TYPE: amino acid
        (D) TOPOLOGY: circular (i i) MOLECULE TYPE: peptide (i x) FEATURE:
        (A) NAME/KEY: Peptide
        (B) LOCATION: 1
        (D) OTHER INFORMATION: /note= "Amino acid is acetylated at
            the N- terminal."

(i x) FEATURE:
        (A) NAME/KEY: Peptide
        (B) LOCATION: 1
        (D) OTHER INFORMATION: /note= "Xaa is Pen"

(i x) FEATURE:
        (A) NAME/KEY: Peptide
        (B) LOCATION: 9
        (D) OTHER INFORMATION: /note= "Amino acid is amidated at
            the C- terminal."

(x i) SEQUENCE DESCRIPTION: SEQ ID NO:71:

Xaa Thr Ala Arg Gly Asp Asn Pro Cys
1               5

(2) INFORMATION FOR SEQ ID NO:72:

(i) SEQUENCE CHARACTERISTICS:

( A ) LENGTH: 11 amino acids
             ( B ) TYPE: amino acid
             ( D ) TOPOLOGY: circular ( i i ) MOLECULE TYPE: peptide ( i x ) FEATURE:
             ( A ) NAME/KEY: Peptide
             ( B ) LOCATION: 2
             ( D ) OTHER INFORMATION: /note= "Xaa is Pen"

( i x ) FEATURE:
             ( A ) NAME/KEY: Peptide
             ( B ) LOCATION: 11
             ( D ) OTHER INFORMATION: /note= "Amino acid is amidated at
                   the C- terminal."

( x i ) SEQUENCE DESCRIPTION: SEQ ID NO:72:

Gly  Xaa  Ala  Ala  Arg  Gly  Asp  Asp  Val  Cys  Ala
    1                   5                        10

( 2 ) INFORMATION FOR SEQ ID NO:73:

( i ) SEQUENCE CHARACTERISTICS:
             ( A ) LENGTH: 9 amino acids
             ( B ) TYPE: amino acid
             ( D ) TOPOLOGY: circular ( i i ) MOLECULE TYPE: peptide ( i x ) FEATURE:
             ( A ) NAME/KEY: Peptide
             ( B ) LOCATION: 1
             ( D ) OTHER INFORMATION: /note= "Amino acid is acetylated at
                   the N- terminal."

( i x ) FEATURE:
             ( A ) NAME/KEY: Peptide
             ( B ) LOCATION: 8
             ( D ) OTHER INFORMATION: /note= "Xaa is (Tic)"

( i x ) FEATURE:
             ( A ) NAME/KEY: Peptide
             ( B ) LOCATION: 9
             ( D ) OTHER INFORMATION: /note= "Amino acid is amidated at
                   the C- terminal."

( x i ) SEQUENCE DESCRIPTION: SEQ ID NO:73:

Cys  Ala  Ala  Arg  Gly  Asp  Tyr  Xaa  Cys
    1                   5

( 2 ) INFORMATION FOR SEQ ID NO:74:

( i ) SEQUENCE CHARACTERISTICS:
             ( A ) LENGTH: 9 amino acids
             ( B ) TYPE: amino acid
             ( D ) TOPOLOGY: circular ( i i ) MOLECULE TYPE: peptide ( i x ) FEATURE:
             ( A ) NAME/KEY: Peptide
             ( B ) LOCATION: 1
             ( D ) OTHER INFORMATION: /note= "Amino acid is acetylated at
                   the N- terminal."

( i x ) FEATURE:
             ( A ) NAME/KEY: Peptide
             ( B ) LOCATION: 1
             ( D ) OTHER INFORMATION: /note= "Xaa is Pen"

( i x ) FEATURE:
             ( A ) NAME/KEY: Peptide
             ( B ) LOCATION: 9
             ( D ) OTHER INFORMATION: /note= "Amino acid is amidated at
                   the C- terminal."

( x i ) SEQUENCE DESCRIPTION: SEQ ID NO:74:

Xaa Phe Ala Arg Gly Asp Ser Pro Cys
1                   5

( 2 ) INFORMATION FOR SEQ ID NO:75:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 2
        ( D ) OTHER INFORMATION: /note= "Xaa is (YOMe)"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:75:

Xaa Xaa Ala Arg Gly Asp Asn Pro Cys
1                   5

( 2 ) INFORMATION FOR SEQ ID NO:76:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is (p-Cl-F)"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:76:

Xaa Arg Gly Asp Thr Pro Asp
1                   5

( 2 ) INFORMATION FOR SEQ ID NO:77:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:

(A) NAME/KEY: Peptide
            (B) LOCATION: 1
            (D) OTHER INFORMATION: /note= "Amino acid is acetylated at
                the N- terminal."

(ix) FEATURE:
            (A) NAME/KEY: Peptide
            (B) LOCATION: 1
            (D) OTHER INFORMATION: /note= "Xaa is Pen"

(ix) FEATURE:
            (A) NAME/KEY: Peptide
            (B) LOCATION: 8
            (D) OTHER INFORMATION: /note= "Xaa is (Tic)"

(ix) FEATURE:
            (A) NAME/KEY: Peptide
            (B) LOCATION: 9
            (D) OTHER INFORMATION: /note= "Amino acid is amidated at
                the C- terminal."

(xi) SEQUENCE DESCRIPTION: SEQ ID NO:77:

Xaa  Phe  Ala  Arg  Gly  Asp  Asn  Xaa  Cys
    1                   5

(2) INFORMATION FOR SEQ ID NO:78:

(i) SEQUENCE CHARACTERISTICS:
            (A) LENGTH: 7 amino acids
            (B) TYPE: amino acid
            (D) TOPOLOGY: circular (ii) MOLECULE TYPE: peptide (ix) FEATURE:
            (A) NAME/KEY: Peptide
            (B) LOCATION: 1
            (D) OTHER INFORMATION: /note= "Amino acid is acetylated at
                the N- terminal."

(ix) FEATURE:
            (A) NAME/KEY: Peptide
            (B) LOCATION: 7
            (D) OTHER INFORMATION: /note= "Amino acid is amidated at
                the C- terminal."

(xi) SEQUENCE DESCRIPTION: SEQ ID NO:78:

Cys  Arg  Gly  Asp  Ser  Pro  Cys
    1                   5

(2) INFORMATION FOR SEQ ID NO:79:

(i) SEQUENCE CHARACTERISTICS:
            (A) LENGTH: 10 amino acids
            (B) TYPE: amino acid
            (D) TOPOLOGY: circular (ii) MOLECULE TYPE: peptide (ix) FEATURE:
            (A) NAME/KEY: Peptide
            (B) LOCATION: 2
            (D) OTHER INFORMATION: /note= "Xaa is Pen"

(ix) FEATURE:
            (A) NAME/KEY: Peptide
            (B) LOCATION: 10
            (D) OTHER INFORMATION: /note= "Amino acid is amidated at
                the C- terminal."

(xi) SEQUENCE DESCRIPTION: SEQ ID NO:79:

Gly  Xaa  Ala  Ala  Arg  Gly  Asp  Asp  Thr  Cys
    1                   5                        10

( 2 ) INFORMATION FOR SEQ ID NO:80:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 2
        ( D ) OTHER INFORMATION: /note= "Xaa is (YOMe)"

( i x ) FEATURE:
        ( A ) NAME/KEY: Peptide
        ( B ) LOCATION: 8
        ( D ) OTHER INFORMATION: /note= "Xaa is (Tic)"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:80:

Xaa  Xaa  Ala  Arg  Gly  Asp  Asn  Xaa  Cys
    1                            5

( 2 ) INFORMATION FOR SEQ ID NO:81:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is Mpa"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:81:

Xaa  Arg  Gly  Asp  Asp  Val  Cys
    1                        5

( 2 ) INFORMATION FOR SEQ ID NO:82:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1

(D) OTHER INFORMATION: /note= "Amino acid is acetylated at
the N- terminal."

(ix) FEATURE:
(A) NAME/KEY: Peptide
(B) LOCATION: 1
(D) OTHER INFORMATION: /note= "Xaa is Pen"

(ix) FEATURE:
(A) NAME/KEY: Peptide
(B) LOCATION: 8
(D) OTHER INFORMATION: /note= "Xaa is (Tic)"

(ix) FEATURE:
(A) NAME/KEY: Peptide
(B) LOCATION: 9
(D) OTHER INFORMATION: /note= "Amino acid is amidated at
the C- terminal."

(xi) SEQUENCE DESCRIPTION: SEQ ID NO:82:

Xaa Phe Ala Arg Gly Asp Ser Xaa Cys
1               5

(2) INFORMATION FOR SEQ ID NO:83:

(i) SEQUENCE CHARACTERISTICS:
(A) LENGTH: 9 amino acids
(B) TYPE: amino acid
(D) TOPOLOGY: circular (ii) MOLECULE TYPE: peptide (ix) FEATURE:
(A) NAME/KEY: Peptide
(B) LOCATION: 1
(D) OTHER INFORMATION: /note= "Amino acid is acetylated at
the N- terminal."

(ix) FEATURE:
(A) NAME/KEY: Peptide
(B) LOCATION: 8
(D) OTHER INFORMATION: /note= "Xaa is (Tic)"

(ix) FEATURE:
(A) NAME/KEY: Peptide
(B) LOCATION: 9
(D) OTHER INFORMATION: /note= "Amino acid is amidated at
the C- terminal."

(xi) SEQUENCE DESCRIPTION: SEQ ID NO:83:

Cys Ala Ala Arg Gly Asp Ser Xaa Cys
1               5

(2) INFORMATION FOR SEQ ID NO:84:

(i) SEQUENCE CHARACTERISTICS:
(A) LENGTH: 9 amino acids
(B) TYPE: amino acid
(D) TOPOLOGY: circular (ii) MOLECULE TYPE: peptide (ix) FEATURE:
(A) NAME/KEY: Peptide
(B) LOCATION: 1
(D) OTHER INFORMATION: /note= "Xaa is beta-Alanine"

(ix) FEATURE:
(A) NAME/KEY: Peptide
(B) LOCATION: 8
(D) OTHER INFORMATION: /note= "Xaa is (Tic)"

(ix) FEATURE:
(A) NAME/KEY: Peptide
(B) LOCATION: 9
(D) OTHER INFORMATION: /note= "Amino acid is amidated at the C- terminal."

(x i) SEQUENCE DESCRIPTION: SEQ ID NO:84:

Xaa Ala Ala Arg Gly Asp Asn Xaa Asp
1               5

(2) INFORMATION FOR SEQ ID NO:85:

(i) SEQUENCE CHARACTERISTICS:
      (A) LENGTH: 9 amino acids
      (B) TYPE: amino acid
      (D) TOPOLOGY: circular (i i) MOLECULE TYPE: peptide (i x) FEATURE:
      (A) NAME/KEY: Peptide
      (B) LOCATION: 1
      (D) OTHER INFORMATION: /note= "Amino acid is acetylated at
         the N- terminal."

(i x) FEATURE:
      (A) NAME/KEY: Peptide
      (B) LOCATION: 8
      (D) OTHER INFORMATION: /note= "Xaa is (Tic)"

(i x) FEATURE:
      (A) NAME/KEY: Peptide
      (B) LOCATION: 9
      (D) OTHER INFORMATION: /note= "Amino acid is amidated at
         the C- terminal."

(x i) SEQUENCE DESCRIPTION: SEQ ID NO:85:

Cys Ala Ala Arg Gly Asp Thr Xaa Cys
1               5

(2) INFORMATION FOR SEQ ID NO:86:

(i) SEQUENCE CHARACTERISTICS:
      (A) LENGTH: 11 amino acids
      (B) TYPE: amino acid
      (D) TOPOLOGY: circular (i i) MOLECULE TYPE: peptide (i x) FEATURE:
      (A) NAME/KEY: Peptide
      (B) LOCATION: 9
      (D) OTHER INFORMATION: /note= "Xaa is (Tic)"

(i x) FEATURE:
      (A) NAME/KEY: Peptide
      (B) LOCATION: 11
      (D) OTHER INFORMATION: /note= "Amino acid is amidated at
         the C- terminal."

(x i) SEQUENCE DESCRIPTION: SEQ ID NO:86:

Gly Cys Glu Pro Arg Gly Asp Asn Xaa Cys Ala
1               5                   10

(2) INFORMATION FOR SEQ ID NO:87:

(i) SEQUENCE CHARACTERISTICS:
      (A) LENGTH: 7 amino acids
      (B) TYPE: amino acid
      (D) TOPOLOGY: circular (i i) MOLECULE TYPE: peptide (i x) FEATURE:
      (A) NAME/KEY: Peptide
      (B) LOCATION: 1
      (D) OTHER INFORMATION: /note= "Amino acid is acetylated at
         the N- terminal."

( i x ) FEATURE:
    ( A ) NAME/KEY: Peptide
    ( B ) LOCATION: 6
    ( D ) OTHER INFORMATION: /note= "Xaa is (Tic)"

( i x ) FEATURE:
    ( A ) NAME/KEY: Peptide
    ( B ) LOCATION: 7
    ( D ) OTHER INFORMATION: /note= "Xaa is (Pen)"

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:87:

Cys Arg Gly Asp Ser Xaa Xaa
1                       5

( 2 ) INFORMATION FOR SEQ ID NO:88:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Xaa is (Tic)"

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:88:

Cys Arg Gly Asp Thr Xaa Cys
1                       5

( 2 ) INFORMATION FOR SEQ ID NO:89:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 1
    ( D ) OTHER INFORMATION: /note= "Xaa is Pen"

( i x ) FEATURE:
    ( A ) NAME/KEY: Peptide
    ( B ) LOCATION: 8
    ( D ) OTHER INFORMATION: /note= "Xaa is (1-Nal)"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:89:

Xaa Ala Ala Arg Gly Asp Asn Xaa Cys
1                           5

( 2 ) INFORMATION FOR SEQ ID NO:90:

( i ) SEQUENCE CHARACTERISTICS:
    ( A ) LENGTH: 9 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 8
    ( D ) OTHER INFORMATION: /note= "Xaa is (fp)"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:90:

Cys Ala Ala Arg Gly Asp Asn Xaa Cys
1                           5

( 2 ) INFORMATION FOR SEQ ID NO:91:

( i ) SEQUENCE CHARACTERISTICS:
    ( A ) LENGTH: 7 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Xaa is (Tic)"

( i x ) FEATURE:
    ( A ) NAME/KEY: Peptide
    ( B ) LOCATION: 7
    ( D ) OTHER INFORMATION: /note= "Xaa is (Pen)"

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:91:

Cys Arg Gly Asp Asn Xaa Xaa
1                    5

( 2 ) INFORMATION FOR SEQ ID NO:92:

( i ) SEQUENCE CHARACTERISTICS:
        ( A ) LENGTH: 10 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 2
        ( D ) OTHER INFORMATION: /note= "Xaa is Pen"

( i x ) FEATURE:
        ( A ) NAME/KEY: Peptide
        ( B ) LOCATION: 10
        ( D ) OTHER INFORMATION: /note= "Amino acid is amidated at
            the C- terminal."

( x i ) SEQUENCE DESCRIPTION: SEQ ID NO:92:

Gly Xaa Gly Phe Arg Gly Asp Ser Pro Cys
1               5                   10

( 2 ) INFORMATION FOR SEQ ID NO:93:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6
        ( D ) OTHER INFORMATION: /note= "Xaa is (Tic)"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:93:

Cys Arg Gly Asp Ser Xaa Cys Ala Lys
1               5

( 2 ) INFORMATION FOR SEQ ID NO:94:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:

(A) NAME/KEY: Peptide
(B) LOCATION: 9
(D) OTHER INFORMATION: /note= "Amino acid is amidated at
    the C- terminal."

(xi) SEQUENCE DESCRIPTION: SEQ ID NO:94:

Xaa Phe Ala Arg Gly Asp Asp Val Cys
1               5

(2) INFORMATION FOR SEQ ID NO:95:

(i) SEQUENCE CHARACTERISTICS:
    (A) LENGTH: 9 amino acids
    (B) TYPE: amino acid
    (D) TOPOLOGY: circular (ii) MOLECULE TYPE: peptide (ix) FEATURE:
    (A) NAME/KEY: Peptide
    (B) LOCATION: 1
    (D) OTHER INFORMATION: /note= "Amino acid is acetylated at
        the N- terminal."

(ix) FEATURE:
    (A) NAME/KEY: Peptide
    (B) LOCATION: 1
    (D) OTHER INFORMATION: /note= "Xaa is Pen"

(ix) FEATURE:
    (A) NAME/KEY: Peptide
    (B) LOCATION: 2
    (D) OTHER INFORMATION: /note= "Xaa is (2-Nal)"

(ix) FEATURE:
    (A) NAME/KEY: Peptide
    (B) LOCATION: 9
    (D) OTHER INFORMATION: /note= "Amino acid is amidated at
        the C- terminal."

(xi) SEQUENCE DESCRIPTION: SEQ ID NO:95:

Xaa Xaa Ala Arg Gly Asp Asn Pro Cys
1               5

(2) INFORMATION FOR SEQ ID NO:96:

(i) SEQUENCE CHARACTERISTICS:
    (A) LENGTH: 9 amino acids
    (B) TYPE: amino acid
    (D) TOPOLOGY: circular (ii) MOLECULE TYPE: peptide (ix) FEATURE:
    (A) NAME/KEY: Peptide
    (B) LOCATION: 1
    (D) OTHER INFORMATION: /note= "Amino acid is acetylated at
        the N- terminal."

(ix) FEATURE:
    (A) NAME/KEY: Peptide
    (B) LOCATION: 8
    (D) OTHER INFORMATION: /note= "Xaa is (7-OMeTic)"

(ix) FEATURE:
    (A) NAME/KEY: Peptide
    (B) LOCATION: 9
    (D) OTHER INFORMATION: /note= "Amino acid is amidated at
        the C- terminal."

(xi) SEQUENCE DESCRIPTION: SEQ ID NO:96:

Cys Ala Ala Arg Gly Asp Asn Xaa Cys
1               5

( 2 ) INFORMATION FOR SEQ ID NO:97:

( i ) SEQUENCE CHARACTERISTICS:
        ( A ) LENGTH: 8 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 8
        ( D ) OTHER INFORMATION: /note= "Xaa is (Pen)"

( i x ) FEATURE:
        ( A ) NAME/KEY: Peptide
        ( B ) LOCATION: 8
        ( D ) OTHER INFORMATION: /note= "Amino acid is amidated at the C- terminal."

( x i ) SEQUENCE DESCRIPTION: SEQ ID NO:97:

Ala  Cys  Arg  Gly  Asp  Ser  Pro  Xaa
    1                             5

( 2 ) INFORMATION FOR SEQ ID NO:98:

( i ) SEQUENCE CHARACTERISTICS:
        ( A ) LENGTH: 10 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 8
        ( D ) OTHER INFORMATION: /note= "Xaa is (Tic)"

( i x ) FEATURE:
        ( A ) NAME/KEY: Peptide
        ( B ) LOCATION: 10
        ( D ) OTHER INFORMATION: /note= "Amino acid is amidated at the C- terminal."

( x i ) SEQUENCE DESCRIPTION: SEQ ID NO:98:

Cys  Ala  Ala  Arg  Gly  Asp  Asn  Xaa  Cys  Lys
    1                             5                            1 0

( 2 ) INFORMATION FOR SEQ ID NO:99:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide (B) LOCATION: 3
(D) OTHER INFORMATION: /note= "Xaa is (nMeF)"

(ix) FEATURE:
(A) NAME/KEY: Peptide
(B) LOCATION: 9
(D) OTHER INFORMATION: /note= "Amino acid is amidated at the C- terminal."

(xi) SEQUENCE DESCRIPTION: SEQ ID NO:99:

Xaa Ile Xaa Arg Gly Asp Thr Phe Cys
1               5

(2) INFORMATION FOR SEQ ID NO:100:

(i) SEQUENCE CHARACTERISTICS:
(A) LENGTH: 18 amino acids
(B) TYPE: amino acid
(D) TOPOLOGY: circular (ii) MOLECULE TYPE: peptide (ix) FEATURE:
(A) NAME/KEY: Peptide
(B) LOCATION: 17
(D) OTHER INFORMATION: /note= "Xaa is (Tic)"

(xi) SEQUENCE DESCRIPTION: SEQ ID NO:100:

Thr Ala Pro Gly Lys His Pro Asn Arg Cys Ala Ala Arg Gly Asp Asn
1               5                   10                  15

Xaa Cys (2) INFORMATION FOR SEQ ID NO:101:

(i) SEQUENCE CHARACTERISTICS:
(A) LENGTH: 9 amino acids
(B) TYPE: amino acid
(D) TOPOLOGY: circular (ii) MOLECULE TYPE: peptide (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 1
(D) OTHER INFORMATION: /note= "Xaa is Pen"

(ix) FEATURE:
(A) NAME/KEY: Peptide
(B) LOCATION: 8
(D) OTHER INFORMATION: /note= "Xaa is (PgL)"

(ix) FEATURE:
(A) NAME/KEY: Peptide
(B) LOCATION: 9
(D) OTHER INFORMATION: /note= "Amino acid is amidated at the C- terminal."

(xi) SEQUENCE DESCRIPTION: SEQ ID NO:101:

Xaa Phe Ala Arg Gly Asp Asp Xaa Cys
1               5

(2) INFORMATION FOR SEQ ID NO:102:

(i) SEQUENCE CHARACTERISTICS:
(A) LENGTH: 9 amino acids
(B) TYPE: amino acid
(D) TOPOLOGY: circular (  i  i  ) MOLECULE TYPE: peptide (  i  x  ) FEATURE:
    ( A ) NAME/KEY: Peptide
    ( B ) LOCATION: 1
    ( D ) OTHER INFORMATION: /note= "Amino acid is acetylated at
        the N- terminal."

(  i  x  ) FEATURE:
    ( A ) NAME/KEY: Peptide
    ( B ) LOCATION: 8
    ( D ) OTHER INFORMATION: /note= "Xaa is (Tic)"

(  i  x  ) FEATURE:
    ( A ) NAME/KEY: Peptide
    ( B ) LOCATION: 9
    ( D ) OTHER INFORMATION: /note= "Amino acid is amidated at
        the C- terminal."

(  x  i  ) SEQUENCE DESCRIPTION: SEQ ID NO:102:

Cys Phe Ala Arg Gly Asp Thr Xaa Cys
1                   5

( 2 ) INFORMATION FOR SEQ ID NO:103:

(  i  ) SEQUENCE CHARACTERISTICS:
        ( A ) LENGTH: 7 amino acids
        ( B ) TYPE: amino acid
        ( D ) TOPOLOGY: circular (  i  i  ) MOLECULE TYPE: peptide (  i  x  ) FEATURE:
        ( A ) NAME/KEY: Peptide
        ( B ) LOCATION: 1
        ( D ) OTHER INFORMATION: /note= "Xaa is (Mpa)"

(  i  x  ) FEATURE:
        ( A ) NAME/KEY: Peptide
        ( B ) LOCATION: 6
        ( D ) OTHER INFORMATION: /note= "Xaa is (t-BuG)"

(  i  x  ) FEATURE:
        ( A ) NAME/KEY: Peptide
        ( B ) LOCATION: 7
        ( D ) OTHER INFORMATION: /note= "Amino acid is amidated at
        the C- terminal."

(  x  i  ) SEQUENCE DESCRIPTION: SEQ ID NO:103:

Xaa Arg Gly Asp Asp Xaa Cys
1                   5

( 2 ) INFORMATION FOR SEQ ID NO:104:

(  i  ) SEQUENCE CHARACTERISTICS:
        ( A ) LENGTH: 7 amino acids
        ( B ) TYPE: amino acid
        ( D ) TOPOLOGY: circular (  i  i  ) MOLECULE TYPE: peptide (  i  x  ) FEATURE:
        ( A ) NAME/KEY: Peptide
        ( B ) LOCATION: 1
        ( D ) OTHER INFORMATION: /note= "Xaa is (Mpa)"

(  i  x  ) FEATURE:
        ( A ) NAME/KEY: Peptide
        ( B ) LOCATION: 6
        ( D ) OTHER INFORMATION: /note= "Xaa is (cha)"

(  i  x  ) FEATURE:
        ( A ) NAME/KEY: Peptide
        ( B ) LOCATION: 7
        ( D ) OTHER INFORMATION: /note= "Amino acid is amidated at -continued the C- terminal."

( x i ) SEQUENCE DESCRIPTION: SEQ ID NO:104:

Xaa Arg Gly Asp Asp Xaa Cys
1               5

( 2 ) INFORMATION FOR SEQ ID NO:105:

( i ) SEQUENCE CHARACTERISTICS:
      ( A ) LENGTH: 6 amino acids
      ( B ) TYPE: amino acid
      ( D ) TOPOLOGY: circular ( i i ) MOLECULE TYPE: peptide ( i x ) FEATURE:
      ( A ) NAME/KEY: Peptide
      ( B ) LOCATION: 5
      ( D ) OTHER INFORMATION: /note= "Xaa is (Tic)"

( i x ) FEATURE:
      ( A ) NAME/KEY: Peptide
      ( B ) LOCATION: 6
      ( D ) OTHER INFORMATION: /note= "Amino acid is amidated at
          the C- terminal."

( x i ) SEQUENCE DESCRIPTION: SEQ ID NO:105:

Arg Gly Asp Asn Xaa Glu
1               5

( 2 ) INFORMATION FOR SEQ ID NO:106:

( i ) SEQUENCE CHARACTERISTICS:
      ( A ) LENGTH: 11 amino acids
      ( B ) TYPE: amino acid
      ( D ) TOPOLOGY: circular ( i i ) MOLECULE TYPE: peptide ( i x ) FEATURE:
      ( A ) NAME/KEY: Peptide
      ( B ) LOCATION: 1
      ( D ) OTHER INFORMATION: /note= "Amino acid is acetylated at
          the N- terminal."

( i x ) FEATURE:
      ( A ) NAME/KEY: Peptide
      ( B ) LOCATION: 8
      ( D ) OTHER INFORMATION: /note= "Xaa is (Tic)"

( i x ) FEATURE:
      ( A ) NAME/KEY: Peptide
      ( B ) LOCATION: 11
      ( D ) OTHER INFORMATION: /note= "Amino acid is amidated at
          the C- terminal."

( x i ) SEQUENCE DESCRIPTION: SEQ ID NO:106:

Cys Ala Ala Arg Gly Asp Asn Xaa Cys Ala Lys
1               5                   1 0

( 2 ) INFORMATION FOR SEQ ID NO:107:

( i ) SEQUENCE CHARACTERISTICS:
      ( A ) LENGTH: 7 amino acids
      ( B ) TYPE: amino acid
      ( D ) TOPOLOGY: circular ( i i ) MOLECULE TYPE: peptide ( i x ) FEATURE:
      ( A ) NAME/KEY: Peptide
      ( B ) LOCATION: 1
      ( D ) OTHER INFORMATION: /note= "Amino acid is acetylated at
          the N- terminal."

( i x ) FEATURE:
  ( A ) NAME/KEY: Peptide
  ( B ) LOCATION: 6
  ( D ) OTHER INFORMATION: /note= "Xaa is (Tca)"

( i x ) FEATURE:
  ( A ) NAME/KEY: Peptide
  ( B ) LOCATION: 7
  ( D ) OTHER INFORMATION: /note= "Amino acid is amidated at
    the C- terminal."

( x i ) SEQUENCE DESCRIPTION: SEQ ID NO:107:

Cys Arg Gly Asp Thr Xaa Cys
1                 5

( 2 ) INFORMATION FOR SEQ ID NO:108:

( i ) SEQUENCE CHARACTERISTICS:
    ( A ) LENGTH: 7 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at
      the N- terminal."

( i x ) FEATURE:
    ( A ) NAME/KEY: Peptide
    ( B ) LOCATION: 6
    ( D ) OTHER INFORMATION: /note= "Xaa is (Ole)"

( i x ) FEATURE:
    ( A ) NAME/KEY: Peptide
    ( B ) LOCATION: 7
    ( D ) OTHER INFORMATION: /note= "Amino acid is amidated at
      the C- terminal."

( x i ) SEQUENCE DESCRIPTION: SEQ ID NO:108:

Cys Arg Gly Asp Thr Xaa Cys
1                 5

( 2 ) INFORMATION FOR SEQ ID NO:109:

( i ) SEQUENCE CHARACTERISTICS:
    ( A ) LENGTH: 9 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at
      the N- terminal."

( i x ) FEATURE:
    ( A ) NAME/KEY: Peptide
    ( B ) LOCATION: 1
    ( D ) OTHER INFORMATION: /note= "Xaa is (Pen)"

( i x ) FEATURE:
    ( A ) NAME/KEY: Peptide
    ( B ) LOCATION: 9
    ( D ) OTHER INFORMATION: /note= "Amino acid is amidated at
      the C- terminal."

( x i ) SEQUENCE DESCRIPTION: SEQ ID NO:109:

Xaa Glu Ala Arg Gly Asp Asp Val Cys
1                 5

( 2 ) INFORMATION FOR SEQ ID NO:110:

( i ) SEQUENCE CHARACTERISTICS:
  ( A ) LENGTH: 9 amino acids
  ( B ) TYPE: amino acid
  ( D ) TOPOLOGY: circular ( i i ) MOLECULE TYPE: peptide ( i x ) FEATURE:
  ( A ) NAME/KEY: Peptide
  ( B ) LOCATION: 8
  ( D ) OTHER INFORMATION: /note= "Xaa is (Tic)"

( i x ) FEATURE:
  ( A ) NAME/KEY: Peptide
  ( B ) LOCATION: 9
  ( D ) OTHER INFORMATION: /note= "Amino acid is amidated at
   the C- terminal."

( x i ) SEQUENCE DESCRIPTION: SEQ ID NO:110:

Gly Ala Ala Arg Gly Asp Ser Xaa Glu
 1         5

( 2 ) INFORMATION FOR SEQ ID NO:111:

( i ) SEQUENCE CHARACTERISTICS:
  ( A ) LENGTH: 9 amino acids
  ( B ) TYPE: amino acid
  ( D ) TOPOLOGY: circular ( i i ) MOLECULE TYPE: peptide ( i x ) FEATURE:
  ( A ) NAME/KEY: Peptide
  ( B ) LOCATION: 1
  ( D ) OTHER INFORMATION: /note= "Amino acid is acetylated at
   the N- terminal."

( i x ) FEATURE:
  ( A ) NAME/KEY: Peptide
  ( B ) LOCATION: 1
  ( D ) OTHER INFORMATION: /note= "Xaa is (Pen)"

( i x ) FEATURE:
  ( A ) NAME/KEY: Peptide
  ( B ) LOCATION: 8
  ( D ) OTHER INFORMATION: /note= "Xaa is (homoP)"

( i x ) FEATURE:
  ( A ) NAME/KEY: Peptide
  ( B ) LOCATION: 9
  ( D ) OTHER INFORMATION: /note= "Amino acid is amidated at
   the C- terminal."

( x i ) SEQUENCE DESCRIPTION: SEQ ID NO:111:

Xaa Ala Ala Arg Gly Asp Asn Xaa Cys
 1         5

( 2 ) INFORMATION FOR SEQ ID NO:112:

( i ) SEQUENCE CHARACTERISTICS:
  ( A ) LENGTH: 5 amino acids
  ( B ) TYPE: amino acid
  ( D ) TOPOLOGY: circular ( i i ) MOLECULE TYPE: peptide ( i x ) FEATURE:
  ( A ) NAME/KEY: Peptide
  ( B ) LOCATION: 5
  ( D ) OTHER INFORMATION: /note= "Xaa is (Adp)"

( i x ) FEATURE:

(A) NAME/KEY: Peptide
(B) LOCATION: 5
(D) OTHER INFORMATION: /note= "Amino acid is amidated at the C- terminal."

(x i) SEQUENCE DESCRIPTION: SEQ ID NO:112:

Arg Gly Asp Ser Xaa
1               5

(2) INFORMATION FOR SEQ ID NO:113:

(i) SEQUENCE CHARACTERISTICS:
(A) LENGTH: 9 amino acids
(B) TYPE: amino acid
(D) TOPOLOGY: circular (i i) MOLECULE TYPE: peptide (i x) FEATURE:
(A) NAME/KEY: Peptide
(B) LOCATION: 1
(D) OTHER INFORMATION: /note= "Amino acid is acetylated at the N- terminal."

(i x) FEATURE:
(A) NAME/KEY: Peptide
(B) LOCATION: 8
(D) OTHER INFORMATION: /note= "Xaa is (Tic)"

(i x) FEATURE:
(A) NAME/KEY: Peptide
(B) LOCATION: 9
(D) OTHER INFORMATION: /note= "Amino acid is amidated at the C- terminal."

(x i) SEQUENCE DESCRIPTION: SEQ ID NO:113:

Cys Glu Pro Arg Gly Asp Asn Xaa Cys
1               5

(2) INFORMATION FOR SEQ ID NO:114:

(i) SEQUENCE CHARACTERISTICS:
(A) LENGTH: 10 amino acids
(B) TYPE: amino acid
(D) TOPOLOGY: circular (i i) MOLECULE TYPE: peptide (i x) FEATURE:
(A) NAME/KEY: Peptide
(B) LOCATION: 1
(D) OTHER INFORMATION: /note= "Xaa is (Pmp)"

(i x) FEATURE:
(A) NAME/KEY: Peptide
(B) LOCATION: 9
(D) OTHER INFORMATION: /note= "Xaa is (Tic)"

(i x) FEATURE:
(A) NAME/KEY: Peptide
(B) LOCATION: 10
(D) OTHER INFORMATION: /note= "Amino acid is amidated at the C- terminal."

(x i) SEQUENCE DESCRIPTION: SEQ ID NO:114:

Xaa Ala Ala Arg Gly Asp Asp Asn Xaa Cys
1               5                   10

(2) INFORMATION FOR SEQ ID NO:115:

(i) SEQUENCE CHARACTERISTICS:
(A) LENGTH: 8 amino acids
(B) TYPE: amino acid
(D) TOPOLOGY: circular (i i) MOLECULE TYPE: peptide (i x) FEATURE:
    (A) NAME/KEY: Peptide
    (B) LOCATION: 8
    (D) OTHER INFORMATION: /note= "Xaa is (Adp)"

(i x) FEATURE:
    (A) NAME/KEY: Peptide
    (B) LOCATION: 8
    (D) OTHER INFORMATION: /note= "Amino acid is amidated at the C- terminal."

(x i) SEQUENCE DESCRIPTION: SEQ ID NO:115:

Ala Ala Arg Gly Asp Asp Val Xaa
1                 5

(2) INFORMATION FOR SEQ ID NO:116:

(i) SEQUENCE CHARACTERISTICS:
        (A) LENGTH: 9 amino acids
        (B) TYPE: amino acid
        (D) TOPOLOGY: circular (i i) MOLECULE TYPE: peptide (i x) FEATURE:
    (A) NAME/KEY: Peptide
    (B) LOCATION: 1
    (D) OTHER INFORMATION: /note= "Amino acid is acetylated at the N- terminal."

(i x) FEATURE:
    (A) NAME/KEY: Peptide
    (B) LOCATION: 1
    (D) OTHER INFORMATION: /note= "Xaa is (Pen)"

(i x) FEATURE:
    (A) NAME/KEY: Peptide
    (B) LOCATION: 9
    (D) OTHER INFORMATION: /note= "Amino acid is amidated at the C- terminal."

(x i) SEQUENCE DESCRIPTION: SEQ ID NO:116:

Xaa Glu Pro Arg Gly Asp Asp Val Cys
1                 5

(2) INFORMATION FOR SEQ ID NO:117:

(i) SEQUENCE CHARACTERISTICS:
        (A) LENGTH: 7 amino acids
        (B) TYPE: amino acid
        (D) TOPOLOGY: circular (i i) MOLECULE TYPE: peptide (i x) FEATURE:
    (A) NAME/KEY: Peptide
    (B) LOCATION: 1
    (D) OTHER INFORMATION: /note= "Xaa is (Mpa)"

(i x) FEATURE:
    (A) NAME/KEY: Peptide
    (B) LOCATION: 6
    (D) OTHER INFORMATION: /note= "Xaa is (npG)"

(i x) FEATURE:
    (A) NAME/KEY: Peptide
    (B) LOCATION: 7
    (D) OTHER INFORMATION: /note= "Amino acid is amidated at the C- terminal."

(x i) SEQUENCE DESCRIPTION: SEQ ID NO:117:

Xaa Arg Gly Asp Asp Xaa Cys ( 2 ) INFORMATION FOR SEQ ID NO:118:

( i ) SEQUENCE CHARACTERISTICS:
        ( A ) LENGTH: 10 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is (Pen)"

( i x ) FEATURE:
        ( A ) NAME/KEY: Peptide
        ( B ) LOCATION: 8
        ( D ) OTHER INFORMATION: /note= "Xaa is (tBuG)"

( x i ) SEQUENCE DESCRIPTION: SEQ ID NO:118:

```
Xaa  Ile  Gly  Arg  Gly  Asp  Asp  Xaa  Cys  Ala
 1                    5                      1 0
```

( 2 ) INFORMATION FOR SEQ ID NO:119:

( i ) SEQUENCE CHARACTERISTICS:
        ( A ) LENGTH: 8 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is (Mpa)"

( i x ) FEATURE:
        ( A ) NAME/KEY: Peptide
        ( B ) LOCATION: 6
        ( D ) OTHER INFORMATION: /note= "Xaa is (tBuG)"

( x i ) SEQUENCE DESCRIPTION: SEQ ID NO:119:

```
Xaa  Arg  Gly  Asp  Asp  Xaa  Cys  Ala
 1                    5
```

( 2 ) INFORMATION FOR SEQ ID NO:120:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is (Mpa)"

( i x ) FEATURE:
        ( A ) NAME/KEY: Peptide
        ( B ) LOCATION: 5
        ( D ) OTHER INFORMATION: /note= "Xaa is (tetA)"

( i x ) FEATURE:
        ( A ) NAME/KEY: Peptide ( B ) LOCATION: 6
            ( D ) OTHER INFORMATION: /note= "Xaa is (tBuG)"

( i x ) FEATURE:
            ( A ) NAME/KEY: Peptide
            ( B ) LOCATION: 7
            ( D ) OTHER INFORMATION: /note= "Amino acid is amidated at
                the C- terminal."

( x i ) SEQUENCE DESCRIPTION: SEQ ID NO:120:

Xaa   Arg   Gly   Asp   Xaa   Xaa   Cys
    1                       5

( 2 ) INFORMATION FOR SEQ ID NO:121:

( i ) SEQUENCE CHARACTERISTICS:
            ( A ) LENGTH: 10 amino acids
            ( B ) TYPE: amino acid
            ( D ) TOPOLOGY: circular ( i i ) MOLECULE TYPE: peptide ( i x ) FEATURE:
            ( A ) NAME/KEY: Peptide
            ( B ) LOCATION: 1
            ( D ) OTHER INFORMATION: /note= "Amino acid is acetylated at
                the N- terminal."

( i x ) FEATURE:
            ( A ) NAME/KEY: Peptide
            ( B ) LOCATION: 4
            ( D ) OTHER INFORMATION: /note= "Xaa is (HomoR)"

( i x ) FEATURE:
            ( A ) NAME/KEY: Peptide
            ( B ) LOCATION: 9
            ( D ) OTHER INFORMATION: /note= "Xaa is (Tic)"

( i x ) FEATURE:
            ( A ) NAME/KEY: Peptide
            ( B ) LOCATION: 10
            ( D ) OTHER INFORMATION: /note= "Amino acid is amidated at
                the C- terminal."

( x i ) SEQUENCE DESCRIPTION: SEQ ID NO:121:

Cys   Ala   Ala   Xaa   Arg   Gly   Asp   Asn   Xaa   Cys
    1                       5                             1 0

( 2 ) INFORMATION FOR SEQ ID NO:122:

( i ) SEQUENCE CHARACTERISTICS:
            ( A ) LENGTH: 7 amino acids
            ( B ) TYPE: amino acid
            ( D ) TOPOLOGY: circular ( i i ) MOLECULE TYPE: peptide ( i x ) FEATURE:
            ( A ) NAME/KEY: Peptide
            ( B ) LOCATION: 1
            ( D ) OTHER INFORMATION: /note= "Amino acid is acetylated at
                the N- terminal."

( i x ) FEATURE:
            ( A ) NAME/KEY: Peptide
            ( B ) LOCATION: 2
            ( D ) OTHER INFORMATION: /note= "Xaa is (nMeR)"

( i x ) FEATURE:
            ( A ) NAME/KEY: Peptide
            ( B ) LOCATION: 6
            ( D ) OTHER INFORMATION: /note= "Xaa is (Tic)"

( i x ) FEATURE:
            ( A ) NAME/KEY: Peptide
            ( B ) LOCATION: 7

( D ) OTHER INFORMATION: /note= "Amino acid is amidated at
the C- terminal."

( x i ) SEQUENCE DESCRIPTION: SEQ ID NO:122:

Cys  Xaa  Gly  Asp  Thr  Xaa  Cys
1                   5

( 2 ) INFORMATION FOR SEQ ID NO:123:

( i ) SEQUENCE CHARACTERISTICS:
( A ) LENGTH: 9 amino acids
( B ) TYPE: amino acid
( D ) TOPOLOGY: circular ( i i ) MOLECULE TYPE: peptide ( i x ) FEATURE:
( A ) NAME/KEY: Peptide
( B ) LOCATION: 1
( D ) OTHER INFORMATION: /note= "Xaa is (Mpa)"

( i x ) FEATURE:
( A ) NAME/KEY: Peptide
( B ) LOCATION: 6
( D ) OTHER INFORMATION: /note= "Xaa is (tBuG)"

( i x ) FEATURE:
( A ) NAME/KEY: Peptide
( B ) LOCATION: 9
( D ) OTHER INFORMATION: /note= "Amino acid is amidated at
the C- terminal."

( x i ) SEQUENCE DESCRIPTION: SEQ ID NO:123:

Xaa  Arg  Gly  Asp  Asp  Xaa  Cys  Ala  Lys
1                   5

( 2 ) INFORMATION FOR SEQ ID NO:124:

( i ) SEQUENCE CHARACTERISTICS:
( A ) LENGTH: 8 amino acids
( B ) TYPE: amino acid
( D ) TOPOLOGY: circular ( i i ) MOLECULE TYPE: peptide ( i x ) FEATURE:
( A ) NAME/KEY: Peptide
( B ) LOCATION: 1
( D ) OTHER INFORMATION: /note= "Xaa is (Mpa)"

( i x ) FEATURE:
( A ) NAME/KEY: Peptide
( B ) LOCATION: 6
( D ) OTHER INFORMATION: /note= "Xaa is (tBuG)"

( i x ) FEATURE:
( A ) NAME/KEY: Peptide
( B ) LOCATION: 8
( D ) OTHER INFORMATION: /note= "Amino acid is amidated at
the C- terminal."

( x i ) SEQUENCE DESCRIPTION: SEQ ID NO:124:

Xaa  Arg  Gly  Asp  Asp  Xaa  Cys  Asp
1                   5

( 2 ) INFORMATION FOR SEQ ID NO:125:

( i ) SEQUENCE CHARACTERISTICS:
( A ) LENGTH: 8 amino acids
( B ) TYPE: amino acid
( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Amino acid is acetylated at
        the N- terminal."

( i x ) FEATURE:
    ( A ) NAME/KEY: Peptide
    ( B ) LOCATION: 7
    ( D ) OTHER INFORMATION: /note= "Xaa is (Tic)"

( i x ) FEATURE:
    ( A ) NAME/KEY: Peptide
    ( B ) LOCATION: 8
    ( D ) OTHER INFORMATION: /note= "Amino acid is amidated at
        the C- terminal."

( x i ) SEQUENCE DESCRIPTION: SEQ ID NO:125:

Phe Cys Arg Gly Asp Thr Xaa Cys
1                           5

( 2 ) INFORMATION FOR SEQ ID NO:126:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is (Mpa)"

( i x ) FEATURE:
        ( A ) NAME/KEY: Peptide
        ( B ) LOCATION: 5
        ( D ) OTHER INFORMATION: /note= "Xaa is (Msa)"

( i x ) FEATURE:
        ( A ) NAME/KEY: Peptide
        ( B ) LOCATION: 6
        ( D ) OTHER INFORMATION: /note= "Xaa is (tBuG)"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:126:

Xaa Arg Gly Asp Xaa Xaa Cys
1                         5

( 2 ) INFORMATION FOR SEQ ID NO:127:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 6
        ( D ) OTHER INFORMATION: /note= "Xaa is (tBuG)"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:127:

Gly  Arg  Gly  Asp  Asp  Xaa  Glu
                    1                   5

( 2 ) INFORMATION FOR SEQ ID NO:128:

( i ) SEQUENCE CHARACTERISTICS:
                ( A ) LENGTH: 8 amino acids
                ( B ) TYPE: amino acid
                ( D ) TOPOLOGY: circular ( i i ) MOLECULE TYPE: peptide ( i x ) FEATURE:
                ( A ) NAME/KEY: Peptide
                ( B ) LOCATION: 1
                ( D ) OTHER INFORMATION: /note= "Xaa is (Mpa)"

( i x ) FEATURE:
                ( A ) NAME/KEY: Peptide
                ( B ) LOCATION: 6
                ( D ) OTHER INFORMATION: /note= "Xaa is (tBuG)"

( i x ) FEATURE:
                ( A ) NAME/KEY: Peptide
                ( B ) LOCATION: 8
                ( D ) OTHER INFORMATION: /note= "Amino acid is amidated at
                        the C- terminal."

( x i ) SEQUENCE DESCRIPTION: SEQ ID NO:128:

Xaa  Arg  Gly  Asp  Asp  Xaa  Cys  Phe
        1                   5

( 2 ) INFORMATION FOR SEQ ID NO:129:

( i ) SEQUENCE CHARACTERISTICS:
                ( A ) LENGTH: 7 amino acids
                ( B ) TYPE: amino acid
                ( D ) TOPOLOGY: circular ( i i ) MOLECULE TYPE: peptide ( i x ) FEATURE:
                ( A ) NAME/KEY: Peptide
                ( B ) LOCATION: 1
                ( D ) OTHER INFORMATION: /note= "Xaa is (Beta-Ala)"

( i x ) FEATURE:
                ( A ) NAME/KEY: Peptide
                ( B ) LOCATION: 6
                ( D ) OTHER INFORMATION: /note= "Xaa is (tBuG)"

( i x ) FEATURE:
                ( A ) NAME/KEY: Peptide
                ( B ) LOCATION: 7
                ( D ) OTHER INFORMATION: /note= "Amino acid is amidated at
                        the C- terminal."

( x i ) SEQUENCE DESCRIPTION: SEQ ID NO:129:

Xaa  Arg  Gly  Asp  Asp  Xaa  Asp
        1                   5

( 2 ) INFORMATION FOR SEQ ID NO:130:

( i ) SEQUENCE CHARACTERISTICS:
                ( A ) LENGTH: 7 amino acids
                ( B ) TYPE: amino acid
                ( D ) TOPOLOGY: circular ( i i ) MOLECULE TYPE: peptide ( i x ) FEATURE:
                ( A ) NAME/KEY: Peptide
                ( B ) LOCATION: 1
                ( D ) OTHER INFORMATION: /note= "Xaa is (Mpa)"

( i x ) FEATURE:
    ( A ) NAME/KEY: Peptide
    ( B ) LOCATION: 2
    ( D ) OTHER INFORMATION: /note= "Xaa is (nMeR)"

( i x ) FEATURE:
    ( A ) NAME/KEY: Peptide
    ( B ) LOCATION: 6
    ( D ) OTHER INFORMATION: /note= "Xaa is (tBuG)"

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:130:

```
Xaa  Xaa  Gly  Asp  Asp  Xaa  Cys
1                   5
```

( 2 ) INFORMATION FOR SEQ ID NO:131:

( i ) SEQUENCE CHARACTERISTICS:
    ( A ) LENGTH: 7 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Xaa is (Mpa)"

( i x ) FEATURE:
    ( A ) NAME/KEY: Peptide
    ( B ) LOCATION: 5
    ( D ) OTHER INFORMATION: /note= "Xaa is (Psa)"

( i x ) FEATURE:
    ( A ) NAME/KEY: Peptide
    ( B ) LOCATION: 6
    ( D ) OTHER INFORMATION: /note= "Xaa is (tBuG)"

( i x ) FEATURE:
    ( A ) NAME/KEY: Peptide
    ( B ) LOCATION: 7
    ( D ) OTHER INFORMATION: /note= "Amino acid is amidated at C- terminal."

( x i ) SEQUENCE DESCRIPTION: SEQ ID NO:131:

```
Xaa  Arg  Gly  Asp  Xaa  Xaa  Cys
1                   5
```

( 2 ) INFORMATION FOR SEQ ID NO:132:

( i ) SEQUENCE CHARACTERISTICS:
    ( A ) LENGTH: 7 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "Xaa is (Mpa)"

( i x ) FEATURE:
    ( A ) NAME/KEY: Peptide
    ( B ) LOCATION: 5
    ( D ) OTHER INFORMATION: /note= "Xaa is (YOMe)"

( i x ) FEATURE:
    ( A ) NAME/KEY: Peptide (B) LOCATION: 6
            (D) OTHER INFORMATION: /note= "Xaa is (tBuG)"

(ix) FEATURE:
            (A) NAME/KEY: Peptide
            (B) LOCATION: 7
            (D) OTHER INFORMATION: /note= "Amino acid is amidated at
                C- terminal."

(xi) SEQUENCE DESCRIPTION: SEQ ID NO:132:

Xaa  Arg  Gly  Asp  Xaa  Xaa  Cys
    1                   5

(2) INFORMATION FOR SEQ ID NO:133:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (ix) FEATURE:
        (A) NAME/KEY: Peptide
        (B) LOCATION: 1
        (D) OTHER INFORMATION: /note= "Xaa is (Mpa)"

(ix) FEATURE:
        (A) NAME/KEY: Peptide
        (B) LOCATION: 9
        (D) OTHER INFORMATION: /note= "Amino acid is amidated at
            the C- terminal."

(xi) SEQUENCE DESCRIPTION: SEQ ID NO:133:

Xaa  Arg  Gly  Asp  Asp  Val  Cys  Ala  Lys
    1                   5

(2) INFORMATION FOR SEQ ID NO:134:

(i) SEQUENCE CHARACTERISTICS:
        (A) LENGTH: 7 amino acids
        (B) TYPE: amino acid
        (D) TOPOLOGY: circular (ii) MOLECULE TYPE: peptide (ix) FEATURE:
        (A) NAME/KEY: Peptide
        (B) LOCATION: 1
        (D) OTHER INFORMATION: /note= "Xaa is (Mpa)"

(ix) FEATURE:
        (A) NAME/KEY: Peptide
        (B) LOCATION: 6
        (D) OTHER INFORMATION: /note= "Xaa is (PgL)"

(ix) FEATURE:
        (A) NAME/KEY: Peptide
        (B) LOCATION: 7
        (D) OTHER INFORMATION: /note= "Amino acid is amidated at
            the C- terminal."

(xi) SEQUENCE DESCRIPTION: SEQ ID NO:134:

Xaa  Arg  Gly  Asp  Asp  Xaa  Cys
    1                   5

(2) INFORMATION FOR SEQ ID NO:135:

(i) SEQUENCE CHARACTERISTICS:
        (A) LENGTH: 6 amino acids
        (B) TYPE: amino acid
        (D) TOPOLOGY: circular (ii) MOLECULE TYPE: peptide ( i x ) FEATURE:
    ( A ) NAME/KEY: Peptide
    ( B ) LOCATION: 5
    ( D ) OTHER INFORMATION: /note= "Xaa is (tBuG)"

( i x ) FEATURE:
    ( A ) NAME/KEY: Peptide
    ( B ) LOCATION: 6
    ( D ) OTHER INFORMATION: /note= "Xaa is (Mamb)"

( x i ) SEQUENCE DESCRIPTION: SEQ ID NO:135:

Arg Gly Asp Asp Xaa Xaa
1                          5

( 2 ) INFORMATION FOR SEQ ID NO:136:

( i ) SEQUENCE CHARACTERISTICS:
        ( A ) LENGTH: 7 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa is (Mpa)"

( i x ) FEATURE:
        ( A ) NAME/KEY: Peptide
        ( B ) LOCATION: 5
        ( D ) OTHER INFORMATION: /note= "Xaa is (Tlsa)"

( i x ) FEATURE:
        ( A ) NAME/KEY: Peptide
        ( B ) LOCATION: 6
        ( D ) OTHER INFORMATION: /note= "Xaa is (tBuG)"

( i x ) FEATURE:
        ( A ) NAME/KEY: Peptide
        ( B ) LOCATION: 7
        ( D ) OTHER INFORMATION: /note= "Amino acid is amidated at
                the C- terminal."

( x i ) SEQUENCE DESCRIPTION: SEQ ID NO:136:

Xaa Arg Gly Asp Xaa Xaa Cys
1                        5

( 2 ) INFORMATION FOR SEQ ID NO:137:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid is acetylated at
                the N- terminal."

( i x ) FEATURE:
        ( A ) NAME/KEY: Peptide
        ( B ) LOCATION: 1
        ( D ) OTHER INFORMATION: /note= "Xaa is (Pen)"

( i x ) FEATURE:
        ( A ) NAME/KEY: Peptide
        ( B ) LOCATION: 2
        ( D ) OTHER INFORMATION: /note= "Xaa is (YOMe)"

( i x ) FEATURE:
        ( A ) NAME/KEY: Peptide

-continued

```
            ( B ) LOCATION: 8
            ( D ) OTHER INFORMATION: /note= "Xaa is (Tic)"

( i x ) FEATURE:
            ( A ) NAME/KEY: Peptide
            ( B ) LOCATION: 9
            ( D ) OTHER INFORMATION: /note= "Amino acid is amidated at
                  the C- terminal."

( x i ) SEQUENCE DESCRIPTION: SEQ ID NO:137:

Xaa  Xaa  Ala  Arg  Gly  Asp  Thr  Xaa  Cys
    1                   5

( 2 ) INFORMATION FOR SEQ ID NO:138:

( i ) SEQUENCE CHARACTERISTICS:
            ( A ) LENGTH: 6 amino acids
            ( B ) TYPE: amino acid
            ( D ) TOPOLOGY: circular ( i i ) MOLECULE TYPE: peptide ( i x ) FEATURE:
            ( A ) NAME/KEY: Peptide
            ( B ) LOCATION: 4
            ( D ) OTHER INFORMATION: /note= "Xaa is (YOMe)"

( i x ) FEATURE:
            ( A ) NAME/KEY: Peptide
            ( B ) LOCATION: 6
            ( D ) OTHER INFORMATION: /note= "Amino acid is amidated at
                  the C- terminal."

( x i ) SEQUENCE DESCRIPTION: SEQ ID NO:138:

Arg  Gly  Asp  Xaa  Arg  Glu
    1                   5
```